US010883109B2

(12) United States Patent
Coller et al.

(10) Patent No.: US 10,883,109 B2
(45) **Date of Patent: *Jan. 5, 2021**

(54) METHODS OF MODULATING MRNA STABILITY AND PROTEIN EXPRESSION

(71) Applicant: CASE WESTERN RESERVE UNIVERSITY, Cleveland, OH (US)

(72) Inventors: Jeffery M. Coller, Novelty, OH (US); Kristian E. Baker, Novelty, OH (US)

(73) Assignee: CASE WESTERN RESERVE UNIVERSITY, Cleveland, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 15/713,081

(22) Filed: Sep. 22, 2017

(65) Prior Publication Data

US 2018/0135061 A1 May 17, 2018
US 2020/0140872 A9 May 7, 2020

Related U.S. Application Data

(63) Continuation-in-part of application No. 15/557,412, filed as application No. PCT/US2016/021594 on Mar. 9, 2016.

(60) Provisional application No. 62/398,281, filed on Sep. 22, 2016, provisional application No. 62/130,398, filed on Mar. 9, 2015.

(51) Int. Cl.

| | |
|---|---|
| ***C12N 15/68*** | (2006.01) |
| ***C12N 15/81*** | (2006.01) |
| ***C12N 9/34*** | (2006.01) |
| ***C12N 15/85*** | (2006.01) |

(52) U.S. Cl.
CPC ........... *C12N 15/68* (2013.01); *C12N 9/2428* (2013.01); *C12N 15/81* (2013.01); *C12N 15/85* (2013.01); *C12N 2800/22* (2013.01)

(58) Field of Classification Search
None
See application file for complete search history.

(56) References Cited

PUBLICATIONS

Koresawa et al., “Synthesis of a New Cre Recombinase Gene Based on Optimal Codon Usage for Mammalian Systems” 127 Journal of Biochemistry 367-372 (2000).*
Favaro et al., “Codon-optimized glucoamylase SGAI of Aspergillus awamori improves starch utilization in an industrial yeast” 95 Applied Microbiology and Biotechnology 957-968 (2012).*
Presnyak et al., “Codon Optimality Is a Major Determinant of mRNA Stability” 160 Cell 1111-1124 (Mar. 12, 2015).*
Sinclair, Graham, et al. “Synonymous codon usage bias and the expression of human glucocerebrosidase—in the methylotropic yeast, *Pichia pastoris*”, Protein Expression Purification 26 (2002).

* cited by examiner

*Primary Examiner* — Nancy J Leith
(74) *Attorney, Agent, or Firm* — Tarolli, Sundheim, Covell & Tummino LLP

(57) ABSTRACT

A synthetic cDNA which encodes a protein wherein at least one optimal or non-optimal codon in a wild type DNA encoding the protein has been replaced respectively with one or more non-optimal codons or optimal codons encoding the same amino acid.

6 Claims, 24 Drawing Sheets

Specification includes a Sequence Listing.

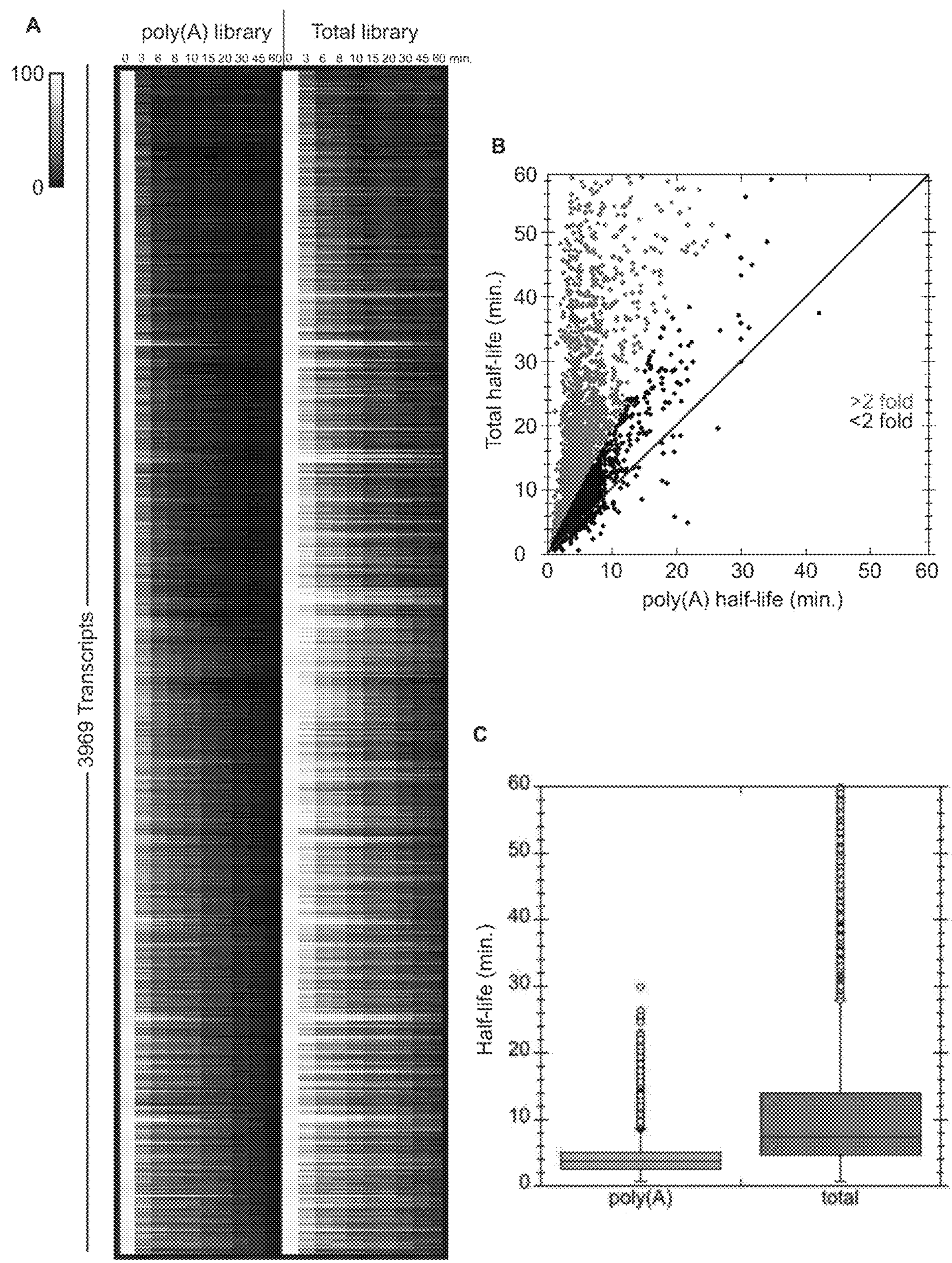
Figs. 1A-C

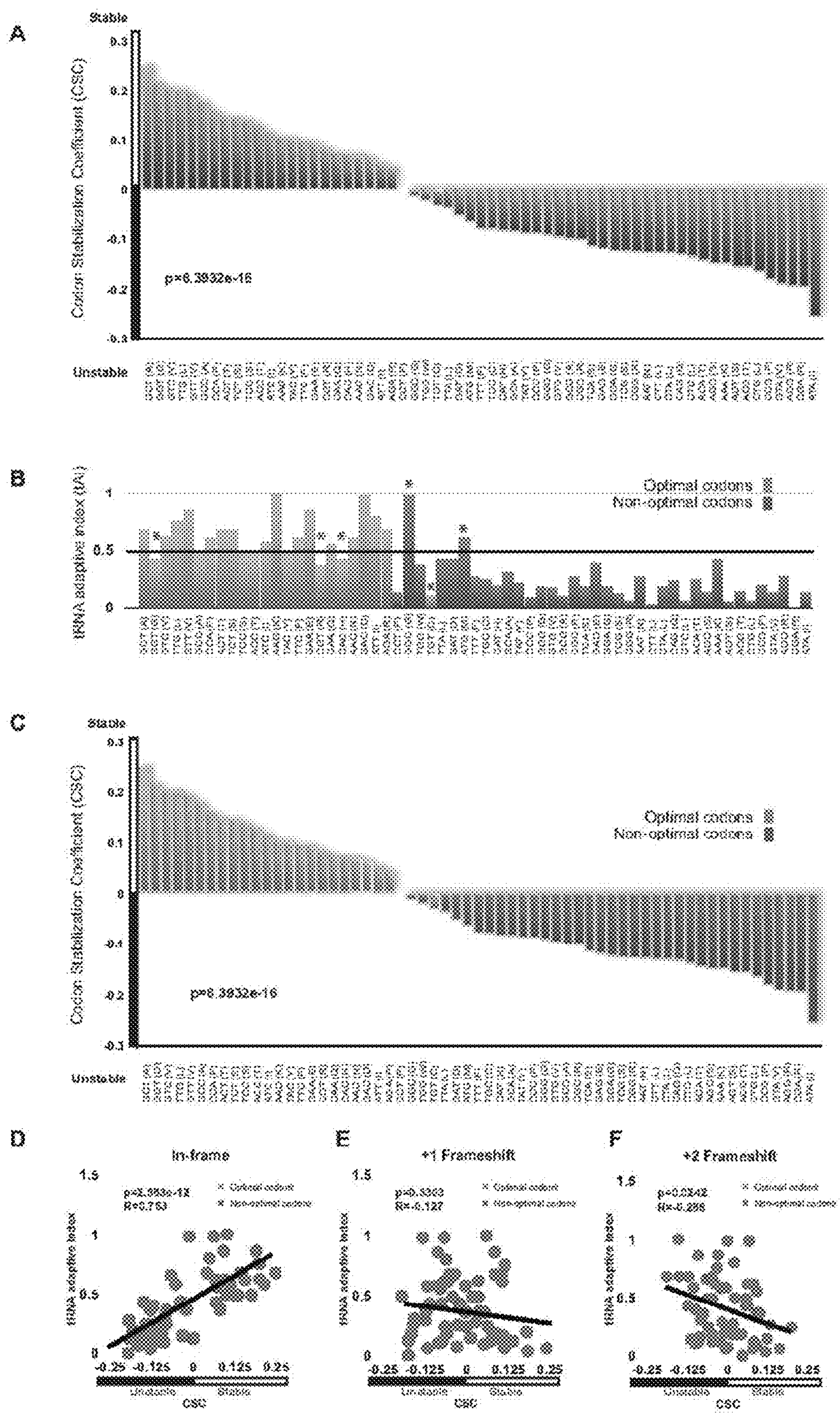
Figs. 2A-F

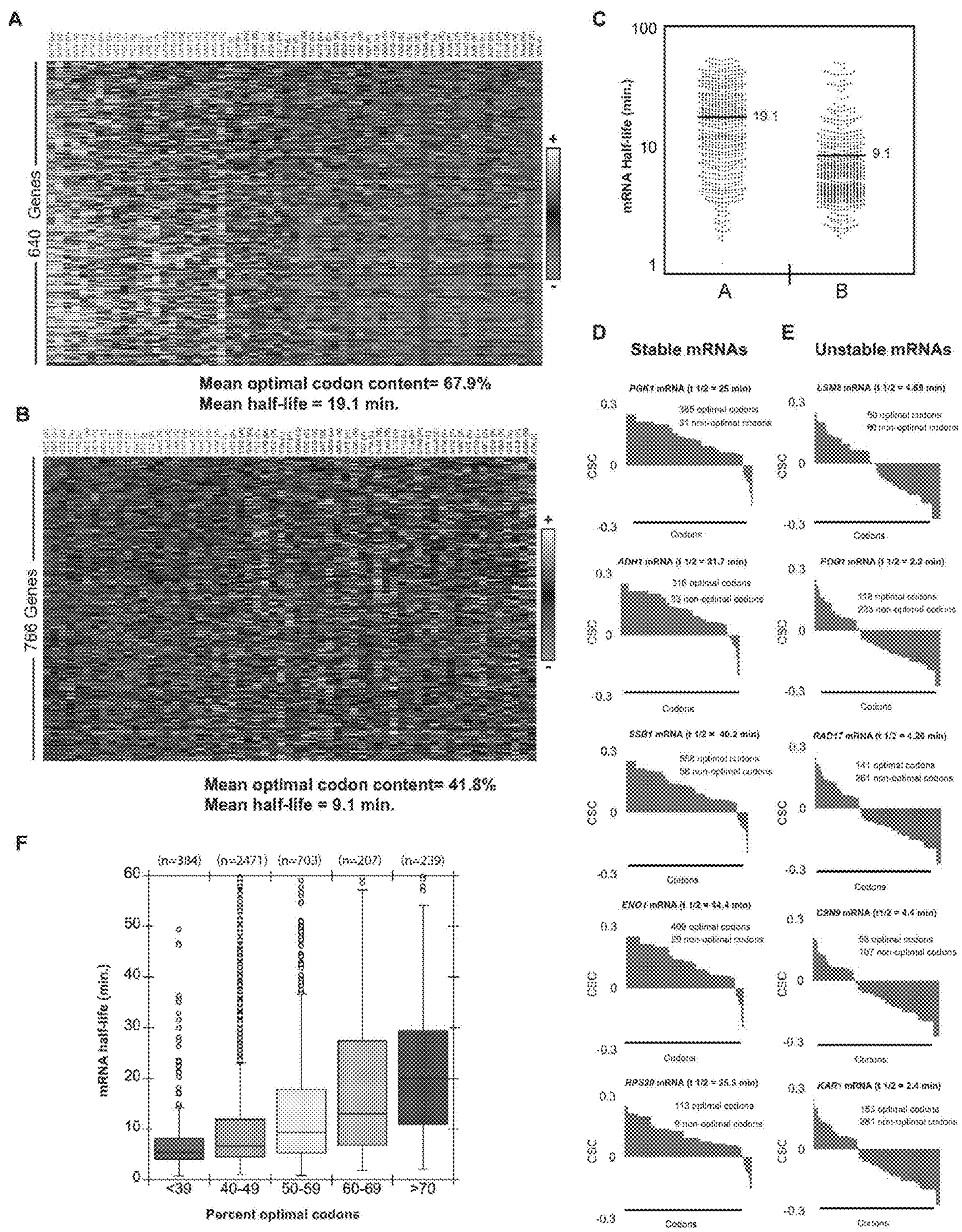
Figs. 3A-F

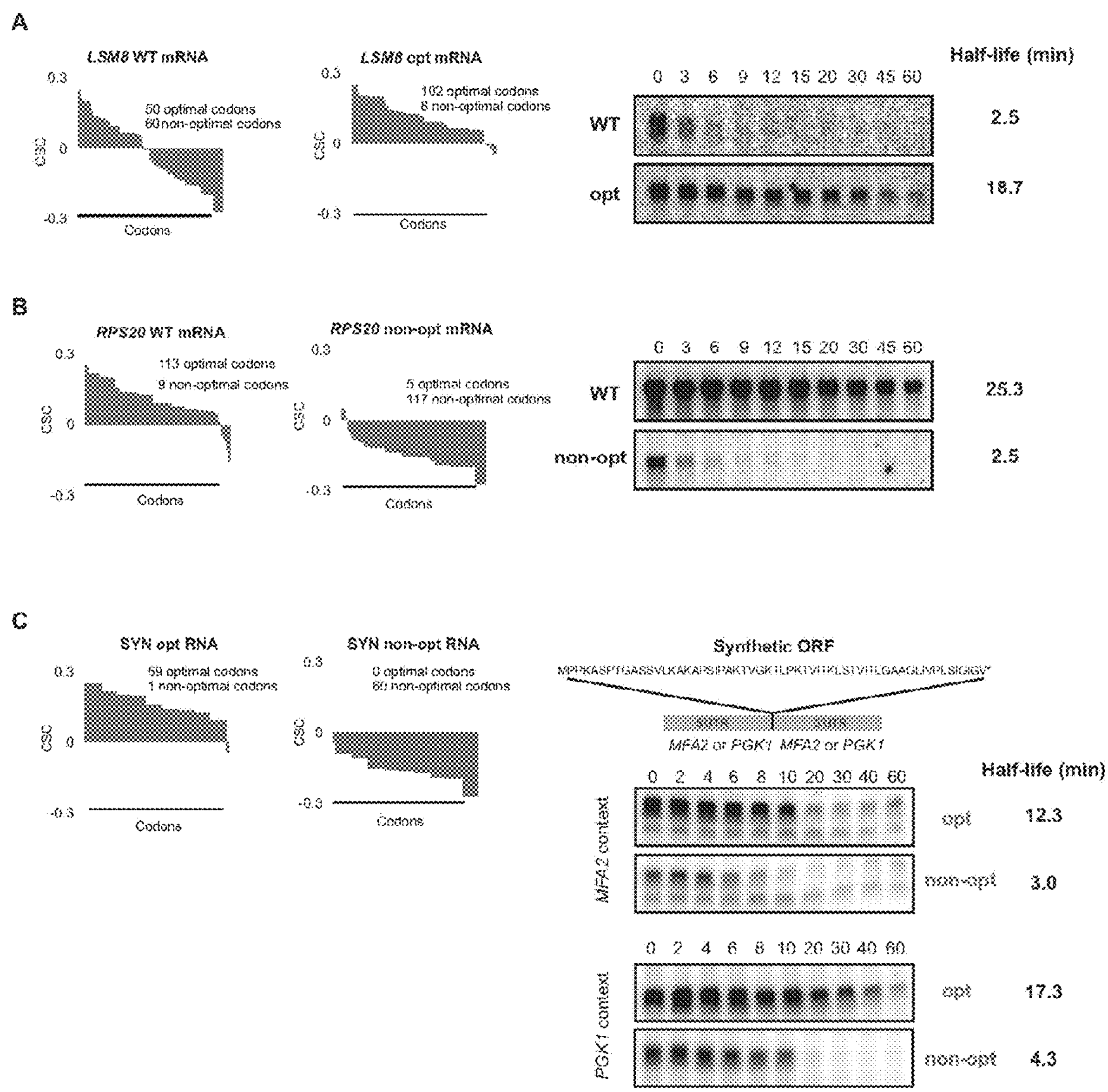
Figs. 4A-C

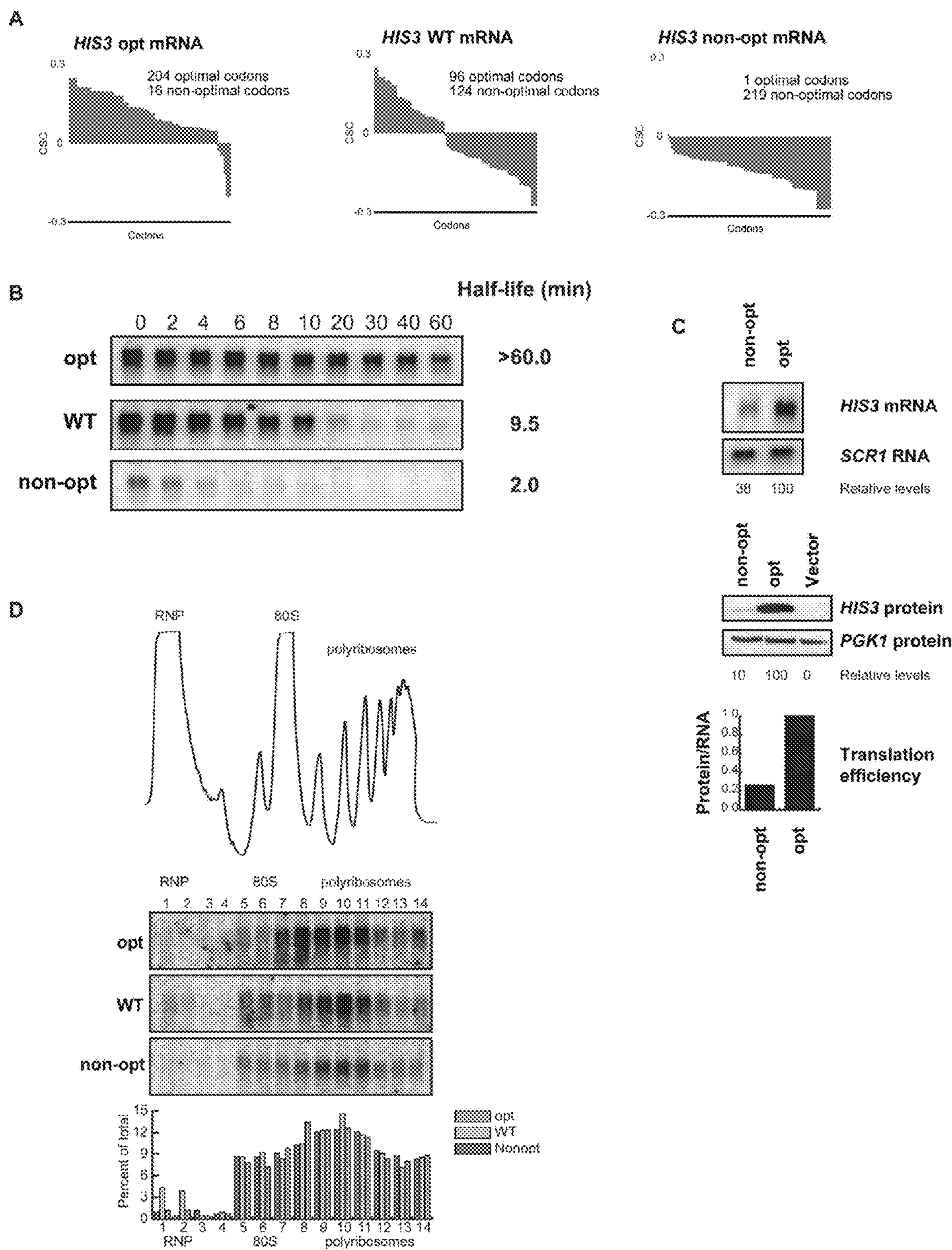
Figs. 5A-D

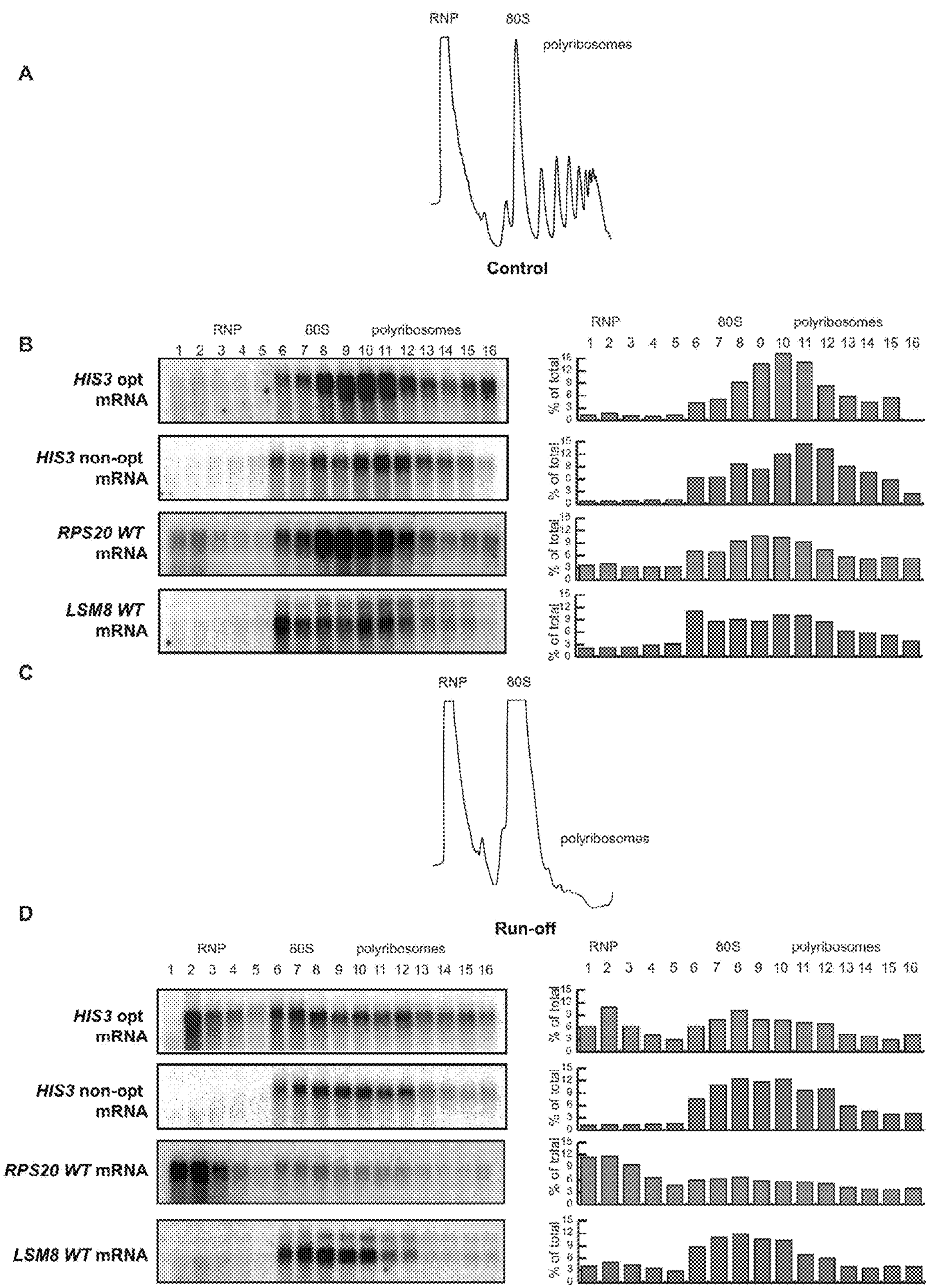
Figs. 6A-D

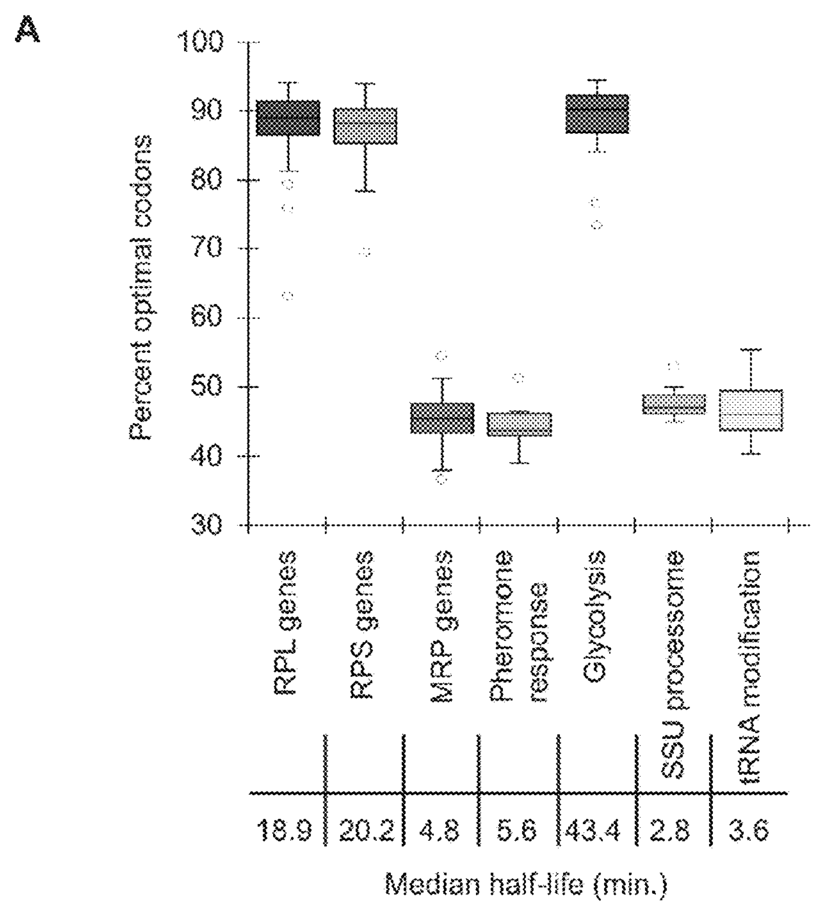
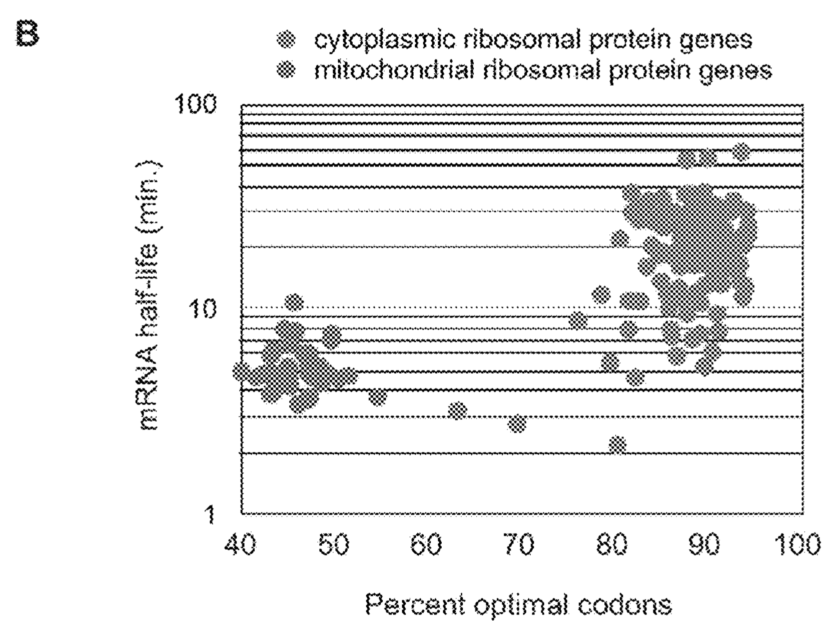
Figs. 7A-B

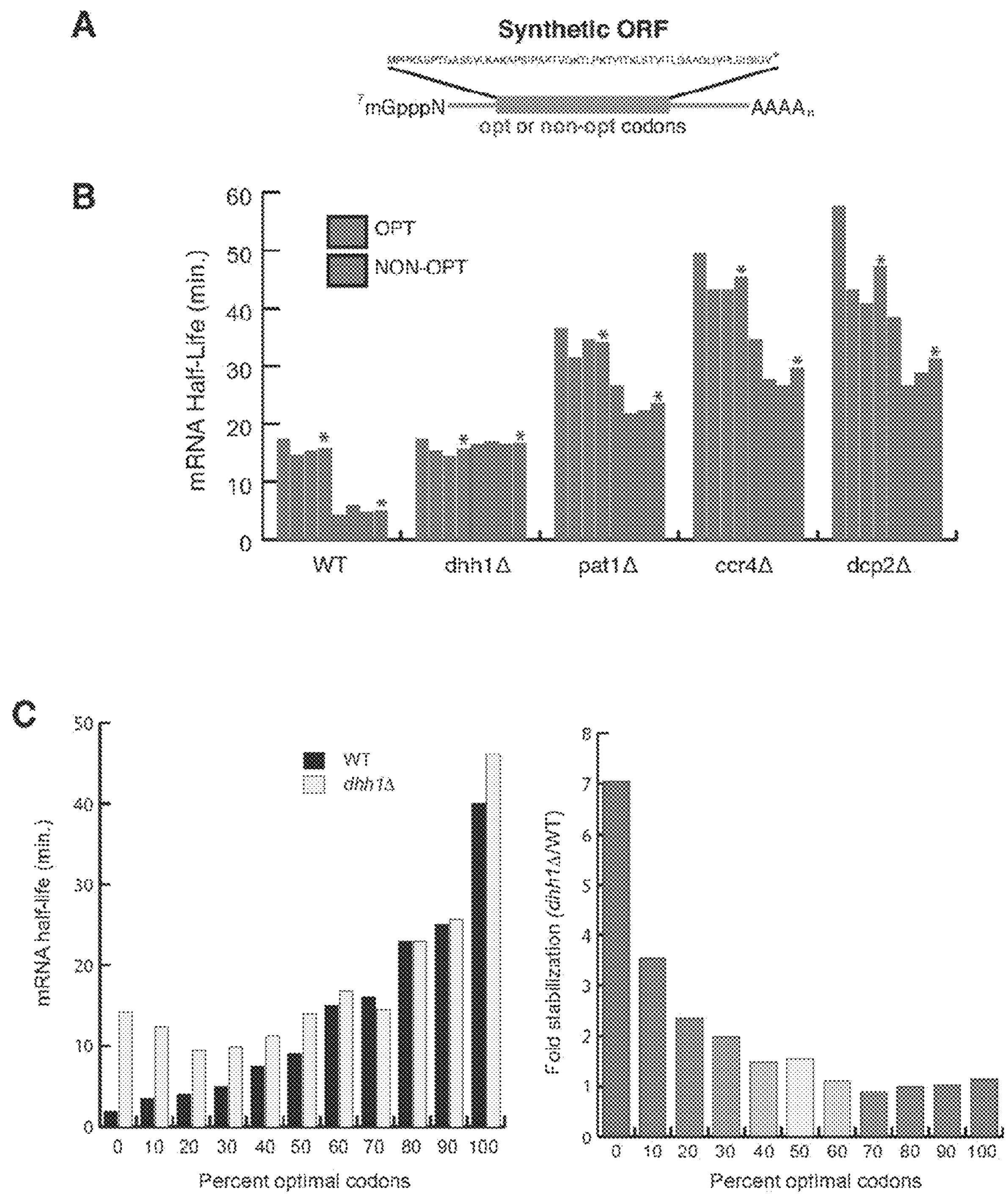
Fig. 9A-C

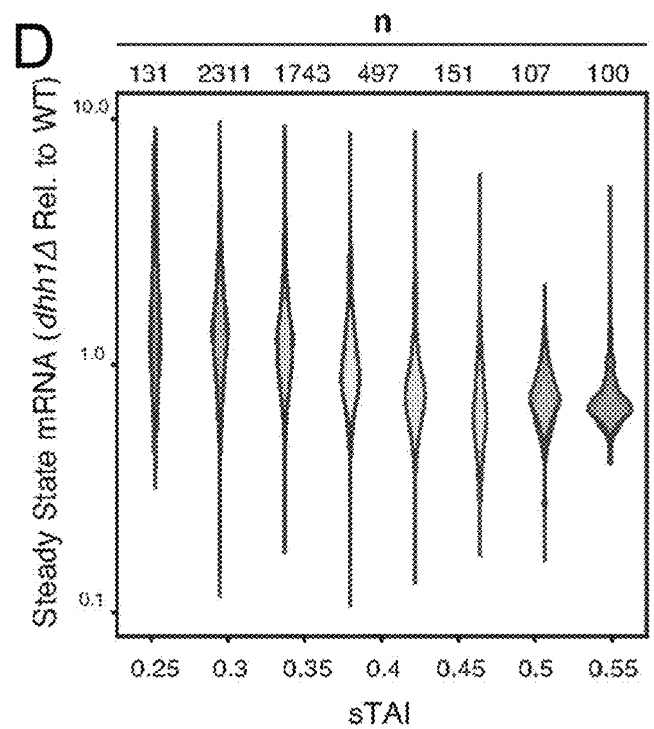
Fig. 9D
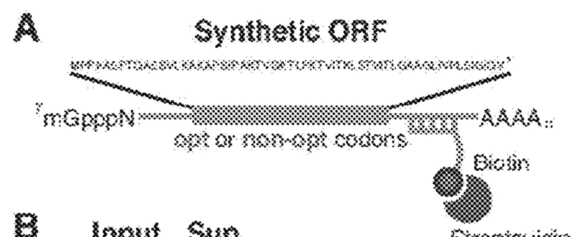
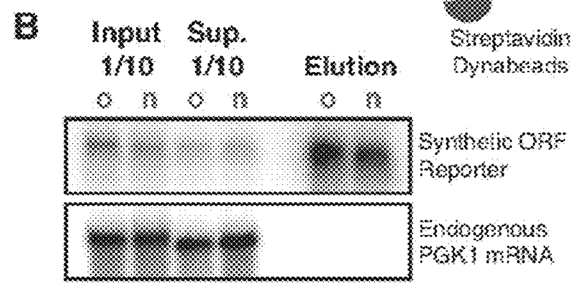
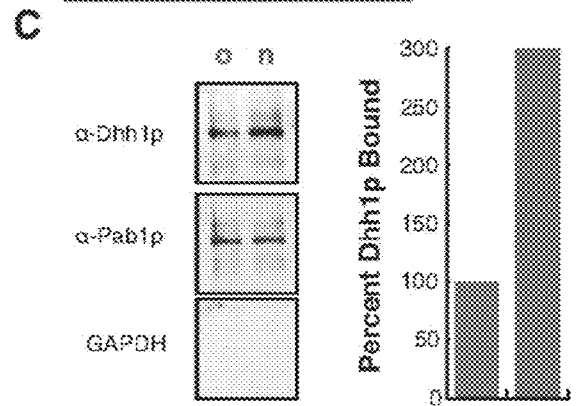
Figs. 10A-C

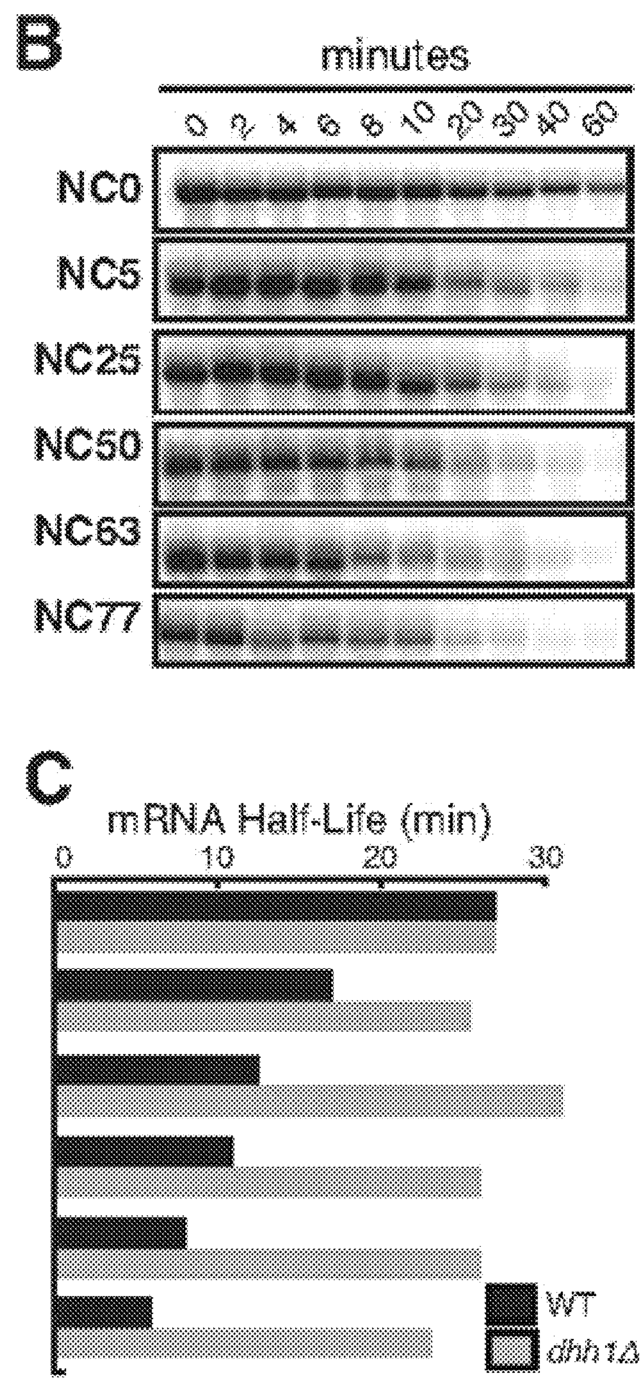
Figs. 11B-C

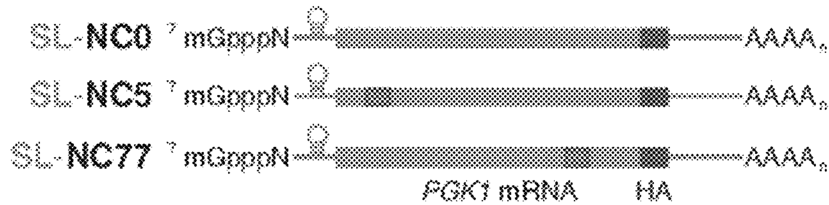
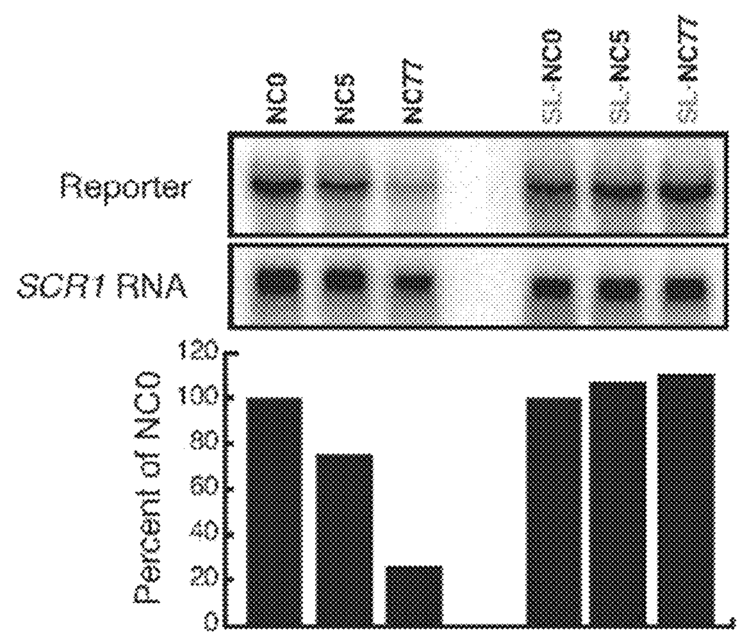
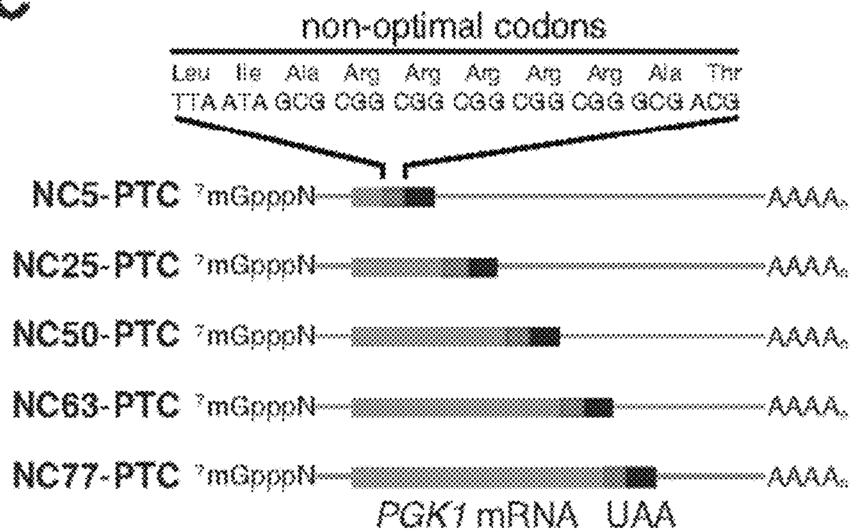
Figs. 12A-C

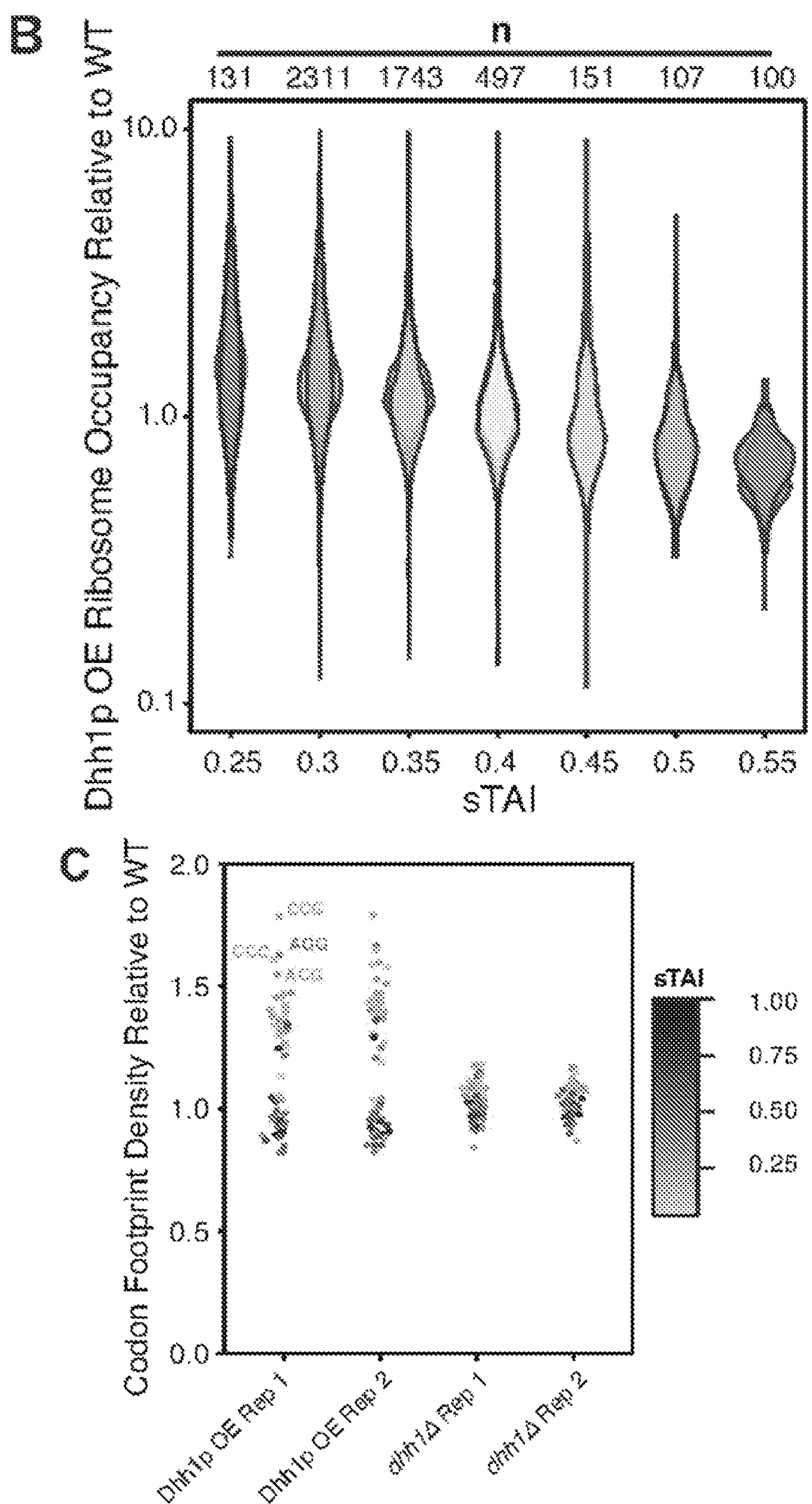
Figs. 13B-C

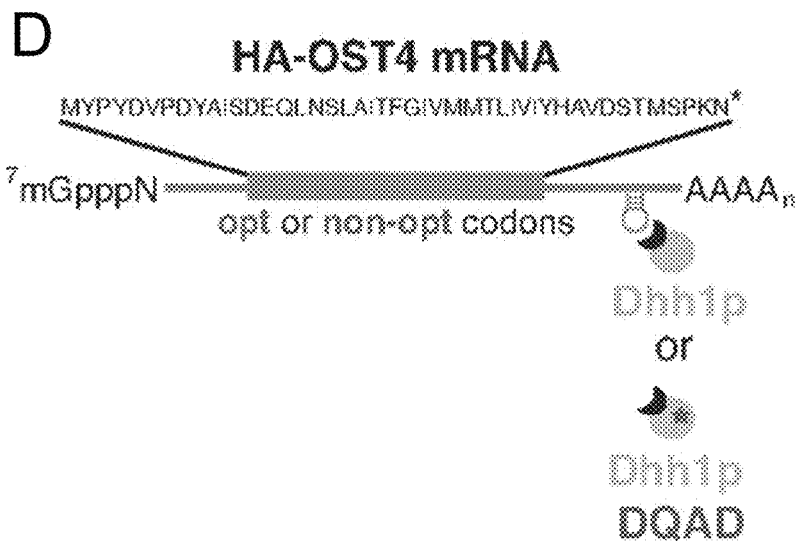
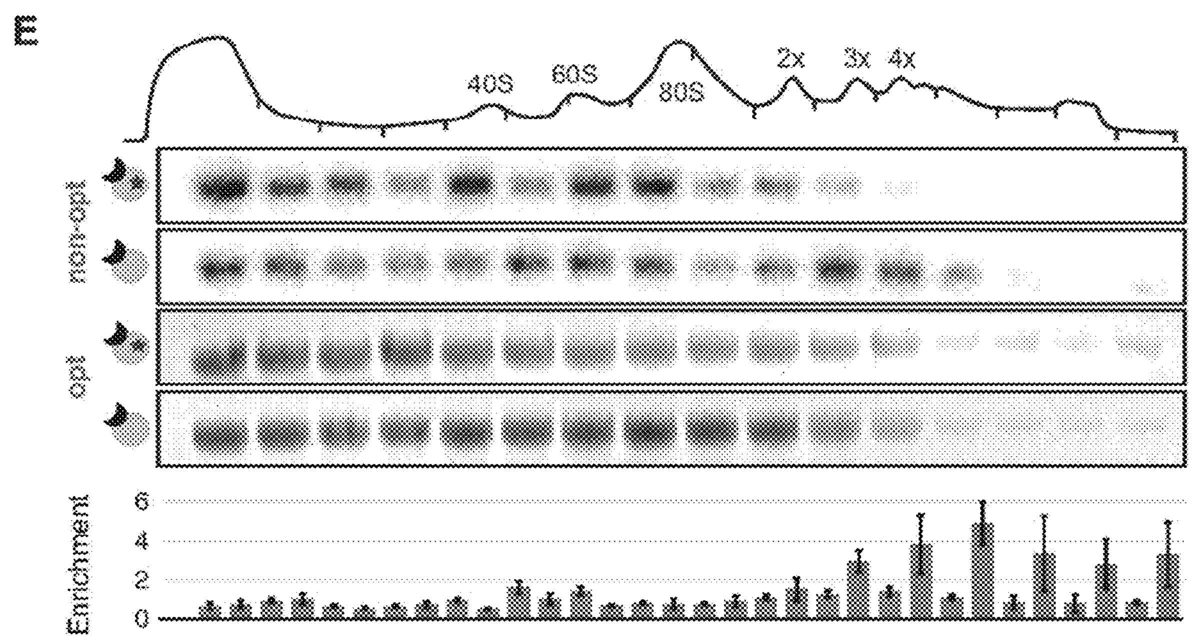
Figs. 13D-E

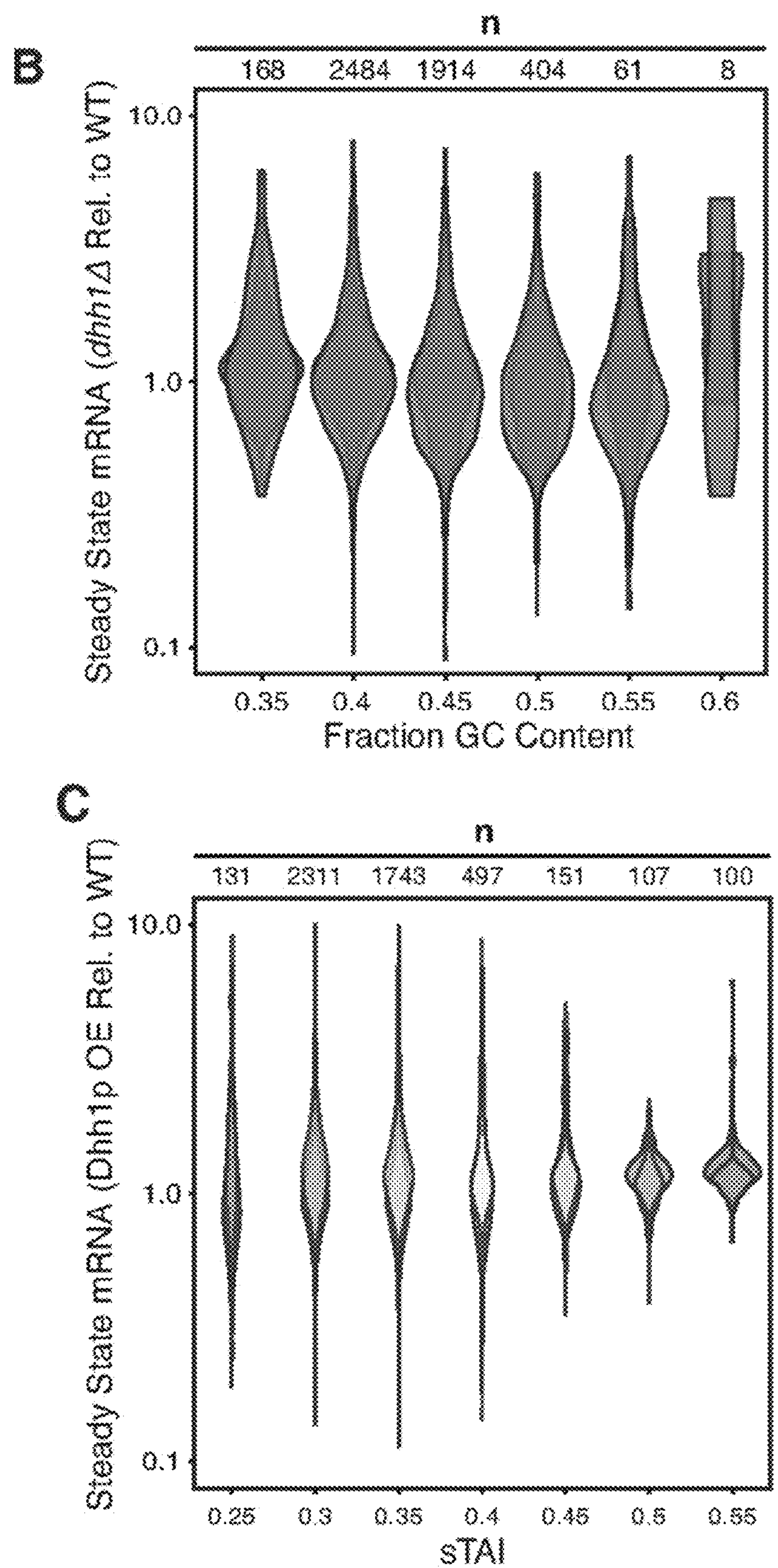
Figs. 16B-C

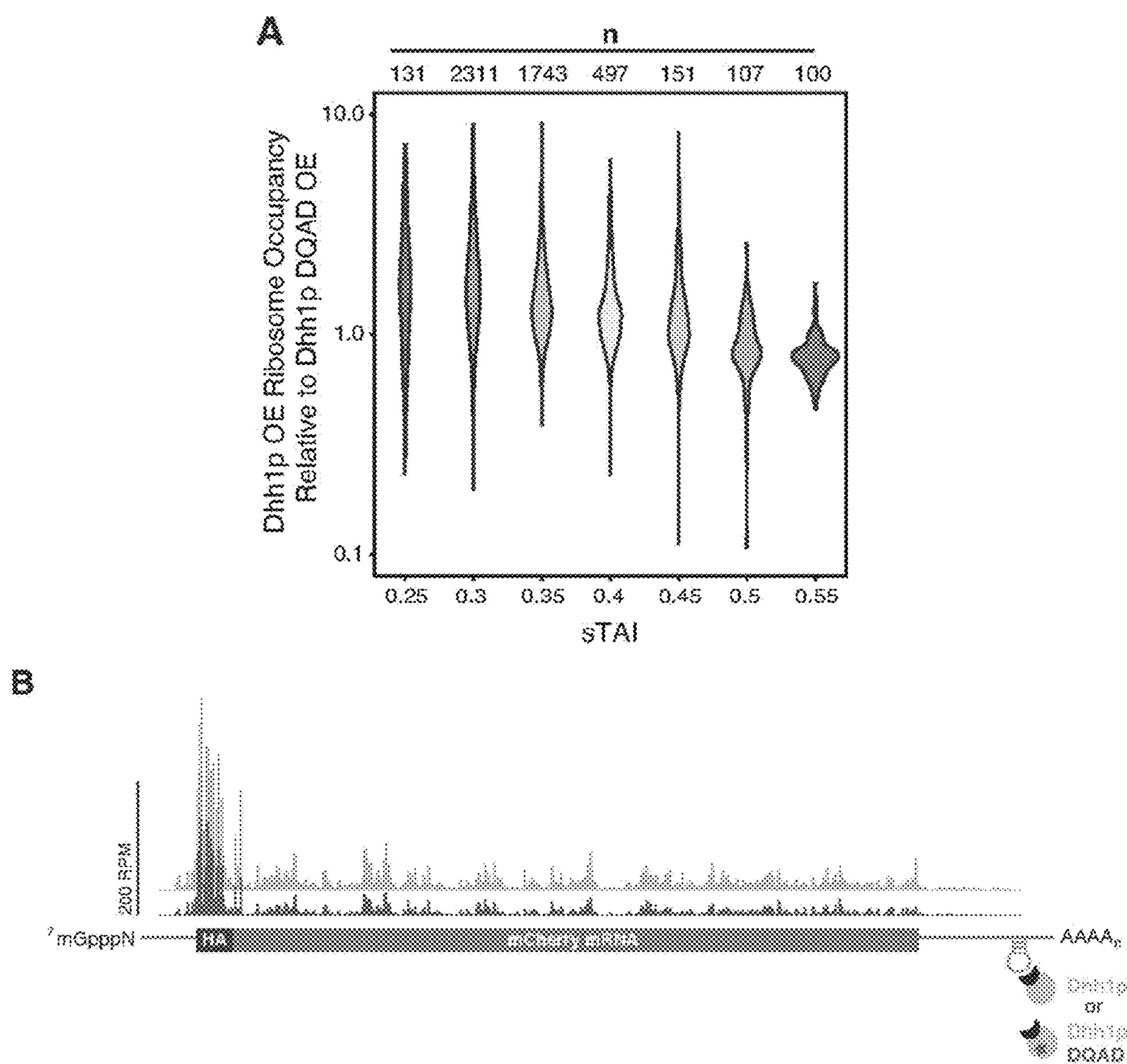
Figs. 18A-B

METHODS OF MODULATING MRNA STABILITY AND PROTEIN EXPRESSION

RELATED APPLICATION

This application is a Continuation-in-Part of U.S. application Ser. No. 15/557,412, filed Sep. 11, 2017, this application also claims priority to U.S. Provisional Application No. 62/398,281, filed Sep. 22, 2016, the subject matter of which are incorporated herein by reference in their entirety.

GOVERNMENT FUNDING

This invention was made with government support under Grant No. GM080465 awarded by The National Institute of Health. The United States government has certain rights to the invention.

BACKGROUND

All life forms use 61 codons to translate genetic information encoded within DNA (and RNA) into protein sequence. These codons are the "signals" used by the cell to dictate the accurate incorporation of individual amino acids (1 from a possible 20) into the growing polypeptide chain during the process of translation. Since there are 61 codons and only 20 amino acids, redundancy exists within the genetic code and the incorporation of a single amino acid can be dictated by more than one codon triplet (i.e., synonymous codons—different codon triplets directing the incorporation of the same amino acid into protein).

Messenger RNA (mRNA) degradation plays a role in regulating transcript levels in the cell and is a major control point for modulating gene expression. Degradation of most mRNAs in *Saccharomyces cerevisiae* is initiated by removal of the 3' poly(A) tail (deadenylation), followed by cleavage of the 5' 7mGpppN cap (decapping) and exonucleolytic degradation of the mRNA body in a 5'-3' direction. Despite being targeted by a common decay pathway, turnover rates for individual yeast mRNAs differ dramatically with half-lives ranging from <1 minute to 60 minutes or greater. RNA features that influence transcript stability have long been sought, and some sequence and/or structural elements located within 5' and 3' untranslated regions (UTRs) have been implicated in contributing to the decay of a subset of mRNAs. However, these features regulate mRNA stability predominantly in a transcript-specific manner through binding of regulatory factors and cannot account for the wide variation in half-lives observed across the entire transcriptome. Therefore, it seems likely that additional and more general features which act to modulate transcript stability could exist within mRNAs.

SUMMARY

Embodiments described herein relate to methods of modulating nucleic acid (e.g., mRNA) stability and protein expression by codon modification of wild type or native nucleic acids as well as to synthetic nucleic acids sequences formed by such codon modifications. In some embodiments, at least one optimal or non-optimal codon in a wild type mRNA sequence encoding a protein can be replaced respectively with one or more non-optimal codons or optimal codons encoding the same amino acid. The synthetic mRNA sequence with such modification(s) is capable of expressing the protein at a level that is at least about 10% different (e.g., greater or less) compared to that expressed by the wild type or native mRNA sequence in an in vitro mammalian cell culture system under identical conditions. The mRNA is degraded in a Dhh1p-dependent manner. The optimal codons are selected from the group consisting of get (Alanine), ggt (Glycine), gtc (Valine), ttg (Leucine), gtt (Valine), gcc (Alanine), cca (Proline), act (Threonine), tct (Serine), tcc (Serine), acc (Threonine), atc (Isoleucine), aag (Lysine), tac (Tyrosine), ttc (Phenylalanine), gaa (Glutamaic Acid), cgt (Arginine), caa (Glutamine), cac (Histidine), aac (Asparagine), gac (Aspartic Acid), att (Isoleucine), aga (Arginine), and tgt (Cysteine). The non-optimal codons are selected from the group consisting of cct (Proline), ggc (Glycine), tgg (Tryptophan), tta (Leucine), gat (Aspartic Acid), atg (Methionine), ttt (Phenylalanine), tgc (Cysteine), cat (Histidine), gca (Alanine), tat (Tyrosine), ccc (Proline), ggg (Glycine), gtg (Valine), gcg (Alanine), cgc (Arginine), tca (Serine), gag (Glutamaic Acid), gga (Glycine), tcg (Serine), cgg (Arginine), aat (Asparagine), ctt (Leucine), cta (Leucine), cag (Glutamine), ctc (Leucine), aca (Threonine), agc (Serine), aaa (Lysine), agt (Serine), acg (Threonine), ctg (Leucine), ccg (Proline), gta (Valine), agg (Arginine), cga (Arginine), and ata (Isoleucine).

In some embodiments, the synthetic mRNA sequence is capable of expressing the protein at a level which is at least about 20%, about 25%, about 30%, about 40%, about 50%, about 60%, about 70%, about 80%, about 90%, about 100%, or more different compared to that expressed by the wild type or native mRNA sequence in an in vitro mammalian cell culture system under identical conditions.

In some embodiments, one or more of the optimal codons of the wild type mRNA sequence can replaced with a non-optimal codon encoding the same amino acid as the replaced codon so that the synthetic mRNA sequence has less than about 50%, less than about 40%, less than about 30%, less than about 25%, less than about 20%, less than about 10%, or less than about 1% optimal codons. The replacement of the one or more optimal codons from the mRNA sequence with a non-optimal codon can decrease stabilization of the mRNA compared to the mRNA sequence prior to replacement.

In other embodiments one or more of the non-optimal codons is replaced with an optimal codon encoding the same amino acid as the replaced codon so that the synthetic mRNA sequence has more than about 50%, more than about 60%, more than about 70%, more than about 75%, more than about 80%, more than about 90%, more than about 95%, or more than about 99% about optimal codons. The replacement of the one or more non-optimal codons from the mRNA sequence with optimal codons can increase stabilization of the mRNA compared to the mRNA sequence prior to replacement.

Other embodiments relate to a method for preparing a synthetic mRNA encoding a protein expressed by a eukaryotic cell. The method can include identifying optimal and non-optimal codons in a mRNA encoding the protein, and replacing one or more of the optimal codons with a non-optimal codon encoding the same amino acid as the replaced codon or replacing one or more of the non-optimal codons with an optimal codon encoding the same amino acid. The mRNA is degraded in a Dhh1p-dependent manner. The replacement of the one or more codons from the mRNA encoding the protein can modulate expression of the protein in the eukaryotic cell at least about 10%, about 20%, about 25%, about 30%, about 40%, about 50%, about 60%, about 70%, about 80%, about 90%, about 100%, or more compared to that expressed by the mRNA prior to replacement in an in vitro mammalian cell culture system under identical conditions.

Still other embodiments described herein relate to a method of modulating the expression of a recombinant protein in a host cell. The method can include identifying optimal and non-optimal codons in an mRNA sequence that encodes the protein. One or more of the optimal codons can then be replaced with a non-optimal codon encoding the same amino acid as the replaced codon or one or more of the non-optimal codons can be replaced with an optimal codon encoding the same amino acid. The host cell can be transfected with the nucleic acid with the replaced codon. The mRNA is degraded in a Dhh1p-dependent manner. The replacement of the one or more codons from the mRNA sequence can modulates expression of the recombinant protein in the host cell at least about 10%, about 20%, about 25%, about 30%, about 40%, about 50%, about 60%, about 70%, about 80%, about 90%, about 100%, or more compared to the mRNA sequence prior to replacement.

In some embodiments, the replacement of the one or more codons from the mRNA sequence increases expression of the recombinant protein in the host cell at least about 10%, about 20%, about 25%, about 30%, about 40%, about 50%, about 60%, about 70%, about 80%, about 90%, about 100%, or more compared to the mRNA sequence prior to replacement.

In other embodiments, the replacement of the one or more codons from the mRNA sequence can decrease expression of the recombinant protein in the host cell at least about 10%, at least about 10%, about 20%, about 25%, about 30%, about 40%, about 50%, about 60%, about 70%, about 80%, about 90%, or more compared to the mRNA sequence prior to replacement.

BRIEF DESCRIPTION OF THE DRAWINGS

FIGS. 1(A-C) illustrate graphs showing mRNA half-lives calculated from poly(A)+vs total mRNA differ significantly. RNA-seq was performed on poly(A)+ and total RNA libraries prepared from rpb1-1 transcriptional shut-off experiments across a 60 minute time course. (A) All mRNAs with reliable half-lives in both libraries are plotted visually. Color intensity represents normalized mRNA remaining (time 0 is set to 100% for each mRNA). (B) Half-life of each mRNA plotted as calculated from total mRNA sequencing against the poly(A) sequencing. Data points with a >2 fold difference are highlighted in red. (C) Overview of the distribution of half-lives for both libraries.

FIGS. 2(A-F) illustrate plots showing that codon composition correlates with stability. (A) The Codon occurrence to mRNA Stability Correlation coefficient (CSC) plotted for each codon as calculated from the total RNA data set. The CSC is the R-value of the correlation between the occurrences of that codon and the half-lives of mRNA. Overall p-value is 6.3932e-16, permutation p-value is $<10^{-4}$. (B) tRNA Adaptability Index values for each codon plotted in the same order as (A). Codon optimality is coded, using light grey for optimal codons and dark grey for non-optimal codons. Codons designated with an asterisk (*) were called optimal or non-optimal according to additional criteria discussed therein. (C) The Codon occurrence to mRNA Stability Correlation coefficient (CSC) plotted for each codon as in (A), but optimality information presented in (B) is added by color-coding. Light grey color represents optimal codons and dark grey represents non-optimal. (D) tRNA Adaptive Index values plotted vs. CSC when ORFs are considered in-frame. Light grey indicates optimal codons, dark grey indicates non-optimal codons (R=0.7255, p-value is p-value=2.075e-09, permutation p-value $<10^{-4}$) (E) tRNA Adaptive Index values plotted vs. CSC when ORFs are frameshifted by one nucleotide. Green indicates optimal codons, red indicates non-optimal codons. (F) tRNA Adaptive Index values plotted vs. CSC when ORFs are frameshifted by two nucleotides. Light grey indicates optimal codons, dark grey indicates non-optimal codons.

FIGS. 3(A-F) illustrate heat maps (A) and graphs (B-E) showing that multiple codons are enriched in stable and unstable mRNA classes. (A) Heat map of a class of relatively stable mRNAs with similar codon usage. Each column represents the usage of a single codon, with each row representing one mRNA. (B) As (A), but showing a relatively unstable class of mRNAs. (C) Dot plot showing the distribution of half-lives in the mRNA classes shown in (A, B). (D) Codon optimality diagrams in selected stable mRNAs. Genes are broken down and plotted as individual codons. Codons are presented in order of optimality rather than in their natural order. Higher bars represent more optimal codons (CSC on y-axis). Light grey indicates optimal codons, dark grey indicates non-optimal codons. (E) Codon optimality diagrams in selected unstable mRNAs, as in (D). (F) Box plot of mRNAs half-lives separated into optimality groups. Half of the data fall within the boxed section, with the whiskers representing the rest of the data. Data points falling further than 1.5 fold the interquartile distance are considered outliers.

FIGS. 4(A-C) illustrate graphs and northern blots showing that the stability of mRNAs can be controlled by altering codon optimality. (A) Codon optimality diagram of LSM8 (as FIG. 3E), a naturally non-optimal mRNA shown. LSM8 OPT is a synonymously substituted version of LSM8 engineered for higher optimality. Northern blots of rpbl-1 shut-off experiments are shown on the right with half-life of both reporters. Quantitation is normalized to SCR1 loading controls not shown. (B) As (A), except a naturally optimal mRNA, RPS20 (as in Fig.3D), has been engineered for lower optimality as RPS20 non opt. Northern blots of rpbl-1 shut-off experiments are shown on the right with half-life of both messages. Quantitation is normalized to SCR1 loading controls not shown. (C) Codon optimality diagrams showing a synthetic mRNA (SYN) encoding the polypeptide (SEQ ID NO: 33) shown. Peptide is artificially engineered and has no similarity to any known proteins. SYN opt and non-opt were both inserted into flanking regions from a stable transcript (PGK1) and unstable transcript (MFA2). Northern blots on the right show GAL shut-off experiments demonstrating stability of the SYN mRNA in context of the MFA2 and PGK1 flanking sequences. Quantitation is normalized to SCR1 loading controls not shown.

FIGS. 5(A-D) illustrate graphs, plots, and northern blots showing that optimality can affect translation and stability of an mRNA without changes in ribosome association. (A) Codon optimality diagram of HIS3, a transcript with an intermediate half-life, as well as versions engineered with synonymous substitutions to contain higher and lower percent optimal codons, HIS3 opt and HIS3 non-opt respectively. (B) Northern blots of rpb1-1 shut-off experiments are shown with half-lives of all three messages. Quantitation is normalized to SCR1 loading controls not shown. (C) Northern and western blots for steady state concentrations of the optimal and non-optimal versions of HIS3. Loading controls and quantitation are shown below. Translational efficiency is calculated as relative protein levels divided by relative mRNA levels and plotted at the bottom. (D) A trace of sucrose density gradient analysis, along with northern blot analysis of the gradient fractions. The blots show location of the three HIS3 reporters within the gradient. Quantitation for each fraction is shown below.

FIGS. 6(A-D) illustrate plots, graphs, northern blots showing optimal and non-optimal transcripts are retained differently on polysomes. (A) Representative A260 trace of sucrose density gradient analysis demonstrating normal distribution into RNP, 80S, and polyribosome fractions. (B) Distribution of the optimal and non-optimal HIS3 reporters and the RPS20 and LSM8 mRNAs in the sucrose density gradients under normal conditions showing localization primarily in the polyribosome fractions. (C) Representative A260 trace of sucrose density gradient analysis under run-off conditions, showing collapse of the polyribosome fractions. (D) Distribution of the optimal and non-optimal HIS3 reporters and the RPS20 and LSM8 mRNAs under run-off conditions, demonstrating differential relocation.

FIGS. 7(A-B) illustrate graphs showing that functionally related genes display similar optimality. (A) Groups of genes whose protein products have related functions are plotted to show their optimality. Half of the data fall within the boxed section, with the whiskers representing the rest of the data. Data points falling further than 1.5 fold the interquartile distance are considered outliers. Represented gene groups are: 70 RPL (large ribosomal subunit proteins) genes, 54 RPS (small ribosomal subunit proteins) genes, 42 MRP (mitochondrial ribosomal proteins) genes, 14 pheromone response genes, 10 glycolysis enzymes, 15 SSU (small subunit processosome) genes, 12 tRNA processing genes. (B) Breakdown of two groups to show relationship between optimal codon content and halflife within the groups. mRNA half-life for each protein in the cytoplasmic ribosome and the mitochondrial ribosome is plotted against the optimal codon content of that mRNA.

FIGS. 9(A-D) illustrate that Dhh1p selectively stimulates the decay of mRNAs with low codon optimality. (A) Representation of the synthetic mRNAs (SYN) and the encoded polypeptide sequence (SEQ ID NO: 33). Optimal (opt) or non-optimal (non-opt) codons encoding the same peptide were used. The artificial peptide has no similarity to any known proteins. (B) The half-lives of SYN OPT and NON-OPT mRNAs in WT and different mutant strains were obtained from GAL1 shut-off experiments. Quantitations were normalized to the amount of SCR1 RNA. *Denotes average of 3 experiments. (C) Half-lives of reporters from FIG. 1B (GAL1 UAS constructs) in WT or dhh1Δ cells. Right panel indicates fold stabilization in a dhh1Δ cells vs. WT. (D) Quantifying steady state levels of mRNAs transcripts by RNA-Seq in dhh1Δ cells (RPKM) relative to WT cells (RPKM). mRNA transcripts are binned by sTAI, a numerical proxy for overall optimality. Shown are two biological replicates. A two-tailed Mann-Whitney test shows that low optimality mRNAs (sTAI, 0.25, Med.=1.52) are enriched relative to high optimality mRNAs (sTAI=0.55, Med.=0.72) upon Dhh1p depletion, U=1668, p<2.2×10-16.

FIGS. 18(A-B) illustrates that Dhh1p modulates ribosome occupancy on mRNAs with low codon optimality. (A) Plotting the ribosome occupancy (average number of ribosomes per mRNA transcript) for mRNA transcripts under constitutive Dhh1p OE relative to constitutive Dhh1p-DQAD OE, binning transcripts by sTAI. Shown are two biological replicates. A two-tailed Mann-Whitney test shows that low optimality mRNAs (sTAI=0.25, Med.=1.53) have increased ribosome occupancy relative to high optimality mRNAs (sTAI=0.55, Med.=0.71), U=685, p<2.2×10-16 upon catalytically active Dhh1p overexpression relative to catalytically inactive Dhh1p overexpression. (B) Ribosome occupancy along a reporter HA-mCherry mRNA upon tethering catalytically active and inactive Dhh1p.

DETAILED DESCRIPTION

Figure 8A:
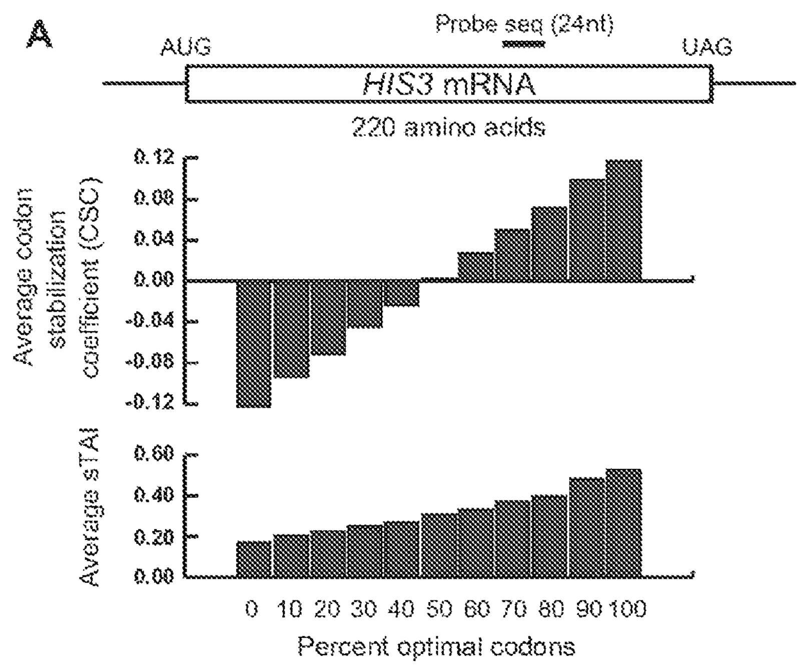
FIGS. 8(A-C) illustrate graphs and Northern blots showing that codon optimality is a powerful determinate of mRNA stability. (A) Representation of the HIS3 mRNA reporter. Each reporter encodes the exact same polypeptide sequence, but is comprised of different codon composition of varying optimality. The average codon stabilization coefficient (CSC) and species specific tRNA adaptation index (sTAI) for each construct is shown. (B) Northern blots of the HIS3 reporter series following transcriptional shut-off in a rpb1-1 strain (left panel). The right panel shows the same reporters recloned with the GAL1 inducible promoter. Shown are Northern blots following transcriptional inhibition with glucose. (C) Graphs the half-lives of the mRNA reporters in panel B.

Methods involving conventional molecular biology techniques are described herein. Such techniques are generally known in the art and are described in detail in methodology treatises, such as *Current Protocols in Molecular Biology*, ed. Ausubel et al., Greene Publishing and Wiley-Interscience, New York, 1992 (with periodic updates). Unless otherwise defined, all technical terms used herein have the same meaning as commonly understood by one of ordinary skill in the art to which the present application pertains. Commonly understood definitions of molecular biology terms can be found in, for example, Lodish et al., *Molecular Cell Biology*, 6th Edition, W. H. Freeman: New York, 2007, and Lewin, *Genes IX*, Jones and Bartlett Publishers: Mass., 2008. For convenience, certain terms employed in the specification, examples, and appended claims are collected here.

As used herein, "one or more of a, b, and c" means a, b, c, ab, ac, bc, or abc. The use of "or" herein is the inclusive or.

As used herein, "protein" is a polymer consisting of the 20 amino acids. Although "polypeptide" is often used in reference to relatively large polypeptides, and "peptide" is often used in reference to small polypeptides, usage of these terms in the art overlaps and is varied.

The terms "polynucleotide sequence", "nucleic acid sequence", and "nucleotide sequence" are also used interchangeably herein.

"Recombinant," as used herein, means that a protein is derived from a prokaryotic or eukaryotic expression system.

The term "wild type" refers to the naturally-occurring polynucleotide sequence encoding a protein, or a portion thereof, or protein sequence, or portion thereof, respectively, as it normally exists in vivo.

As used herein, the term "nucleic acid" refers to polynucleotides, such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

As used herein, the term "gene" or "recombinant gene" refers to a nucleic acid comprising an open reading frame encoding a polypeptide, including both exon and (optionally) intron sequences.

As used herein, the term "vector" refers to a nucleic acid molecule capable of transporting another nucleic acid to which it has been linked. Preferred vectors are those capable of one or more of, autonomous replication and expression of nucleic acids to which they are linked. Vectors capable of directing the expression of genes to which they are operatively linked are referred to herein as “expression vectors”.

A polynucleotide sequence (DNA, RNA) is “operatively linked” to an expression control sequence when the expression control sequence controls and regulates the transcription and translation of that polynucleotide sequence. The term “operatively linked” includes having an appropriate start signal (e.g., ATG) in front of the polynucleotide sequence to be expressed, and maintaining the correct reading frame to permit expression of the polynucleotide sequence under the control of the expression control sequence, and production of the desired polypeptide encoded by the polynucleotide sequence.

“RNA transcript” refers to the product resulting from RNA polymerase-catalyzed transcription of a DNA sequence. When the RNA transcript is a perfect complimentary copy of the DNA sequence, it is referred to as the primary transcript or it may be a RNA sequence derived from post-transcriptional processing of the primary transcript and is referred to as the mature RNA. “Messenger RNA” or “mRNA” refers to the RNA that is without introns and that can be translated into protein by the cell. “cDNA” refers to a double-stranded DNA that is complementary to, and derived from, mRNA. “Sense” RNA refers to RNA transcript that includes the mRNA and so can be translated into protein by the cell. “Antisense RNA” refers to a RNA transcript that is complementary to all or part of a target primary transcript or mRNA and that blocks the expression of a target gene (U.S. Pat. No. 5,107,065; WO 99/28508). The complementarity of an antisense RNA may be with any part of the specific gene transcript, i.e., at the 5' non-coding sequence, 3' non-coding sequence, or the coding sequence. “Functional RNA” refers to antisense RNA, ribozyme RNA, or other RNA that is not translated and yet has an effect on cellular processes. The term “operably linked” refers to the association of nucleic acid sequences on a single nucleic acid fragment so that the function of one is affected by the other. For example, a promoter is operably linked with a coding sequence when it is capable of affecting the expression of that coding sequence (i.e., the coding sequence is under the transcriptional control of the promoter). Coding sequences can be operably linked to regulatory sequences in sense or antisense orientation.

The term “expression”, as used herein, refers to the transcription and stable accumulation of sense (mRNA) or antisense RNA derived from the nucleic acid fragment(s) of the invention. Expression may also refer to translation of mRNA into a polypeptide.

“Transcriptional regulatory sequence” is a generic term used throughout the specification to refer to nucleic acid sequences, such as initiation signals, enhancers, and promoters, which induce or control transcription of protein coding sequences with which they are operably linked. In some examples, transcription of a recombinant gene is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences, which control transcription of the naturally occurring form of a protein.

“Homology” and “identity” are used synonymously throughout and refer to sequence similarity between two peptides or between two nucleic acid molecules. Homology can be determined by comparing a position in each sequence, which may be aligned for purposes of comparison. When a position in the compared sequence is occupied by the same base or amino acid, then the molecules are homologous or identical at that position. A degree of homology or identity between sequences is a function of the number of matching or homologous positions shared by the sequences.

The term “isolated” as used herein with respect to nucleic acids, such as DNA or RNA, refers to molecules separated from other DNAs, or RNAs, respectively, which are present in the natural source of the macromolecule. The term isolated as used herein also refers to a nucleic acid or peptide that is substantially free of cellular material or culture medium when produced by recombinant DNA techniques, or chemical precursors or other chemicals when chemically synthesized. Moreover, an “isolated nucleic acid” is meant to include nucleic acid fragments, which are not naturally occurring as fragments and would not be found in the natural state.

As used herein, the term “in vitro” refers to an artificial environment and to processes or reactions that occur within an artificial environment. In vitro environments consist of, but are not limited to, test tubes and cell culture. The term “in vivo” refers to the natural environment (e.g., an animal or a cell) and to processes or reaction that occur within a natural environment.

As used herein, the term “synthetic” as used herein can be in reference to a nucleotide sequence (or nucleic acid molecule comprising a synthetic nucleotide sequence), the term “synthetic” refers to a sequence that is designed (e.g., in silico), for example, for the purpose of expressing an encoded polypeptide of interest. The term “synthetic nucleotide” also includes the product of the manufacture of a nucleic acid molecule by means of chemically synthesized oligonucleotides by in vitro or in vivo methodologies known to those skilled in the art of gene synthesis, or by combinations of in vitro or in vivo methods.

As used herein, the term “mammalian” refers to any mammal, including a human being.

Embodiments described herein relate to methods of modulating nucleic acid stability and protein expression by codon modification of wild type or native nucleic acids encoding proteins or open reading frames or protein coding regions of nucleic acid sequences as well as to synthetic nucleic acids sequences formed by such codon modifications.

It was found that synonymous codon triplets are not recognized by cells identically and that mRNAs enriched in triplets which are deemed ‘optimal’ (see below) are translated more efficiently, have greater stability, and express higher protein levels than mRNA counterparts which lack optimal codons. Codon optimality represents an established scale that reflects the balance between the supply of charged tRNA molecules for a particular codon in the cytoplasmic pool and the demand imposed by the codon as it is read by the translating ribosomes. Codon optimality, therefore, represents a measure of translation efficiency and mRNAs enriched in optimal codons are decoded faster and more accurately by the ribosome than non-optimal codons which slow translation elongation. Not only does codon optimality modulate translation elongation rate, but it also dramatically impacts mRNA stability and protein output from that mRNA template. Codon optimality therefore impinges greatly on gene expression by modulating the level of protein product both through impacting mRNA decay and translational elongation rates. Substitution of optimal codons with synonymous, non-optimal codons results in dramatic mRNA destabilization and slowed translational elongation, while the converse substitution significantly increases stability and protein synthesis. Advantageously, the substitution of codons in mRNA protein coding regions and the consequential impact on gene expression does not alter the identity of the polypeptide/protein product.

It has been further shown that DEAD-box helicase Dhh1p is a sensor of codon optimality that targets an mRNA for decay and that mRNAs whose translation elongation rate is slowed by inclusion of non-optimal codons are specifically degraded in a Dhh1p-dependent manner. Without being bound by theory, it is believed that Dhh1p dynamically samples elongation events, binding to the translating mRNAs (and ribosomes along it) when elongation is slow. It is further believed that Dhh1p's association with the translating mRNP may slow ribosome movement even further, leading ultimately to activation of mRNA decapping and degradation.

In accordance with embodiments described herein, transcript-specific translation elongation rate, as dictated by codon triplet usage, can be predictably manipulated to achieve a vast array of mRNA stabilities and protein levels. Since codon optimality is achieved through tRNA concentrations, cellular tRNA levels and or tRNA modifications can be modulated to predictably alter mRNA and protein abundance. Manipulation of codon usage can be used for protein engineering and large-scale protein expression as well as a means to achieve desired therapeutic effects by altering protein expression levels without altering protein sequence.

Optimal and non-optimal codons as defined herein were designated by determining if mRNAs enriched in any individual codon demonstrated greater or lesser stability. For purposes of this application, mRNAs were defined as stable if they have a half-life greater than 2-fold longer than the average (e.g., about 20 minutes), and unstable if they have a half-life less than half of the average (e.g., about 5 min). For each codon, a correlation between the frequency of occurrence of that codon in mRNAs and the stabilities of the mRNAs was calculated. Occurrences of a codon were compared to the half-life for each mRNA and a Pearson correlation calculation was used to generate an R-value. This metric is referred to as the Codon occurrence to mRNA Stability Correlation coefficient (CSC). The CSC values for all codons were then compared to each other (FIG. 2A). Strikingly, it was observed that some codons preferentially occurred in stable mRNAs while others occurred preferentially in unstable mRNAs (overall p-value=1.496e-14, permutation p-value $<10^{-4}$). For example, the GCT alanine codon was highly enriched in stable transcripts as defined by RNA-seq analysis, while its synonymous codons, GCG and GCA were preferentially present in unstable transcripts (FIG. 2A). Approximately one-third of all codon triplets were over-represented in stable mRNAs, while the remaining two-thirds appeared to predominate in unstable mRNAs.

Optimal codons include get (Alanine), ggt (Glycine), gtc (Valine), ttg (Leucine), gtt (Valine), gcc (Alanine), cca (Proline), act (Threonine), tct (Serine), tcc (Serine), acc (Threonine), atc (Isoleucine), aag (Lysine), tac (Tyrosine), ttc (Phenylalanine), gaa (Glutamaic Acid), cgt (Arginine), caa (Glutamine), cac (Histidine), aac (Asparagine), gac (Aspartic Acid), att (Isoleucine), aga (Arginine), and tgt (Cysteine).

Non-optimal codons include cct (Proline), ggc (Glycine), tgg (Tryptophan), tta (Leucine), gat (Aspartic Acid), atg (Methionine), ttt (Phenylalanine), tgc (Cysteine), cat (Histidine), gca (Alanine), tat (Tyrosine), ccc (Proline), ggg (Glycine), gtg (Valine), gcg (Alanine), cgc (Arginine), tca (Serine), gag (Glutamaic Acid), gga (Glycine), tcg (Serine), cgg (Arginine), aat (Asparagine), ctt (Leucine), cta (Leucine), cag (Glutamine), ctc (Leucine), aca (Threonine), agc (Serine), aaa (Lysine), agt (Serine), acg (Threonine), ctg (Leucine), ccg (Proline), gta (Valine), agg (Arginine), cga (Arginine), and ata (Isoleucine).

In some embodiments, at least one optimal or non-optimal codon in a wild type or native nucleic acid sequence encoding a protein can be synonymously substituted or replaced respectively with one or more non-optimal codons or optimal codons encoding the same amino acid. As used herein, the term "synonymously substituted" refers to the replacement or substitution of one or more codons from a nucleic acid sequence with one or more synonymous codons. "Synonymous codons" refers to same-sense codons that do not alter the identity of the recombinant protein produced by a host cell. For example, UUU and UUC code for the same amino acid-phenylalanine. Most of the time, if the third nucleotide is the one with the mutation, it will result in coding for the same amino acid. This is called a synonymous mutation because, like a synonym in grammar, the mutated codon has the same meaning as the original codon and therefore does not change the amino acid.

In some embodiments, the synthetic nucleic acid sequence can be RNA, such as mRNA or in vitro transcribed mRNA, or DNA, such as cDNA. The synthetic nucleic sequence, such as RNA or DNA, can be provided in an RNA or DNA expression vector.

In other embodiments, the synthetic nucleic acid sequence can be ligated into an expression vector. A host cell can then be transfected with the expression vector. The transfected host cell can be cultured in a suitable culture media appropriate for the expression of a protein and the protein can be isolated.

For example, as shown in the graph of FIG. 2C, optimal or non-optimal codons in a nucleic acid sequence of interest can be identified. Next, one or more codons can be replaced with optimal or non-optimal synonymous codon(s) in the polynucleotide sequence of interest. The substituted polynucleotide sequence can then be inserted in a vector prior to transfection of a host cell in order to increase or decrease heterologous expression of a recombinant protein in host cell.

In some embodiments, the synthetic nucleic acid sequence with such modification(s) is capable of expressing the protein at a level that is at least about 10%, about 20%, about 25%, about 30%, about 40%, about 50%, about 60%, about 70%, about 80%, about 90%, about 100%, or more different (e.g., greater or less) compared to that expressed by the wild type nucleic acid sequence in an in vitro mammalian cell culture system under identical conditions.

The stability of mRNA with the replaced codons is directly proportional to the percentages of replaced optimal codons or non-optimal codons. It was demonstrated in Example 3 below that the DEAD-box helicase Dhh1p is a critical factor in distinguishing between mRNAs containing optimal and non-optimal codons and targeting them for decay. It was observed that Dhhp1 is preferentially associated with mRNAs with suboptimal codon choice and that Dhhp1 is a sensor for ribosome speed thereby targeting an mRNA for repression and subsequent decay. Therefore, in certain embodiments, the percentages of optimal codons replaced with non-optimal codons are directly proportional to the decrease of mRNA stability through increased Dhh1p-dependent mRNA degradation.

In some embodiments, one or more of the optimal codons of the wild type nucleic acid sequence can replaced with a non-optimal codon encoding the same amino acid as the replaced codon so that the synthetic nucleic acid sequence has less than about 50%, less than about 40%, less than about 30%, less than about 25%, less than about 20%, less than about 10%, or less than about 1% optimal codons. The replacement of the one or more optimal codons from the nucleic acid sequence with a non-optimal codon can decrease stabilization of mRNA transcribed from the nucleic acid sequence compared to the nucleic acid sequence prior to replacement.

In other embodiments one or more of the non-optimal codons is replaced with an optimal codon encoding the same amino acid as the replaced codon so that the synthetic nucleic acid sequence has more than about 50%, more than about 60%, more than about 70%, more than about 75%, more than about 80%, more than about 90%, more than about 95%, or more than about 99% about optimal codons. The replacement of the one or more non-optimal codons from the nucleic acid sequence with optimal codons can increase stabilization of mRNA transcribed from the nucleic acid sequence compared to the nucleic acid sequence prior to replacement.

As discussed above, substitution of optimal codons with synonymous, non-optimal codons results in dramatic mRNA destabilization, while the converse substitution significantly increases stability. Therefore, in some embodiments, the optimization of a nucleic sequence for heterologous expression in a host cell increases stabilization of mRNA transcribed from the optimized polynucleotide sequence compared to the original polynucleotide sequence. In other embodiments, the optimization of a nucleic sequence for heterologous expression in a host cell decreases stabilization of mRNA transcribed from the optimized polynucleotide sequence compared to the original polynucleotide sequence.

The optimized nucleic acids described herein may be recombinantly expressed by molecular cloning into an expression vector containing a suitable promoter and other appropriate transcription regulatory elements, and transferred into eukaryotic host cells to produce a recombinant protein of interest. Techniques for such manipulations are described in the art (Sambrook et al. Molecular Cloning: A Laboratory Manual; Cold Spring Harbor Laboratory Press, Cold Spring Harbor, N.Y., (1989); Current Protocols in Molecular Biology, Ausubel et al., Green Pub. Associates and Wiley-Interscience, New York (1988); Yeast Genetics: A Laboratory Course Manual, Rose et al., Cold Spring Harbor Laboratory, Cold Spring Harbor, N.Y., (1990), which are hereby incorporated by reference in their entirety).

Host cells for use in the preparation of heterologous recombinant proteins in a method described herein can include but are not limited to eukaryotic cells typically used in large-scale protein expression. Exemplary eukaryotic cells include but are not limited to yeast cells and mammalian cells. Yeast cells can include yeast is selected from the group consisting of: *Saccharomyces cerevisiae, Hansenula polymorpha, Pichia pastoris, Kluyvermyces fragilis, Kluveromyces lactis*, and *Schizosaccharomyces pombe*. Mammalian cells can include but are not limited to Chinese Hamster Ovary cells (CHO) cells, Human Embryonic Retinoblast (HER) cells, and Human Embryonic Kidney (HEK) cells. In some particular embodiments, the eukaryotic cell host is a yeast cell or a Chinese Hamster Ovary (CHO) cell.

Other embodiments relate to a method for preparing a synthetic nucleic acid encoding a protein expressed by a eukaryotic cell. The method can include identifying optimal and non-optimal codons in a nucleic acid encoding the protein, and replacing one or more of the optimal codons with a non-optimal codon encoding the same amino acid as the replaced codon or replacing one or more of the non-optimal codons with an optimal codon encoding the same amino acid. The replacement of the one or more codons from the nucleic acid encoding the protein can modulate expression of the protein in the eukaryotic cell at least about 10%, about 20%, about 25%, about 30%, about 40%, about 50%, about 60%, about 70%, about 80%, about 90%, about 100%, or more compared to that expressed by the nucleic acid prior to replacement in an in vitro mammalian cell culture system under identical conditions.

Still other embodiments described herein relate to a method of modulating the expression of a recombinant protein in a host cell. The method can include identifying optimal and non-optimal codons in a nucleic acid sequence that encodes the protein. One or more of the optimal codons can then be replaced with a non-optimal codon encoding the same amino acid as the replaced codon or one or more of the non-optimal codons can be replaced with an optimal codon encoding the same amino acid. The host cell can be transfected with the nucleic acid with the replaced codon. The replacement of the one or more codons from the nucleic acid sequence can modulates expression of the recombinant protein in the host cell at least about 10%, about 20%, about 25%, about 30%, about 40%, about 50%, about 60%, about 70%, about 80%, about 90%, about 100%, or more compared to the nucleic acid sequence prior to replacement.

In some embodiments, the replacement of the one or more codons from the nucleic acid sequence increases expression of the recombinant protein in the host cell at least about 10%, about 20%, about 25%, about 30%, about 40%, about 50%, about 60%, about 70%, about 80%, about 90%, about 100%, or more compared to the nucleic acid sequence prior to replacement. The replacement of the one or more codons from the nucleic acid sequence can increase stabilization of mRNA transcribed from the nucleic acid sequence compared to the nucleic acid sequence prior to replacement.

In other embodiments, the replacement of the one or more codons from the nucleic acid sequence can decrease expression of the recombinant protein in the host cell at least about 10%, at least about 10%, about 20%, about 25%, about 30%, about 40%, about 50%, about 60%, about 70%, about 80%, about 90%, or more compared to the nucleic acid sequence prior to replacement. The replacement of the one or more codons from the nucleic acid sequence can decreases stabilization of mRNA transcribed from the nucleic acid sequence compared to the nucleic acid sequence prior to replacement.

In one exemplary embodiment, LSM8, a naturally occurring non-optimal mRNA can be synonymously substituted with one or more codons for greater optimality and heterologous expression (see FIG. 3E). In some embodiments, a naturally occurring mRNA can be synonymously substituted with one or more codons for lower optimality. In one exemplary embodiment, RPS20, a naturally occurring mRNA can be synonymously substituted with one or more codons for lower optimality resulting in a lower mRNA expression of RPS20 in yeast cells (see FIG. 3D).

Codon optimization methods described herein can be applied to any life science research area, allowing biologists to systematically enhance or reduce the expression of recombinant genes in a heterologous host organism.

In some embodiments, methods of the application can be used in large-scale protein expression. For example, methods of the present application can be used to manipulate codon optimality in order to produce more or less of a gene of interest for creating drugs, treating disease, etc. Well known molecular biology techniques can be applied to manipulate a polynucleotide encoding a gene to contain ideal codons and obtain the gene expression pattern that is most beneficial to a given application.

In certain embodiments, methods of the present disclosure can be used to enhance the expression of foreign genes in commonly used microbial cell factories such as *Saccharomyces cerevisiae* and *Pichia pastoris*. Therefore, the methods of the present disclosure can be used in any industry where it is desirable to improve the production of heterologous proteins in a particular host organism. As such, the methods of the present disclosure can be integrated into biopharmaceutical processes to improve the production of therapeutic protein drugs.

In some embodiments, methods of the present disclosure can be used to produce Human Recombinant insulin in *Saccharomyces cerevisiae* yeast cells. For example, a human proinsulin polynucleotide sequence can be optimized as described above prior to inclusion of the polynucleotide into a recombinant plasmid and subsequent transformation into a yeast host cell resulting in an increase of insulin protein expression by the host yeast cells.

In addition, in cases where metabolic engineering of cells is required, the methods of the present disclosure can be used to enhance the expression of the respective metabolic enzymes to alter biosynthetic pathways for biotechnological applications which can include biofuel production, biocatalysis and bioremediation.

For example, Glucoamylase enzymes for saccharification can be used on liquefied starch-containing substrates to produce sugars which in turn serve as a feedstock for biological fermentations in the industrial production of ethanol. Therefore, in some embodiments, codon optimization methods of the present disclosure can be used to enhance the expression of glucoamylase enzymes in yeast. Therefore, of nucleic acid sequences encoding glucoamylase can allow for increased glucoamylase enzyme output and thus increase the production yield of ethanol.

Synthetic nucleic acids optimized in accordance with a method of the present disclosure can include nucleic acids encoding structurally related glucoamylase enzymes, SGA1, STA2 and STA1.

In some embodiments, an optimized synthetic nucleic acid produced in accordance with a method of the present disclosure encodes a sporulation-specific glucoamylase (SGA1) enzyme. Exemplary optimized SGA1 nucleic acid sequences include cDNA sequences having SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ NO:9, and SEQ ID NO:10.

In another embodiment, an optimized synthetic nucleic acid produced in accordance with a method of the present disclosure encodes a STA2 glucoamylase enzyme. Exemplary optimized STA2 nucleic acid sequences include cDNA sequences having SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, and SEQ ID NO:22.

In another embodiment, an optimized synthetic nucleic acid produced in accordance with a method of the present disclosure encodes a STA1 glucoamylase enzyme. Exemplary optimized STA1 nucleic acid sequences include cDNA sequences having SEQ ID NO:23, SEQ ID NO:24. SEQ ID NO:25, SEQ ID NO:26, SEQ ID NO:27, SEQ ID NO:28, SEQ ID NO:29, SEQ ID NO:30, SEQ ID NO:31, and SEQ ID NO:32.

In certain embodiments, the heterologous protein of interest expressed in a host cell is an antibody. Chinese Hamster Ovary cells (CHO) are commonly used for expression of recombinant proteins, including monoclonal antibodies. CHO cells are the predominant host used to produce therapeutic proteins. About 70% of all recombinant proteins produced today are made in CHO cells, including DUXB11, DG44 and CHOK1 lineages. The ability to grow to high density in serum-free suspension culture conditions, as well as to express and secrete proteins with the appropriate post-translational modifications (e.g., glycosylation), make CHO cells suitable for production of many antibodies or proteins intended for human therapeutic applications. Therefore, it is further contemplated that recombinant CHO cells transfected with an optimized polynucleotide sequence encoding high-, moderate- or low-expression genes described above can successfully grow in large-scale cultures of either adherent cells or suspension-adapted cells.

The present invention also relates to recombinant vectors and recombinant host cells, both prokaryotic and eukaryotic, which contain the optimized or non-optimized codon substituted nucleic acid molecules disclosed throughout this specification. In some embodiments, a stable cell line capable of heterologous expression in a host cell comprising an optimized polynucleotide described above is provided. The process for development of a stable cell line starts with expression vector construction and transfection. After being transfected with plasmids bearing for example, optimized polynucleotides encoding antibody light and heavy chain genes, as well as selectable marker or markers, cells can be screened for high productivity following growth recovery, serum-free suspension adaptation and amplification (if necessary) and clone selection.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Codon Optimality is a Major Determinate of mRNA Stability

In this Example, we show that codon optimality has a broad and powerful influence on mRNA stability in eukaryotic cells, such as yeast cells. First, global analysis of RNA decay rates reveals that mRNA half-life correlates with optimal codon content. Many stable mRNAs demonstrate a strong preference towards the inclusion of optimal codons within their coding regions, while many unstable mRNAs harbor non-optimal codons. Second, we demonstrate that substitution of optimal codons with synonymous, non-optimal codons results in a dramatic destabilization of the mRNA and that the converse replacement leads to a significant increase in mRNA stability. Third, we experimentally demonstrate an impact of codon optimality on ribosome translocation indicating that the effect on mRNA decay occurs through modulation of mRNA translation elongation. These findings indicate that transcript-specific translation elongation rate, as dictated by codon usage, is an important determinant of mRNA stability. Fourth, we observe tightly coordinated optimal codon content in genes encoding proteins with common physiological function. We hypothesize that this finding explains the previously observed similarity in mRNA decay rates for these gene families. Taken together, our data suggest that there is evolutionary pressure on protein coding regions to coordinate gene expression at the level of protein synthesis and mRNA decay.

Ribosomes are the Master Gatekeepers, Determining the Downstream Fate of Both Normal and Aberrant mRNAs As a final implication, our work suggests that co-translational mRNA surveillance by the ribosome is not only important to target aberrant mRNAs to rapid decay, but also to tune the degradation rates of normal mRNAs. In eukaryotes, aberrations in mRNAs lead to aberrant translation events such as premature termination, lack of translation termination, and ribosome stalling, which result in the accelerated turnover of the mRNA by the Nonsense-Mediated, Non Stop, and No-Go Decay pathways, respectively (Shoemaker and Green, 2012). We find here that codon usage within normal mRNAs also influences translating ribosomes and can have profound effects on mRNA stability.

Thus, the ribosome acts as the master sensor, helping to determine the fate of all mRNAs, both normal and aberrant, through modulation of its elongation and/or termination processes. The use of the ribosome as a sensor is ideal for protein-coding genes, whose primary function in the cell is to be translated. We suggest that a component of mRNA stability is built into all mRNAs as a function of codon composition. The elongation rate of translating ribosomes is communicated to the general decay machinery, which affects the rate of deadenylation and decapping. Individually, the identity of codons within an mRNA would be predicted to have a minute influence on overall ribosomal decoding; however, within the framework of an entire mRNA, we show that codon optimality can have profound effects on translation elongation and mRNA turnover. We therefore conclude that codon identity represents a general property of mRNAs and is a critical determinant of their stability.

Experimental Procedures

Yeast Strains and Growth Conditions

Unless indicated, all strains are based on BY4741. Cells were grown in standard synthetic medium (pH 6.5) supplemented with appropriate amino acids and sugars. All cells were grown at 24° C. and collected at midlog phase ($3\times10^7$ cells $ml-^1$).

Plasmids and Strain Construction

Reporter plasmids bearing native genes (LSM8, RPS20, HIS3 WT) were constructed by amplifying the native loci, adding restriction sites and several unique sites (to facilitate detection by northern probe) in the 3' UTR by site-directed mutagenesis, and inserting the construct into an expression vector. The reporters with altered optimality (LSM8 opt, RPS20 nonopt, HIS3 opt & non-opt) were constructed by synthesizing the DNA in multiple pieces, annealing and amplifying them, and then subcloning into an expression vector. These reporter plasmids were transformed into an rpb1-1 yeast strain. To construct the plasmids bearing the synthetic reporters, restriction sites were introduced into previously constructed plasmids bearing MFA2 and PGK1 under the control of a GAL1 UAS. The SYN ORFs were then synthesized and assembled as described for the altered reporters above. These reporters were transformed into a WT yeast strain.

Northern RNA Analysis and Sucrose Density Gradients

Northern RNA analysis of GAL-driven reporters and sucrose density gradients for polyribosome analysis was performed as previously described (Hu et al, 2009). For analysis of reporters in rpb1-1 was performed similarly to GAL, except cells were grown in media containing glucose and repression was achieved by shifting cells to 37° C. Ribosomal run-off experiments were performed similarly to normal polyribosome analysis, except cells were resuspended in media lacking glucose for 10 minutes before harvesting (Coller and Parker, 2005).

RNA-Seq rpb1-1 mutant cells (Nonet et al, 1987) were grown to mid-log phase at 24° C. and shifted to a non-permissive temperature of 37° C. Aliquots were collected over 60 minutes. RNA was then extracted, external controls were added, and two sets libraries were prepared from each using the Illumina TruSeq Stranded Total RNA and mRNA library prep kits. The libraries were quantitated using an Agilent Bioanalyzer and sequenced on an Illumina HiSeq2000 using paired-end 100 bp reads with an index read. Sequencing data and the processed data for each gene are available at the Gene Expression Omnibus (www.ncbi.nlm.nih.gov/geo) under accession number GSE57385.

Alignment and Half-Life Calculation

Reads were aligned to the *S. cerevisiae* reference genome using bowtie (Langmead et al., 2009), with the unaligned reads then aligned to the sequences of the controls in the same way. Aligned reads were quantitated using cufflinks (Trapnell et al., 2010). Raw FPKM numbers were normalized to external controls, then fitted to single exponential decay curves to calculate the half-lives using the least absolute deviation method to minimize outlier effects. Data was then filtered to exclude dubious ORFs and transcripts with poor fit to the model. Bootstrapped confidence intervals were generated by using un-normalized residuals from the original data to generate simulated data sets.

Statistical Methods

The Codon occurrence to mRNA Stability Correlation coefficient (CSC) was determined by calculating a Pearson correlation coefficient between the frequency of occurrence of individual codons and the half-lives of the messages containing them. To determine the statistical significance, we categorized the CSC as either positive or negative and used a chi-squared test of association. For association between the categories of percent optimal codons and mRNA half-life, an ANOVA f-test with mRNA half-life on the log scale was used. To mitigate effects of base pair content of the genes, we randomly permuted the sequence and recalculated the test statistic for each of 10,000 permutations. The permutation p-value was calculated as the number of permuted data sets with a test of association stronger than the chi squared test in the original data. Statistical calculations were done using the R environment. Optimality percentages were calculated by generating a list of optimal and non-optimal codons as previously described (Pechmann and Frydman, 2013).

Plasmids and Strain Construction

The plasmids and oligonucleotides used in this study are listed in Supplementary Tables 3 and 4 respectively.

LSM8 & RPS20 reporters: To construct the base reporter plasmids bearing LSM8 (pJC663) and RPS20 (pJC666), DNA was amplified from the LSM8 locus with oJC2357/oJC2358 and from the RPS20 locus with oJC2366/oJC2367. Restriction sites were inserted by site-directed mutagenesis to facilitate further cloning. XhoI sites were introduced directly upstream of the start codon in both using oJC2415/oJC2416 and oJC2417/oJC2418 respectively. SphI sites were introduced directly downstream of the stop codon using oJC2431/oJC2432 and oJC2433/oJC2434. Several point mutations were introduced into the 3' UTRs to facilitate detection using oJC2435/oJC2436 and oJC2437/oJC2438 respectively. These were then cloned into pJC69 (Gietz and Sugino, 1988) to create pJC663, 666. The optimality-inverted plasmids (pJC667, 668 respectively) were constructed by synthesizing the ORF in two parts by annealing oJC2421/oJC2422 and amplifying with oJC2423/oJC2424 for LSM8 and annealing oJC2427/oJC2428 and amplifying with oJC2427/oJC2428 for RPS20. These inserts were cloned back into the XhoI/SphI sites of pJC663, 666. These reporters were transformed into yJC244 to make yJC1888-91.

SYN reporters: To construct the plasmids bearing the synthetic reporters, restriction sites were introduced directly before the start codon and after the stop codon of a PGK1-bearing plasmid (pJC296) as well as an MFA2-bearing plasmid (pJC312). Both of these plasmids are under the control of a GAL1 UAS. SpeI and XhoI sites were inserted into pJC296, using oJC2377/oJC2378 and oJC2379/oJC2380 respectively. XbaI and XhoI sites were introduced into pJC312, using oJC2381/oJC2382 and oJC2383/oJC2384 respectively. The SYN-opt sequence was synthesized as two complementary oligonucleotides (oJC2385/oJC2409), then annealed and digested with SpeI/XhoI, then ligated into similarly digested plasmids prepared as above to make the SYN-opt reporters with PGK1 context (pJC672) and MFA2 context (pJC674). The SYNnonopt oligonucleotides (oJC2386/oJC2410) were processed identically to generate the SYN-nonopt reporter with PGK1 context (pJC673) and MFA2 context (pJC675). These reporters were transformed into yJC151 to make yJC1892-95.

HIS3 reporters: For the HIS3 reporters, the endogenous reporter (pJC712) was made by amplifying the URA3 selectable marker from pJC390 with oJC2508/2509 and inserting it into the cloning site of pJC387, which already contained the HIS3 ORF under the control of its native promoter. This was transformed into yJC151 to make yJC2031 and into yJC1883 to make yJC2033. The non-optimal ORF was synthesized by annealing 4 oligonucleotides (oJC2500-3), then amplifying with oJC2518/oJC2519, and replacing the existing ORF of the pJC387 plasmid using PacI/AscI to make pJC710. Selectable marker URA3 was then added as described above to make pJC711. This was transformed into yJC151 to make yJC2030 and into yJC1883 to make yJC2032. The optimal ORF was constructed by annealing 4 oligonucleotides (oJC2605-8), amplifying with pJC2611/2612, and then replacing the ORF of pJC711 using PacI/AscI to make pJC716. This was transformed into yJC151 to make yJC2088 and into yJC244 to make yJC2090. FLAG-tagged versions were produced by introducing the FLAG tag via site-directed mutagenesis into pJC711 using oligonucleotides oJC2620/2621 to make pJC719 and into pJC716 using oligonucleotides oJC2622/2623 to make pJC720. These were transformed into yJC151 to make yJC2135 and yJC2137 respectively. All of the HIS3 constructs were designed to retain a short invariant region in the ORF (positions 337-359), which was used for detection by northern oligonucleotide probe oJC2564.

Northern RNA Analysis

Northern RNA analysis was performed essentially as previously described (Hu et al., 2009). Briefly, for analysis of the SYN reporters, cells carrying the SYN reporters were grown in 2% galactose, 1% sucrose synthetic media and collected at mid-log phase. Transcription repression was achieved by resuspending collected cells in media containing 4% glucose. After transcriptional repression, cell aliquots were removed, total RNA was isolated by (30 mg) was analyzed by electrophoresis through 1.4% formaldehyde agarose gel or 6% denaturing polyacrylamide gel. For analysis of LSM8, RPS20, and HIS3 reporters, rpb1-1 shut-offs were performed as described below in the first paragraph of the RNA-seq section, then loaded onto 1.4% formaldehyde agarose gels instead of library construction and following steps.

Northern analyses were performed using oligonucleotide radiolabelled with T4 PNK. Specifically, the LSM8 reporters were detected using oJC2450, RPS20 with oJC2451, HIS3 with oJC2564, and SYN RNAs with oJC168. Northern signal quantitation was performed using ImageQuant software.

Polyribosome Analysis

Sucrose density gradients for polyribosome analysis were performed essentially as described previously (Hu et al., 2009). Specifically, cells were grown until mid-log phase (OD600=0.4-0.45) at 24° C. in synthetic media with the appropriate amino acids and 2% glucose. For glucose deprivation experiments, cells were centrifuged and resuspended in media with or without glucose for 10 min before harvesting. All cells were treated with cycloheximide to a final concentration of 100 μg $ml^{-1}$ and collected by centrifugation. Cell pellets were lysed in buffer (10 mM Tris, pH 7.4, 100 mM NaCl, 30 mM $MgCl_2$, 1 mM DTT, 100 μg $ml^{-1}$ cycloheximide) by vortexing with glass beads, and cleared using the hot needle puncture method followed by centrifugation at 2,000 rpm for 2 min at 4° C. After centrifugation of the supernatants at 29,000 r.p.m. for 10 min with a TLA 120.2 rotor, Triton X-100 was added to a final concentration of 1%. Sucrose gradients were made on a Biocomp gradient maker and were 15-45% weight/weight (sucrose to buffer (50 mM TrisAcetate pH 7.0, 50 mM $NH_4Cl$, 12 mM $MgCl_2$, 1 mM DTT)). 10 units (OD260) of cell lysate were loaded onto each gradient. Gradients were centrifuged at 41,000 r.p.m. for 2 h and 26 min at 4° C. in a Beckman SW-41Ti rotor and fractionated using a Brandel Fractionation System and an ISCO UA-6 ultraviolet detector. Fractions were precipitated overnight at −20° C. using 2 volumes 95% ethanol. RNA/protein was pelleted at 14,000 rpm for 30 min, then pellets were resuspended in 500 μL LET (25 mM Tris pH 8.0, 100 mM LiCl, 20 mM EDTA) with 1% SDS. Fractions were then extracted once with phenol/LET, once with phenol/chloroform/LET, and then were precipitated with one-tenth volume of 7.5 M $CH_3COONH_4$ and 2 volumes 95% ethanol. After centrifugation at 14,000 rpm for 20 min, pellets were washed once with 700 μL 75% ethanol, air dried, and resuspended in 1×LET. Half of each sample was loaded on 1.4% agarose-formaldehyde gels and Northern analysis carried out as above. For HIS3, northern blots of RNA from cells without stress were probed with oligonucleotide oJC2564 and northern blots of RNA from cells with stress were probed with probes generated by radiolabeled asymmetric PCR for increased sensitivity. For RPS20, blots were probed with oligonucleotide oJC2632. For LSM8, an asymmetric PCR probe was used for increased sensitivity. To generate the asymmetric PCR probes, plasmids pJC711 and pJC716 were used as templates to amplify non-optimal and optimal HIS3 sequences, respectively, in a first PCR using oJC2540 and oJC2541 and Phusion Taq polymerase (BioLabs). The PCR products were run on 1% agarose gel and the single amplicons were extracted using a GenElute Gel extraction kit (Sigma) and resuspended in 30 μL of water. 4 μL were added to a final 50 μL PCR mix containing dATP, dGTP, dTTP (200 μM each), dCTP (3 μM), the reverse primer oJC2564 (HIS3 ORF, 1 μM), 50 μCi of [a-32P]dCTP (3000 Ci/mmol; 10 μCi/μL) and 5 units of Taq polymerase. After denaturation at 94° C. for 5', asymmetric amplification was performed for 40 cycles (15 sec at 94° C., 30 sec at 58° C., 30 sec at 72° C.) followed by 10 min at 72° C. The obtained radiolabelled probes were purified on Micro Bio-Spin 6 Chromatography Columns (BioRad) following the manufacturer's instructions. For LSM8, the PCR template was generated using oligonucleotides oJC2357 and oJC2358. The reverse primer for the asymmetric PCR was oJC2633. Blots were pre-hybridized 1 h at 42° C. in 50% formamide, 5×SSC, 1×Denhardt's, 0.5 mg/mL salmon sperm DNA, 10 mM EDTA and 0.2% SDS, and probed with the optimal or non-optimal single-stranded probes generated by asymmetric PCR overnight at 42° C. in the same buffer. They were washed twice for 5 min at room temperature in 2×SSC, 0.1% SDS, and once for 45 min at 50° C. in 0.1×SSC, 0.1% SDS, and then placed on phosphorimager screens for overnight exposure.

RNA-Seq rpb1-1 mutant cells (Nonet et al., 1987) (yJC244) were grown to mid-log phase at 24° C. as described above. To achieve transcriptional repression, cells were shifted to 37° C., then cell aliquots were removed and isolated total RNA was used for library construction. 10 time points were collected over 60 minutes, including an initial aliquot at time 0 collected before the temperature shift. Total RNA libraries were then prepared using the Illumina TruSeq Stranded Total RNA library prep kit. The starting material consisted of 1 μg of total RNA and 1 ng of ERCC Phage NIST spike-ins. Poly(A)+ RNA libraries were prepared using the Illumina TruSeq Stranded mRNA library prep kit. The starting material for these libraries consisted of 4 μg of RNA and 1 ng of ERCC Phage NIST spike-ins. The libraries were quantitated using an Agilent Bioanalyzer and sequenced on an Illumina HiSeq2000 using paired-end 100 bp reads with an index read.

Alignment and Half-Life Calculation

Reads were aligned to the SacCer2 *S. cerevisiae* reference genome using Bowtie v0.12.7 (Langmead et al., 2009) using the parameters '-m 1-v 2-p 8'. The remaining unaligned reads were then aligned to a reference file containing the sequences of the spike-in controls using the same parameters. The aligned reads were then converted into bam format and indexed using samtools v0.1.18 (Li et al., 2009). Gene FPKM values were calculated with Cufflinks v1.3.0 (Trapnell et al., 2010) using default parameters and a gtf file of the SGD gene annotation downloaded from the SacCer2 UCSC browser. The raw FPKM numbers were then normalized to the number of reads aligning to the spike-ins to adjust for the amplification resulting from a smaller pool of mRNA at later time points.

To estimate the half-life for each gene, we normalized each of the expression levels for each gene and each time series to the initial expression level. We then fit an exponential decay curve to the data by minimizing the sum of the absolute residuals for each gene. We filtered the list to exclude dubious and unverified ORFs, genes for which the average absolute residual was greater than 0.14, and genes which had an estimated half-life longer than the measured time course. To get a very rough idea of the variability in our estimates of the gene half-lives we performed a bootstrap type procedure. The un-normalized residuals from the original data were resampled for each gene and added to the un-normalized fitted curve values to repeatedly simulate new sample data sets. The 95% confidence intervals were based on the 2.5% and 97.5% quantiles of the half-life estimates calculated from the simulated data sets.

Statistical Methods

The Codon occurrence to mRNA Stability Correlation coefficient (CSC) was determined by calculating a Pearson correlation coefficient between the frequency of occurrence of individual codons and the half-lives of the messages containing them (FIG. 1A). To determine the statistical significance of the association between codon optimality and the CSC (FIG. 2A, C), we first categorized the CSC as either positive or negative. We then used a chi-squared test of association. We also used linear regression (FIG. 2D). Similarly, to look at association in between the categories of optimal codon content and mRNA half-life (FIG. 3F), we used an ANOVA f-test with mRNA half life on the log scale.

Any test of association between codon optimality and transcript stability may show artificial statistical significance due to confounding with the base pair content of the genes. To help mitigate this possibility, for each test statistic, we randomly permuted the base pairs of the genes and recalculated the test statistic for each of 10,000 permutations. We calculated the base pair permutation p-value as the number of permuted data sets with a test of association stronger than the chi-squared test in the un-permuted data. Statistical calculations were done using the R environment. Percent optimal codon values were calculated by generating a list of optimal and non-optimal codons as previously described.

Heat Map Generation

For all mRNA with reliable half-lives, rates of usage of each of the 61 codons was calculated by using an in-house perl script. These values were then input into an Excel spreadsheet, assigned ranks using the RANK.AVG function, and then exported to a tsv file. These were then evaluated using a Spearman distance metric and clustered using k-means clustering in Cluster3. The clustered output was visualized and color coded using the log-scale option of Java Treeview.

Results

Measuring global mRNA decay rates using methods that either enrich for polyA+ RNA from total RNA samples and/or synthesize complementary DNA (cDNA) using oligonucleotides annealed to the poly(A) tail may fail to capture important information for several reasons. Although it is firmly established that deadenylation is the rate limiting step in mRNA turnover, we and others have observed that specific mRNAs persist in cells as "stable" deadenylated species. For such transcripts, decapping and subsequent decay is delayed and decapping becomes the rate defining step for mRNA degradation. Moreover, some mRNAs may contain structures that impede poly(A) tail function. Lastly, since the process of deadenylation converts an mRNA species from one that can be efficiently captured by oligo dT to one that cannot, the overall level of information gained may vary with the level of poly(A) enrichment achieved in the protocol used. With this in mind, we sought to determine how prevalent these phenomena are on a transcriptome-wide level. For this purpose, we performed a time course after inactivation of RNA polymerase II. At each time point, libraries were prepared from either oligo-dT selected mRNAs or rRNA-depleted whole cell RNA and subjected to Illumina sequencing. This approach allowed us to compare poly(A) half-lives (oligo dT) with total mRNA decay rates (rRNA depleted; FIG. 1A). Remarkably, the vast majority (92%) of transcripts for which we could confidently calculate half-lives (3969) had longer half-lives when the rRNA depleted libraries were analyzed relative to the half-lives determined from poly(A) selected libraries (FIGS. 1B and C). It is important to note that not all of these transcripts exist as deadenylated RNAs since mRNAs with short poly (A) tails will not bind oligo dT. These data indicate that mRNA half-lives determined by oligo dT selection give highly skewed values. For example, the ADHD mRNA had a calculated half-life of 4.2 minutes when determined from poly(A) selected RNA and a 31.7 minute half-life when determined from rRNA depleted RNA.

With this data in hand we attempted to identify sequence motifs that might dictate stability or instability, without success. Following up on previous observations that inclusion of ten consecutive rare codons in the open reading frames of an otherwise stable mRNA caused a dramatic decrease in stability, we inspected our transcriptome-wide mRNA half-life data to determine whether codon content within ORFs could affect mRNA stability. To do so, we determined if mRNAs enriched in any individual codon demonstrated greater or lesser stability. We defined mRNAs as stable if they have a half-life greater than 2-fold longer than the average (~20 min), and unstable if they have a half-life less than half of the average (~5 min). For each codon, we calculated a correlation between the frequency of occurrence of that codon in mRNAs and the stabilities of the mRNAs. Occurrences of a codon were compared to the half-life for each mRNA and a Pearson correlation calculation was used to generate an R-value (graphically represented for sample codons in FIG. 8E). We refer to this metric as the Codon occurrence to mRNA Stability Correlation coefficient (CSC). The CSC values for all codons were then compared to each other (FIG. 2A). Strikingly, it was observed that some codons preferentially occurred in stable mRNAs while others occurred preferentially in unstable mRNAs (overall p-value=1.496e-14, permutation p-value $<10^{-4}$). For example, the GCT alanine codon was highly enriched in stable transcripts as defined by our RNA-seq analysis, while its synonymous codons, GCG and GCA were preferentially present in unstable transcripts (FIG. 2A). Approximately one-third of all codon triplets were overrepresented in stable mRNAs, while the remaining two-thirds appeared to predominate in unstable mRNAs. As a consequence of the large dataset and significance of the observed correlation, these data strongly suggest that codon usage influences mRNA degradation rates.

Strikingly, codons associated with stable or unstable mRNAs nearly perfectly mirrored their assignment as optimal or non-optimal, respectively (FIG. 2C). Direct comparison between our CSC metric and tAI revealed very good overall agreement between these values (FIG. 2D; R=0.753, p-value=2.583e-12, permutation p-value <10-4). Importantly, the relationship between optimal codon content and mRNA half-life is independent of the method used to determine half-life. We repeated our analysis of codon usage vs. mRNA half-life using mRNA decay rates. These data were obtained with a steady state approach calculation using metabolic labeling that minimally perturbs the cell and is completely distinct from our method. Both datasets show a similar and striking correlation between optimal codon content and mRNA decay rate.

To determine if the codon optimality correlation was possibly masking other features that might actually be determining mRNA half-life (e.g., sequence content, GC percentage, or secondary structure), we reanalyzed our data after computationally introducing +1 and +2 frameshifts. In the analysis of these frameshifted ORFs, the correlation between codon content and stability completely disappears, thus eliminating other variables as determinative (FIG. 2E; R=−0.127, p-value=0.3303, permutation p-value=0.8847 and FIG. 2F; R=−0.288, p-value=0.0242, permutation p-value=0.0012).

Stable and Unstable mRNAs Demonstrate Different Optimal Codon Content

As shown above, computational analysis of our global mRNA stability data revealed a relationship between codon occurrence and mRNA half-life. These data indicate that either particular codons alter stability or overall codon content within an mRNA works collectively on stability. To evaluate the relationship between optimal codon content and decay rate on the level of individual transcripts, codon usage was mapped across all individual transcripts. Cluster analysis revealed that different mRNAs are biased towards using different types of codons. The overall result is not surprising, as codon bias has been well studied; however, the pattern of codon usage demonstrates that certain classes of mRNAs predominately use either optimal or non-optimal codons (FIGS. 3A and B) and that this usage correlates with the overall transcript stability (FIG. 3C). Closer inspection of several stable mRNAs revealed that these transcripts were not enriched in any particular codon, but an overwhelming proportion (>80%) of codons fell into the category of optimal (FIG. 3D). By contrast, individual unstable mRNAs were found to be enriched (60% or greater) in non-optimal codons (FIG. 3E). These analyses demonstrated that in this set of mRNAs, the stable mRNAs are biased towards harboring predominately optimal codons and the unstable mRNAs are enriched in nonoptimal codons, though the specific codon identities vary between individual transcripts.

Extending this analysis to the level of the whole transcriptome, a correlation between optimal codon content and mRNA stability was observed when the proportion of optimal codons within an mRNA was evaluated by percentiles. Specifically, mRNAs with less than 40% optimal codons were typically found to be unstable, with a median half-life of 5.4 minutes. In contrast, mRNAs with 70% optimal codon content or greater were found to be stable, with a median half life of 17.8 minutes (FIG. 3F).

Optimal Codon Content Directly Influences mRNA Decay Rate

To experimentally validate the relationship observed in the computational analysis, we evaluated the effects on stability of altering the percentage of optimal codons within an mRNA. We modified the codon content of the unstable LSM8 mRNA (half-life=4.65 min) by making synonymous optimal substitutions in 52 of its 60 nonoptimal codons. Similarly, we replaced the majority of optimal codons (108 of 113) within the coding region of the stable RPS20 mRNA (half-life=25.3 min) with synonymous, non-optimal codons. This methodology ensured that the polypeptides encoded by these sequences were unchanged from the native form. Moreover, the substitutions were selected to avoid significantly altering the GC content of the coding region or introducing any predicted RNA secondary structure (data not shown). Northern blot analysis of these mRNAs after transcriptional inhibition revealed that alteration of the codons within these two transcripts resulted in dramatic changes in their stability. Specifically, the half-life of LSM8 mRNA was increased greater than 7-fold as a consequence of the conversion of non-optimal codons into synonymous optimal codons in its ORF (half-life=18.7 min; FIG. 4A). In contrast, substitution of non-optimal for optimal codons within the stable RPS20 mRNA resulted in a sharp (10 fold) reduction in its stability (half-life=2.5 min; FIG. 4B). These data demonstrate that identity of codons within an mRNA can strongly influence stability, and that optimal codon content contributes significantly to determining the rate of mRNA decay in vivo.

To further examine the relationship between optimal codon content and mRNA stability, we generated two synthetic open reading frames which encode identical 59 amino acid polypeptides but differ in the optimality at each codon (SYN reporters; FIGS. 10A, B, and C). We introduced the synthetic ORFs into a reporter bearing the 5' and 3'UTRs of MFA2, a well studied mRNA which is rapidly degraded in the cell (half-life=3.0 min), a phenomenon shown to be mediated, in part, by elements encoded within its 3'UTR. We also introduced the synthetic ORFs into a reporter with the 5' and 3' UTRs of PGK1, a well characterized and stable mRNA (half-life=25 min; Muhlrad et al., 1995). When stability of the four reporter mRNAs was measured by transcriptional shut-off analysis, the transcripts encoding the optimal SYN ORF were found to be significantly more stable (~4-fold) than their counterparts bearing the non-optimal codons (FIG. 4C). Importantly, degradation of both the optimally and non-optimally encoded SYN reporter mRNAs was determined to occur through the deadenylation-dependent decapping pathway used to degrade the majority of endogenous mRNAs in yeast, and was not mediated by any of the three pathways known to target aberrant mRNA. High-resolution northern analysis of the decay of these mRNAs confirmed that the rates of both deadenylation and decapping, the regulated steps in the normal decay pathway, were affected as a consequence of changes in codon composition within the reporter ORFs. These data demonstrate that optimal codon content is a critical determinant of mRNA stability influencing both the rate of deadenylation and decapping during turnover of the mRNA independently of 5' and 3' UTRs, which can act in parallel to stabilize or destabilize the mRNA.

Optimal Codon Content Influences Translational Efficiency

To evaluate the influence of codon optimality on mRNA translation efficiency in vivo, we generated three new reporters that differ in optimal codon content but do not differ in amino acid sequence. Specifically, we engineered the ORF of the HIS3 gene to contain either all optimal (HIS3 opt) or all non-optimal codons (HIS3 non-opt), with the wild-type HIS3 gene providing an intermediate point at 43% optimal codons (FIG. 5A). The HIS3 gene was chosen because it has a relatively long ORF (220 amino acids) compared to our other synonymous mutation constructs, allowing us to effectively monitor ribosome association by sucrose density gradients (see below). We then determined the mRNA decay rate of the three HIS3 constructs by transcriptional shutoff analysis using an rpb1-1 strain. Consistent with our previous results, it was observed that changing optimal codon content produced a dramatic effect on mRNA half-life (FIG. 5B). Notably, the effect on HIS3 mRNA decay matched the percent of optimal codons used. The half-life of the optimal construct (half-life >60 min) was much greater that of the WT construct (half-life=9.5 min) whose half-life was markedly greater than the nonoptimal construct (half-life=2.0 min). Thus, we can achieve a full range of mRNA halflives in yeast without altering protein sequence or flanking sequences by changing optimal codon content.

We hypothesized that codon optimality should influence translation elongation. We tested this hypothesis using two approaches. First, we monitored the protein output from the HIS3 optimal construct vs. the HIS3 non-optimal construct by western blot, and then normalized the protein expression to the mRNA levels, as determined by northern blot. We observed that the non-optimal construct had four-fold less protein output than the optimal construct (FIG. 5C). Second, we evaluated the ribosome density on the HIS3 mRNA constructs. Ribosome density was monitored using sucrose gradients, followed by fractionation and northern blotting of the isolated fractions. Critically, it was observed that the ribosome occupancy was nearly identical for all three HIS3 reporter mRNAs (FIG. 5D). Thus, we show that a four-fold decrease in protein output, in conjunction with nearly identical localization within a polyribosome, suggests a decrease in ribosome translocation rate on the non-optimal construct as compared to the optimal.

Optimal Codon Content Impacts Ribosome Translocation

To directly determine whether ribosomes translocate slower on mRNAs containing non-optimal codons vs. optimal codons, we monitored ribosomal run-off of these two reporters. To do this, we blocked translational initiation by depriving cells of glucose for 10 minutes. Glucose deprivation results in rapid inhibition of translational initiation and thus bulk polyribosomes are lost by run-off (FIG. 6A vs. C). To monitor ribosomal run-off, we extracted mRNA-ribosome complexes before and after glucose deprivation, separated the material with a sucrose gradient, collected fractions, and monitored the presence of the HIS3 mRNAs in each fraction by northern analysis. Importantly, under normal conditions the ribosome occupancy of the HIS3 opt and non-opt constructs was determined to be similar (FIG. 6B); however, upon induction of ribosome run-off, a large fraction of the optimal construct mRNA relocated to the top of the gradient in the ribosome-free area, while the HIS3 non-opt mRNA remained largely associated with polyribosomes (FIG. 6D). We extended this analysis to two endogenous mRNA transcripts that differ dramatically in codon optimality, LSM8 (45% optimal codons) and RSP20 (92% optimal codons). Notably, the endogenous LSM8 mRNA was retained on polyribosomes following inhibition of translational initiation, while the RPS20 mRNA dissociated efficiently. We propose that the difference in retention is due to more efficient ribosome translocation on messages with high optimal codon content. Thus, the retention of the mRNAs bearing predominantly non-optimal codons in polyribosomal fractions indicates that codon optimality can impact the rate of ribosome translocation directly.

Precision in Gene Expression is Achieved Through Coordination of Optimal Codon Content A previous analysis of mRNA stability in yeast revealed that the decay rates of some mRNAs encoding proteins that function in the same pathway or are part of the same complex were similar. Turnover of individual mRNAs appears to be based on the physiological function and cellular requirement of the proteins they encode. We hypothesized that modulation of optimal codon content may provide the mechanism for the cell to coordinate the metabolism of transcripts expressing proteins of common function. We assessed codon usage for genes whose protein products function in common pathways and/or complexes. We observed that mRNAs encoding the enzymes involved in glycolysis (n=10) had a similar and extraordinarily high proportion of optimal codons (mean=86%; FIG. 7A). These transcripts were determined to be stable both previously and in our genome-wide analysis (median half-life=43.4 min; Wang et al., 2002). In contrast, mRNAs encoding polypeptides involved in pheromone response in yeast cells (n=14) were all unstable (median half-life=5.6 min; Wang et al., 2002) and harbored an average of only 43% optimal codons (FIG. 7A). Our analysis revealed that other groups of transcripts behave similarly. The stable large and small cytosolic ribosomal subunit protein mRNAs (n=70 and 54, respectively; median half-life=18.9 min and 20.2 min, respectively) demonstrated an average optimal codon content of 89% and 88% respectively, but mRNAs that encode ribosomal proteins functioning in the mitochondria are unstable (n=42; median half-life=4.8 min), consistent with the observation that they have 45% optimal codon content. (FIGS. 7A and B). Other families of genes that have similar decay rates include those whose protein products are involved in ribosomal processing, tRNA modification, the TCA cycle, RNA processing, and components of the translational machinery (FIG. 7 and data not shown). These data provide evidence that transcripts expressing proteins of related function are coordinated at the level of optimal codon content as well as decay rate, suggesting that these genes may have evolved specific codon contents as a mechanism to facilitate precise synchronization of expression based on their function in the cell.

Example 2

Codon Optimization of yeast glucoamylase genes

Glucoamylase (α-1,4-glucan glucohydrolase, amyloglucosidase, EC 3.2.1.3) is of great importance to the fermentation and food industries for saccharification of starch and other related oligosaccharides. Glucoamylase enzymes for saccharification can be used on liquefied starch-containing substrates to produce sugars which in turn serve as a feedstock for biological fermentations in the industrial production of ethanol. Therefore, codon optimization of nucleic acid sequences encoding glucoamylase can allow for increased glucoamylase enzyme output and thus increase the production yield of ethanol.

Here we report the optimized nucleic acid sequences encoding 3 different yeast structurally related glucoamylase enzymes, SGA1, STA2 and STA1.

By making synonymous optimal substitutions of nonoptimal codons in SGA1, STA2 and STA1 glucoamylase encoding nucleic acid sequences, we generated optimized cDNA sequences having a codon stabilization coefficient (CSC) that is higher than a non-optimized sequence, (e.g., a corresponding SGA1, STA2 or STA1 wild-type glucoamylase sequence) thereby allowing for the increased expression of the recombinant glucoamylase protein in a host cell.

In total, thirty-three optimized glucoamylase encoding nucleic acid sequences were generated. The thirty-three optimized glucoamylase encoding nucleic acid sequences generated include ten optimized SGA1 cDNA sequences (SEQ ID NOs 1-10), twelve optimized STA2 cDNA sequences (SEQ ID NOs: 11-21), and eleven STA1 cDNA sequences (SEQ ID NOs:22-32).

Optimized nucleic acid sequences encoding a SGA1, STA2 and STA1 glucoamylase are recombinantly expressed by molecular cloning into an expression vector containing a suitable promoter and other appropriate transcription regulatory elements, and transferred into eukaryotic host cells to produce a recombinant glucoamylase protein The transfected host cell are then cultured in a suitable culture media appropriate for the expression of the glucoamylase protein where the protein is subsequently collected.

The glucoamylase protein output from an optimized construct vs. the non-optimized construct are monitored by western blot, and the protein expression to the mRNA levels are normalized, as determined by northern blot.

Example 3

The DEAD-Box Helicase Dhh1p Couples mRNA Decay and Translation by Monitoring Codon Optimality Messenger RNA degradation represents a critical step in the regulation of gene expression. In budding yeast, most mRNAs are degraded by initial removal of the 3' polyadenosine tail. This leads to subsequent cleavage of the 5' cap structure in a process term 'decapping' followed by digestion of the mRNA body by a 5' to 3' exoribonuclease enzyme. While the major pathway and the enzymes catalyzing mRNA turnover have been identified, a mechanism to account for disparate mRNA half-lives has been elusive. We have discovered that codon optimality is a major feature that contributes to determining mRNA stability. Using a genome-wide RNA decay analysis we found that stable mRNAs are enriched in optimal codons, whereas unstable mRNAs are enriched in non-optimal codons. These results establish the existence of coupling between active translation by ribosomes of an mRNA and its stability. Reporter studies recapitulated these striking genome-wide results. Similar effects of codon usage on mRNA stability were recently observed in bacteria and metazoans.

The inherent degeneracy of the genomic code leads to the possibility that synonymous codons are recognized distinctly by the ribosome as a function of subtle differences in tRNA availability, demand, decoding fidelity, and mRNA secondary structure propensity. All of these factors can lead to variability in codon-specific rates of translation. Codon optimality is a term coined to discuss the nonuniform recognition of each of the 61 codons by the ribosome based on supply and demand arguments. Codon bias, which is the frequency at which distinct synonymous codons are present within the genome is, in part, shaped by codon optimality. Codons that are evolutionarily enriched in highly translated mRNA transcripts are often optimal codons (i.e., triplets that are decoded by tRNAs of relatively higher abundance), whereas codons that exhibit no such selective bias are typically nonoptimal and are decoded by tRNAs of relatively lower abundance. Since codon bias is distinct for every genome and represents a balance between selection, mutation, and genetic drift, codon optimality is often found to be distinct between species. In broad terms, it is generally accepted that the speed at which the ribosome decodes is affected by the subtle distinctions in tRNA concentrations between synonymous sets of codons. Thus tRNA abundance is a critical regulator of ribosome elongation rates and therefore can impact the efficiency of protein folding, protein stability, protein activity, and the coordinate expression of functionally related genes.

Attempts to observe differences in elongation rate that are dependent on codon identity and optimality using ribosome profiling, however, have been challenging. While a number of studies have found a modest correlation between codon optimality and ribosome occupancy, others have observed increased ribosome occupancy on codons with low abundance cognate tRNAs. There has been great effort to resolve these discrepancies, with recent work showing that coupling between codon optimality and ribosome occupancy can be masked by pre-treatment of cells with translational inhibitors.

The regulation of elongation rate and post-translational events (i.e., protein folding and protein activity) by codon optimality is simply a consequence of functional tRNA concentration, a "passive response". On the contrary, the regulation of mRNA turnover by codon optimality likely represents a more active process, with the ribosome's elongation rate under constant surveillance by component(s) of the mRNA turnover complex. Herein we focus on identifying a cellular factor that senses slow ribosomes to coordinate and couple translation and mRNA decay.

Dhh1p (DDX6) is a highly conserved and abundant DEAD-box RNA helicase previously implicated in translational repression and mRNA decay. In budding yeast, loss of DHH1 activity results in a block in mRNA decapping, but unlike other decapping regulators, this function is dependent on the translational status of the mRNA. Moreover, previous studies showed that direct tethering of Dhh1p to the 3' UTR of a reporter mRNA resulted in loss of protein production but dramatic ribosome accumulation on the message. These data suggest that Dhh1p directly impacts ribosome movement or processivity.

Here we demonstrate that Dhh1p is a critical factor in distinguishing between mRNAs containing optimal and non-optimal codons and targeting them for decay. mRNA binding studies show that Dhh1p is more efficiently recruited by nonoptimally coded mRNAs. In addition, ribosome occupancy is specifically modulated on optimally and non-optimally coded genes (and codons) by Dhh1p. Finally, Dhh1p binds to ribosomes in vivo. Together these results suggest that Dhh1p is a sensor of slow ribosomes and communicates this information to the mRNA decay machinery to consolidate downstream output.

Results

Codon Optimality is a Powerful Determinate of mRNA Decay

We have previously demonstrated that codon optimality is a major determinant of mRNA degradation in *S. cerevisiae*. In our previous work, we established a biological metric that indicates the overall contribution of each of the 61 codons toward mRNA stability. We referred to this metric as the codon stabilization coefficient (CSC). Because these CSC scores correlated nicely with previously established metrics for optimality, we argued that mRNA stability is influenced by translational elongation rate.

An analogous metric is the tRNA Adaptation Index (TAI), which quantifies the relative cellular "supply" of cognate and near-cognate tRNAs for a given codon. However, in this study, we use a slightly different metric referred to as the species-specific TAI or sTAI. While these quantities are largely identical on a per-codon basis, the parameters for sTAI are derived purely through sequence information, whereas the original definition of TAI takes into account actual gene expression data. As we here characterize codon effects on gene expression and translation, we opted for the more naïve metric (sTAI) to avoid the potential pitfall of data overfitting.

Figure 8C:
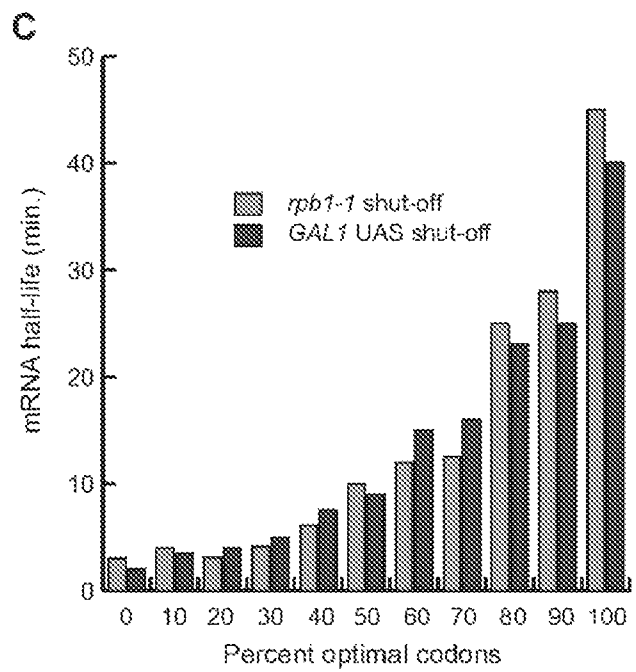
Figure 8B:
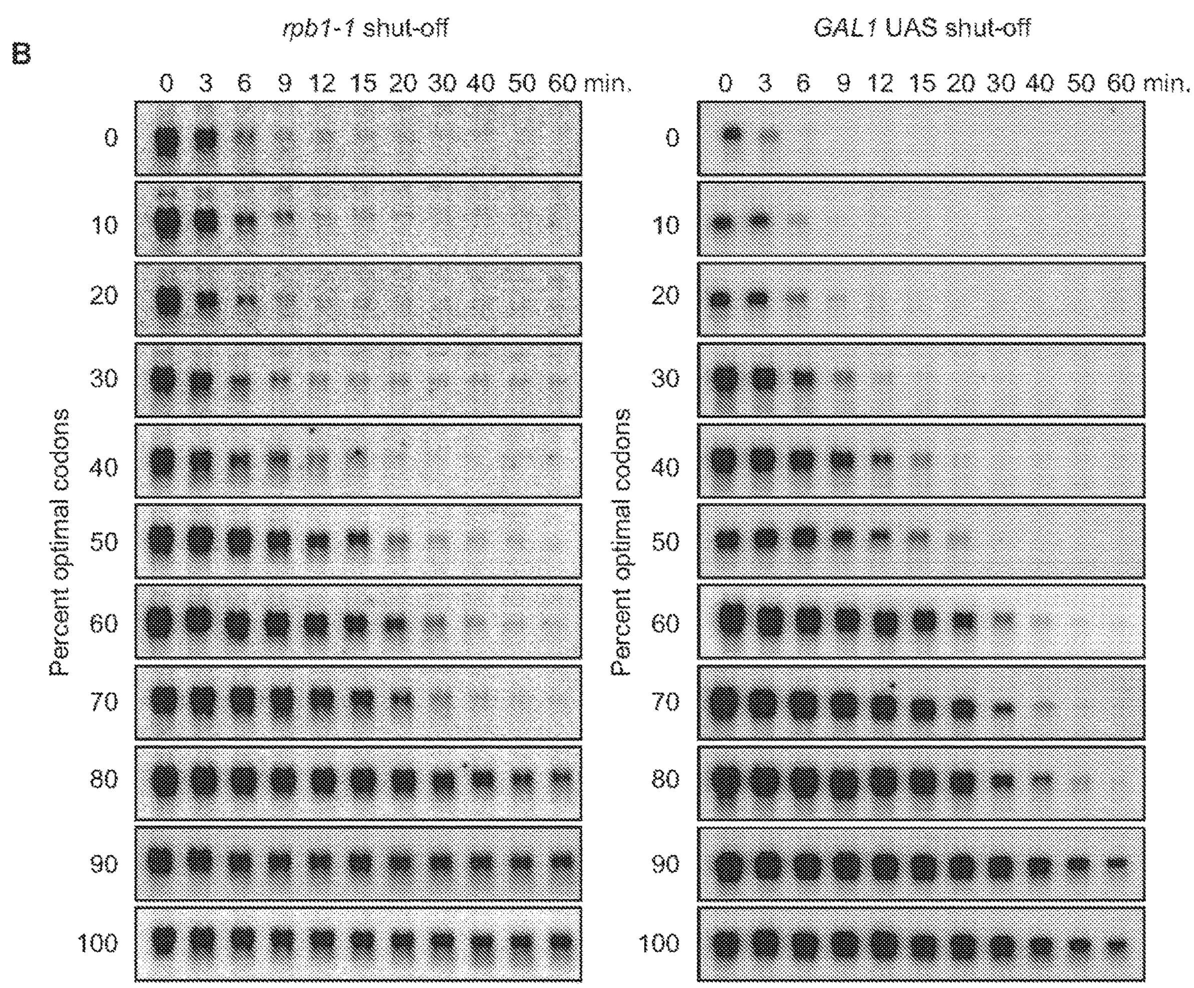
Figure 15A:
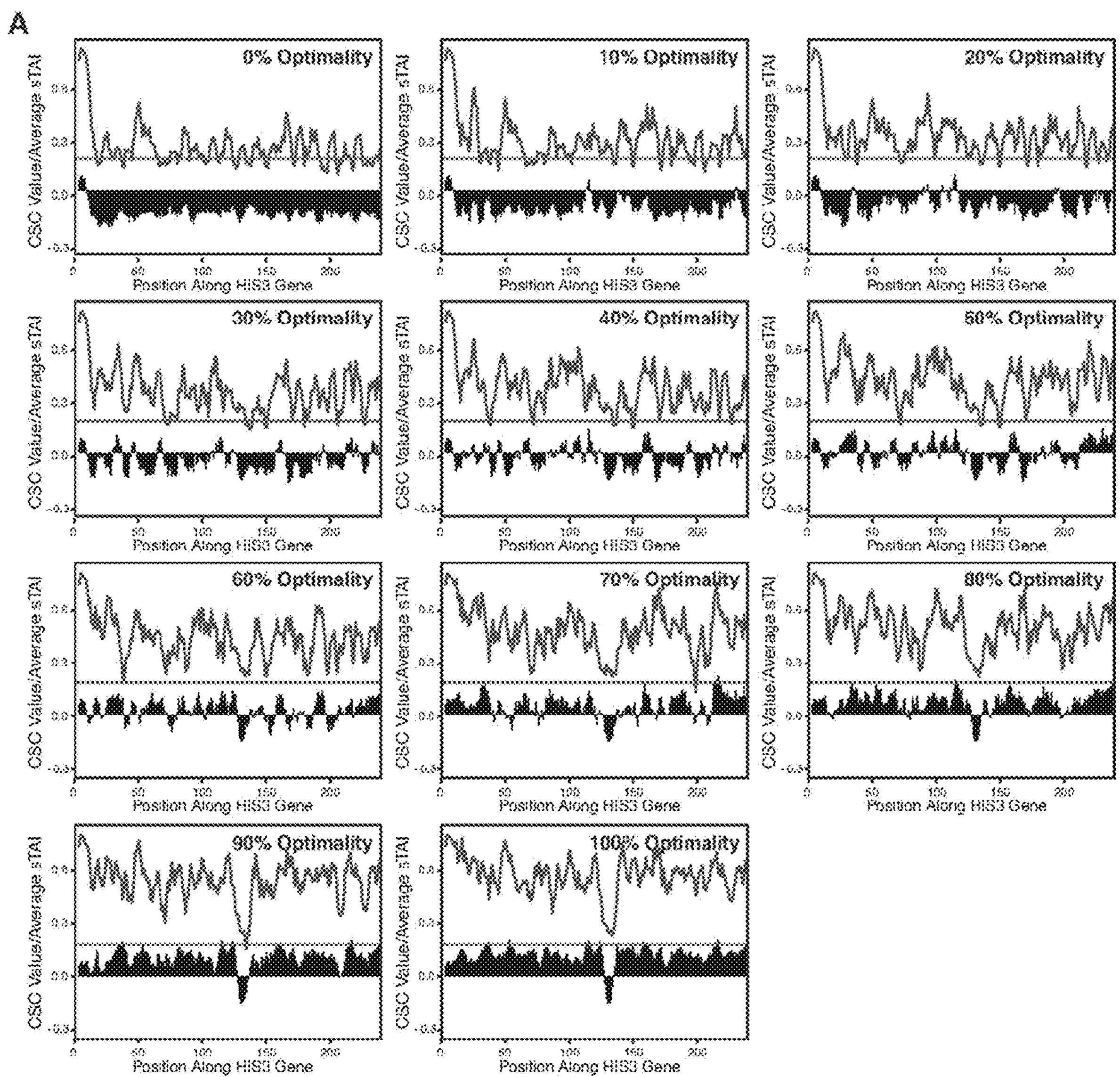
FIGS. 15(A-B) illustrate codon composition of HIS3 reporters varying in codon optimality (A) Graphs for CSC values (black bars) and sTAI values (blue line) averaged across five codon-long windows within the ORF of the HIS3 reporters. The red line represents the average sTAI across the gene for the 0% optimal HIS3 reporter. The total percent optimality is shown above each graph. Note the 5' end of each reporter is tagged with FLAG of consistent codon composition. Moreover, an identical codon stretch is present in all 11 reporters that comprise the probe site used for Northern analysis. (B) The correlation between the average CSC and average sTAI across the 11 reporters.
Figure 15B:
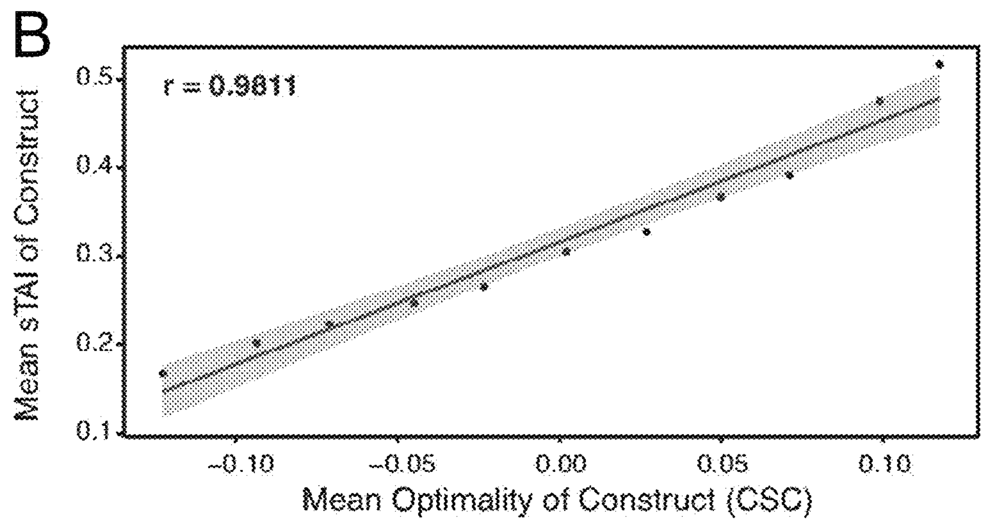

Here we began our study by following up on earlier results in Example 1 below and creating eleven constructs that differ slightly in codon optimality, as defined by both CSC and sTAI. Importantly, all eleven constructs produce the identical polypeptide (i.e., the HIS3 protein; FIG. 8A) but do so using a distinct mixture of synonymous optimal or non-optimal codons. Between these constructs, the percentage of optimal to non-optimal codons varies by only 10 percent, allowing for coverage of the complete range of optimal codon content seen within the genome (FIG. 8A). The assignment of codons within each construct was done randomly using a computer algorithm (FIG. 15A) where the average CSC and sTAI for each construct were found to be highly correlated (FIG. 15B). We monitored mRNA decay rate using a temperature sensitive allele of RNA polymerase II (i.e. rpb1-1). Transcription was inhibited by quickly shifting cells from the permissive temperature to restrictive temperature (from 24° C. to 37° C.). Time points following this shift were taken, and mRNA was analyzed by Northern blot. As shown in FIG. 8B (left panel), the mRNA half-life varies with changing optimal codon content. These data agree with our previous findings that codon optimality is a major determinant of mRNA stability.

Importantly, protein synthesis rates are sensitive to stresses such as temperature shifts. Thus, the use of the temperature-sensitive allele rpb1-1 to monitor mRNA degradation has the potential to be misleading. To address this issue, we used an independent approach to test the influence of codon optimality on mRNA decay. For this experiment, we placed the same eleven constructs in FIG. 8B (left panel) under the control of the inducible GAL1 promoter. Cells were grown in galactose at 24° C. to mid-log phase. Transcription was then inhibited by adding glucose but maintaining the cells at 24° C. Following the addition of glucose, time points were taken, and mRNA was analyzed by Northern blot. Here, we also observed that codon optimality has a powerful influence on mRNA decay (FIG. 8B, right panel). In fact, the mRNA half-lives observed using the GAL1 shut-off approach are nearly identical to those obtained using an rpb1-1 shut-off (FIG. 8C). In both experiments, we observe the complete range of observed decay rates (from 3 min. to 45 min.) simply by changing codon composition without altering the polypeptide sequence. Together, these results indicate that codon optimality is a major contributor to mRNA stability. Importantly, even 10% changes in codon content have powerful effects on mRNA stability.

Dhh1p Stimulates the Degradation of mRNAs of Low Codon Optimality

As a known regulator of mRNA decapping and a translational repressor, two qualities that seem potentially relevant to the direct coupling between mRNA decay with codon optimality, we asked whether Dhh1p is a critical factor in mediating this connection by determining the influence of Dhh1p on the decay of RNA reporters of differing codon optimalities. For this, we utilized two reporter constructs (FIG. 9A) that encode the same polypeptide but are composed of either all optimal codons (OPT) or synonymous non-optimal (NON-OPT) codons. The reporter mRNAs were expressed under the control of the GAL1 UAS allowing us to monitor mRNA decay as described above. As shown in FIG. 9B, the OPT mRNA (sTAI=0.539) is more stable than the NON-OPT mRNA (sTAI=0.167) in WT cells (t1/2=17 min. vs. 3 min. respectively), consistent with our previous findings. Importantly, however, in the absence of DHH1, the OPT mRNA's half-life is unchanged relative to WT, while the NON-OPT is substantially stabilized (FIG. 9B). Indeed, in the absence of DHH1, the stability of the NON-OPT mRNA now mirrors that of the OPT mRNA. As a control we repeated these experiments in cells lacking PAT1 (another regulator of mRNA decapping), CCR4 (the major deadenylase), or DCP2 (the catalytic subunit of the decapping enzyme). In each case, the stability of both the OPT and NON-OPT mRNA increases, as anticipated for proteins implicated in mRNA decay, but the difference in stability of the OPT and NON-OPT constructs persists. Together, these data demonstrate that Dhh1p is a critical factor in determining the influence of codon optimality on mRNA decay.

We next measured the influence of Dhh1p on the decay of the eleven reporters used in FIG. 8B. The reporter mRNAs were expressed in dhh1Δ cells under the control of the GAL1 UAS allowing us to determine mRNA half-life by glucose-dependent transcriptional inhibition. RNA levels were quantitated by Northern blot. As shown in FIG. 9C, we observed that loss of DHH1 had the most dramatic effect on the mRNA reporters of low codon optimality (FIG. 9C; 0-50% percent optimal codons). The reporters bearing a high percentage of optimal codons were predominately unaffected by loss of DHH1. The data are consistent with our hypothesis that Dhh1p controls mRNA degradation by sensing translational elongation rate.

Figure 16A:
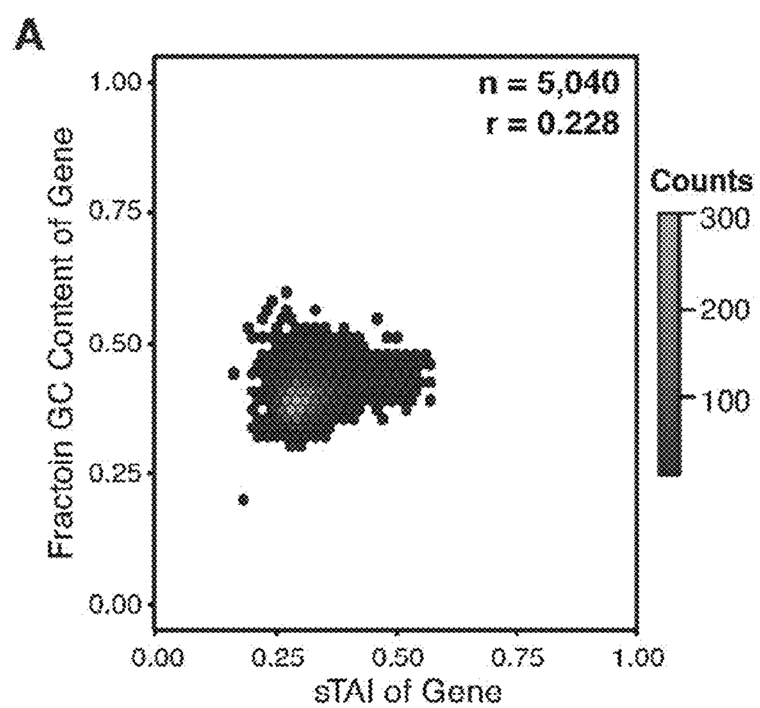
FIGS. 16(A-C) illustrate Non-optimality of mRNA transcripts is a proxy for poor translation. (A) Species-specific tRNA adaptation index (sTAI) plotted against percent GC content for all protein encoding transcripts in yeast. (B) Quantifying steady state levels of mRNAs transcripts by RNA-Seq in dhh1Δ cells (RPKM) relative to WT cells (RPKM) where transcripts are binned by fraction GC content. Shown are two biological replicates. A two-tailed Mann-Whitney test shows that low GC content mRNAs (GC Fraction=0.3, Med.=1.33) are not enriched relative to high GC content mRNAs (GC Fraction=0.55, Med.=1.36) upon Dhh1p depletion, U=5210, p=0.847. (C) Steady state levels of mRNA transcripts by RNA-Seq in WT cells where Dhh1p is constitutively over-expressed (OE) relative to WT cells where transcripts are binned by sTAI. Shown are two biological replicates. A two-tailed Mann-Whitney test shows that low optimality mRNAs (sTAI=0.25, Med.=1.09) are not enriched relative to high optimality mRNAs (sTAI=0.55, Med.=1.07) upon Dhh1p overexpression, U=5412, p=0.4593. (D) Steady state levels of mRNA transcripts by RNA Seq in WT cells where Dhh1p is constitutively over-expressed (OE) relative to WT cells where transcripts are binned by fraction GC content. Shown are two biological replicates. A two-tailed Mann-Whitney test shows that low GC content (GC Fraction=0.3, Med.=0.95) are not enriched relative to high GC content mRNAs (GC Fraction=0.55, Med.=1.06) upon Dhh1p overexpression, U=4102, p=0.2117.
Figure 16D:
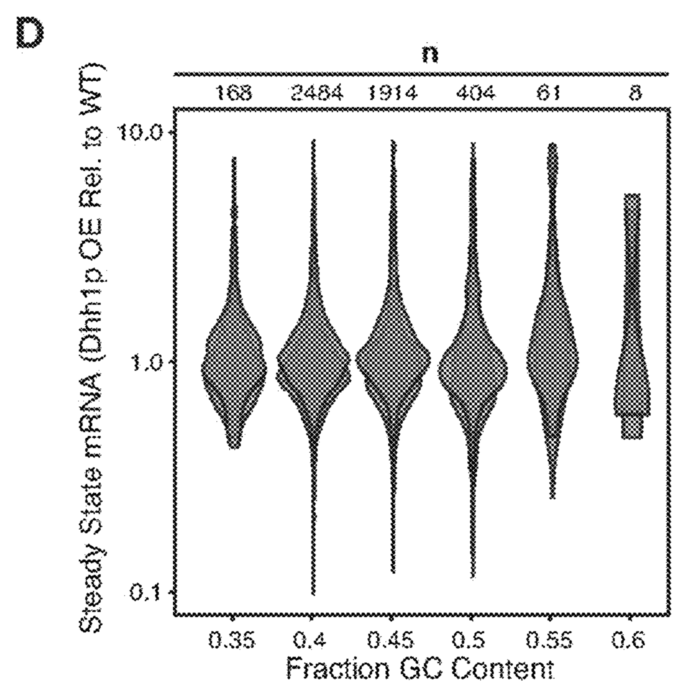

We extended our reporter analysis of Dhh1p to the entire genome by performing mRNA-seq in WT vs. dhh1Δ cells (FIG. 9D). Binning mRNAs by sTAI, we find that low sTAI mRNAs are preferentially stabilized in the absence of DHH1. To address possible concerns that sTAI is not directly reporting on the effects of codons on translation but is serving as a proxy for GC-content and/or mRNA structure, we looked at the correlation between sTAI and GC content (FIG. 16A) and asked whether the differential steady state levels of mRNA transcripts in WT cells vs. dhh1Δ exhibited a dependence on the GC content of the transcript. They do not (FIG. 16B). Thus, the major trend that emerges as significant from our analysis of the dhh1Δ strain relative to the WT is a correlation between sTAI and mRNA levels.

mRNA levels under constitutive overexpression of Dhh1p via GPD promoter, however, show no such trends with respect to optimality, suggesting that availability of downstream components (decay factors) may be limiting in these cells (FIG. 16C). Indeed, endogenous Dhh1p concentrations within the cell are already in large excess relative to other decapping factors. While these data represent a steady state analysis of mRNA levels, which necessarily misses some of the texture of a kinetic analysis, the data are nevertheless strikingly consistent with the kinetic observations made with reporter mRNAs.

Dhh1p Binds Preferentially to mRNA of Low Codon Optimality

The Dhh1p-dependent selective degradation of mRNAs of low sTAI predicts that Dhh1p will preferentially associate with these mRNPs. To test this, we determined the relative amount of Dhh1p associated with our OPT and NON-OPT mRNA reporters using an affinity pull-down approach (FIG. 10A). Specifically, we treated cells with a low level of formaldehyde to crosslink RNA to associated proteins. We prepared cell lysates and hybridized the mRNA samples to DNA oligonucleotides conjugated to biotin that is antisense to the common 3' UTR of the OPT and NON-OPT reporters. Following hybridization, RNP complexes were affinity purified using magnetic streptavidin beads. Bound material was stringently washed and then elution was performed using a low salt buffer. This approach was able to greatly enrich reporter mRNAs relative to an endogenous PGK1 mRNA (FIG. 10B). Moreover, analysis of Dhh1p bound to reporter mRNA by Western blot revealed a threefold enrichment of Dhh1p on the NON-OPT mRNA relative to the OPT mRNA. As a control, we found that the concentration of Poly(A) Binding Protein (Pab1p) isolated on both mRNAs was equal (FIG. 10C); as anticipated, we found no discernible GAPDH associated with either mRNP.

Figure 10D:
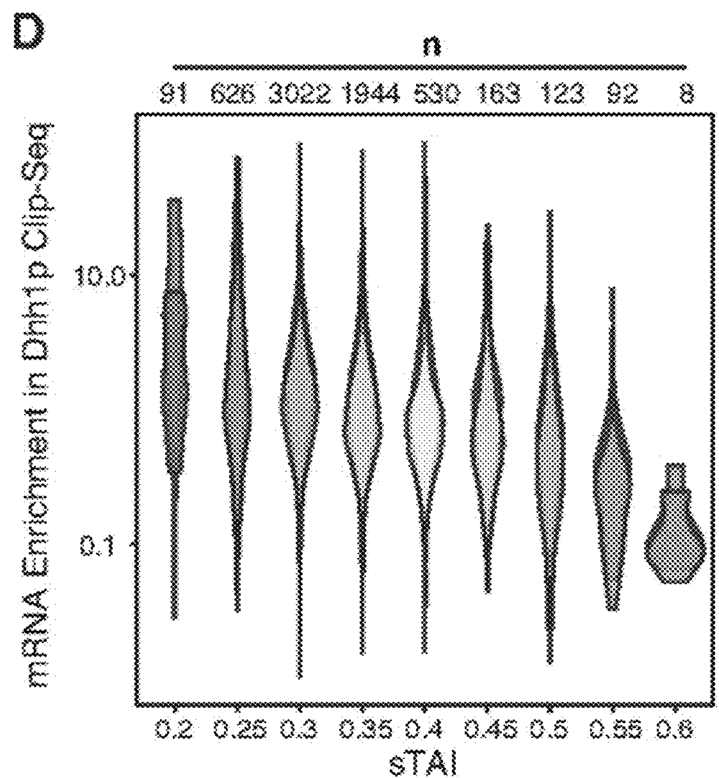
FIGS. 10(A-D) Dhh1p preferentially binds to mRNAs with low codon optimality. (A) Representation of the reporters and experimental design used for mRNA pulldown. A tag sequence (SEQ ID NO: 33) was inserted in the 3'UTR of the SYN reporters for pulldown. (B) Northern blot for the SYN mRNAs pull-downs. PGK1 mRNA was probed as a control of specificity. o: optimal, n: non-optimal. (C) Western blot showing the amount of Dhh1p, Pab1p and GAPDH pulled down by the SYN mRNAs. Quantitations of Dhh1p were normalized to mRNA levels from eluates in b. (D) Reanalysis of previously performed CLIP-Seq on Dhh1p calculating enrichment of mRNA transcripts bound to Dhh1p relative to WT conditions, where transcripts are binned by sTAI. Shown are two biological replicates. A two-tailed Mann-Whitney test shows that low optimality mRNAs (sTAI=0.25, Med.=2.02) are preferentially bound to Dhh1p relative to high optimality mRNAs (sTAI=0.55, Med.=0.32), U=304, $p=7.1\times10^{-9}$.

We extended this reporter analysis to define the association of Dhh1p with all mRNA transcripts on a genome-wide basis. Previous CLIP studies found that Dhh1p bound throughout the 5' and 3' UTRs and the ORF of most genes with no discernible binding motif and little apparent enrichment in any particular region of the transcript. We used the same published Dhh1p CLIP data and asked whether association of Dhh1p was governed by the optimality of the transcript. In both replicates of the CLIP experiment, we see that Dhh1p is preferentially bound to low sTAI genes relative to higher sTAI genes (FIG. 10D).

The Number of Slow Moving Ribosomes Stimulates mRNA Decay

Figure 11A:
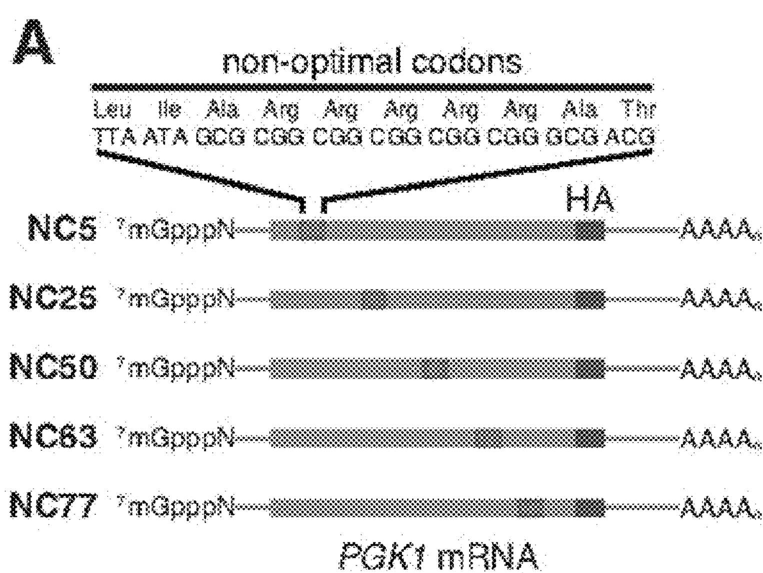
FIGS. 11(A-C) illustrate graphs and northern blots showing that Dhh1p senses the polarity of a stretch of non-optimal codons in an optimal mRNA. (A) Representation of PGK1 reporters with a stretch of 10 nonoptimal codons at increasing distances from the initiating AUG. NC: Non-optimal Codons; NC0: no stretch, NC5, 25, 50, 63, 77: Non-optimal Codon stretch 5, 25, 50, 63, 77% away from the AUG. (B) Northern blots of the different PGK1 reporters after GAL-transcriptional shut-off, showing the remaining mRNA at the indicated time-points after shut-off. (C) Half-lives of the different PGK1 reporters calculated from the northern blots (quantitation was normalized to SCR1, loading controls not shown), in WT and dhh1Δ cells.
Figure 17A:
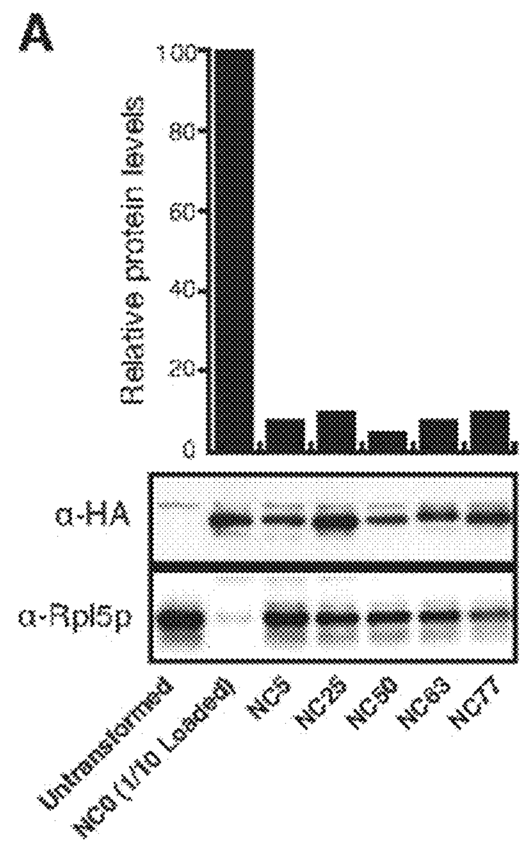
FIGS. 17(A-B) illustrate that the polarity of mRNA degradation is dependent on translation and ribosome association to the ORF upstream of the non-optimal stretch. All experiments were performed with the PGK1-HA reporters containing no stretch (NC0) or a stretch of non-optimal codons (NC) at a given distance from the AUG (5, 25, 50, 63, 77%). (A) Protein output of the different reporters was analyzed by Western blot; relative levels are plotted on the right. Rpl5p was probed as a loading control. (B) Relative levels of the PGK1 reporters in different strains deleted for essential factors involved in the ribosome quality control pathways.

We demonstrated above that the ratio of optimal to non-optimal codons is a key determinant in mRNA half-lives. And here we have shown that Dhh1p selectively binds mRNAs of low codon optimality and is critical in dictating codon-defined mRNA stability. A parsimonious explanation for these observations is that the density of slow moving ribosomes on an mRNA (dictated by codon optimality) is sensed by Dhh1p and communicated to the mRNA degradation machinery. We tested this idea by generating a series of reporters based on the highly optimal PGK1 mRNA where into each derivative we placed an identical stretch of 10 amino acids of exceptionally low sTAI (sTAI=0.101) at increasing distances from the initiating AUG (5%, 25%, 50%, 63%, and 77% away) (FIG. 11A). Importantly, the NC stretch is of sufficiently low sTAI that it is predicted to dramatically slow ribosomes at the site and in turn upstream; we see that protein expression is strongly and equivalently reduced for all five constructs to roughly 10% of that of the normal PGK1 mRNA (see FIG. 17A). As before, we monitored the mRNA half-lives of these reporters using a GAL-transcriptional shut-off approach. We observed a striking polarity for the overall half-lives of the mRNAs that scaled with the distance of the NC stretch from the AUG. Importantly, the polarity of RNA decay was abrogated on deletion of DHH1 (FIG. 11C). The least stable mRNA reporters are those with the NC stretch the furthest from the AUG start site where the maximal number of ribosomes would likely have accumulated on the ORF. These data indicate that the number of slow moving (or stalled) ribosomes is at a minimum correlated with the half-life of the mRNA.

Figure 12D:
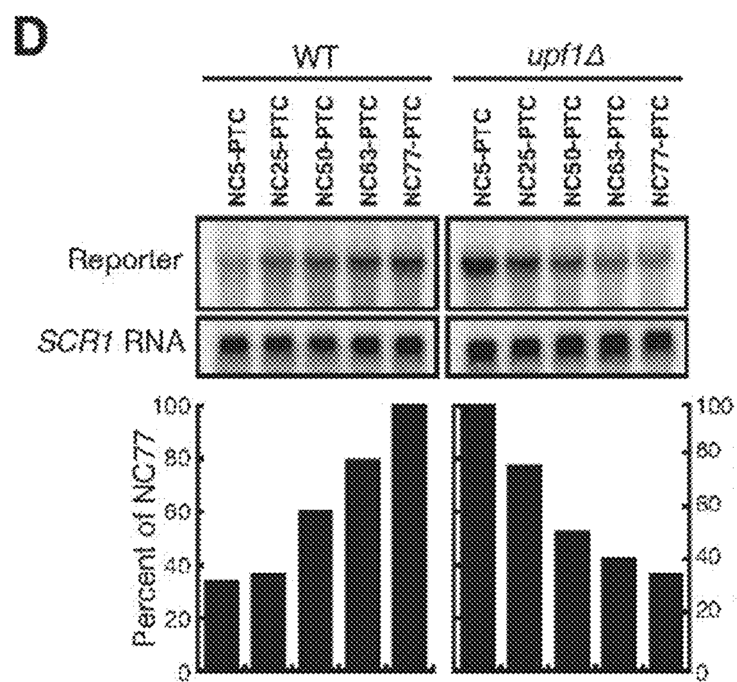
FIGS. 12(A-D) illustrate graphs and northern blots showing that Dhh1p mediated degradation is dependent on inefficient translation. (A) A stem loop (SL) was inserted in the 5'UTR of the previously described PGK1 reporters containing non-optimal codons at variable positions to inhibit translation. (B) Northern blot for steady-state abundance of the reporters with and without SL, and relative levels on the right. SCR1 was probed as a loading control. (C) A premature termination codon (PTC) was inserted immediately after the NC stretch of the reporters to prevent ribosome association downstream of the stretch. (D) Northern blot for steady-state abundance of the reporters with and without PTC, and relative levels below. SCR1 was probed as a loading control.

First, we verified that the polarity effect that we observed was dependent on mRNA translation by inserting a stem-loop inhibitory to translational initiation in the 5' UTR (FIG. 12A); indeed, inhibition of translation by the stem loop abrogated the influence of the NC stretch on mRNA decay (FIG. 12B). Second, we determined if the polarity effect resulted from ribosome events occurring upstream of the NC stretch or downstream. This idea was tested by placing a premature termination codon immediately after the NC stretch, such that once termination has occurred, ribosomes will no longer be associated downstream of the STOP codon (it follows that these ORFs are now very different in size) (FIG. 12C). In a WT yeast background, these reporters exhibit an inverse polarity for their stability, as anticipated from the impact of the nonsense mediated decay (NMD) pathway on their stability. However, when these same reporters are evaluated in a upf1Δ background, we see that the polarity of mRNA degradation is preserved (FIG. 12D). These data are consistent with models suggesting that ribosomes stacked upstream of slow codon regions are critical to defining the stability of the various reporter mRNAs.

Figure 17B:
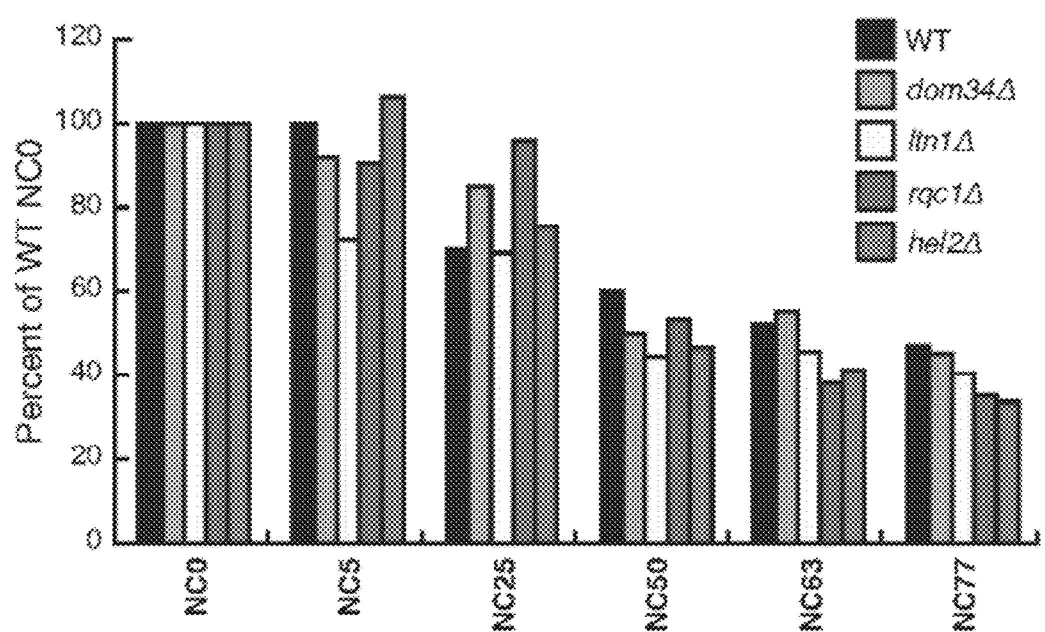

Lastly, there are numerous quality control mechanisms that exist within the cell to monitor aberrant translation events. As it is formally possibly that one of these QC pathways might recognize ribosomes stalled at non-optimal codons as aberrant, we asked whether the polarity effects that we observed resulted from the action of these pathways by performing the same analyses in different mutant backgrounds (dom34Δ, ltn1Δ, rqc1Δ, hel2Δ). Reassuringly, none of these components were observed to impact the polarity of mRNA decay observed in the reporter constructs (FIG. 17B).

Collectively, these data indicate that the polarity of mRNA degradation is translation-dependent and depends on ribosome-associated events localized between the AUG start site and the NC stretch. The simplest explanation for these observations is that the number of slow moving ribosomes on an mRNA determines the level of mRNA degradation observed.

Dhh1p Binds Physically to the Eukaryotic Ribosome

Figure 13A:
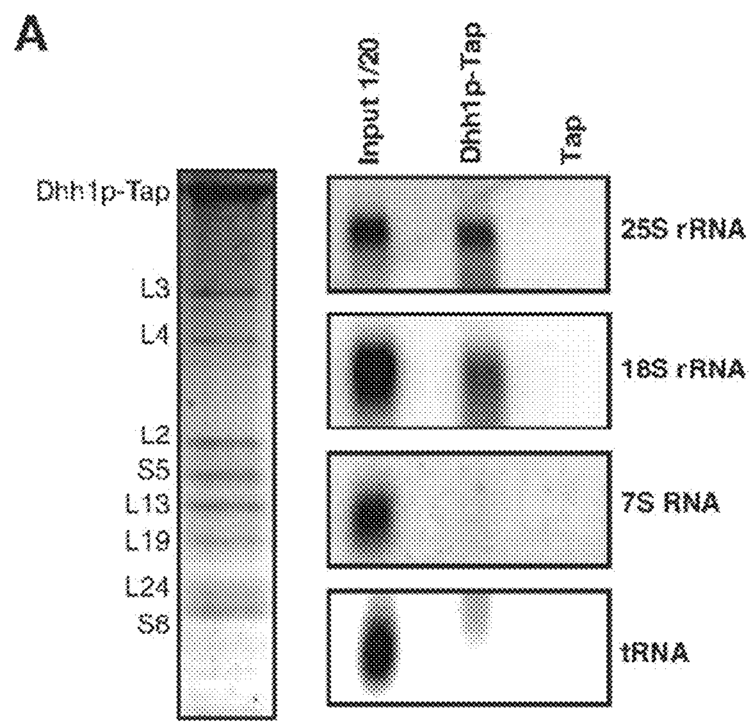
FIGS. 13(A-E) illustrate graphs and northern blots showing that Dhh1p binds ribosomes and preferentially modulates ribosome occupancy on mRNAs with low codon optimality. (A) Dhh1p-TAP purification followed by mass spectrometry (left, Coomassie blue gel staining) or Northern blots and specific probing for different rRNAs or tRNA (right). (B) Plotting the ribosome occupancy (average number of ribosomes per mRNA transcript) for mRNA transcripts under constitutive Dhh1p OE relative to WT conditions, binning transcripts by sTAI. Shown are two biological replicates. A two-tailed Mann-Whitney test shows that low optimality mRNAs (sTAI=0.25, Med.=1.30) have increased ribosome occupancy relative to high optimality mRNAs (sTAI=0.55, Med.=0.72), U=1364, p<2.2×10-16 upon Dhh1p overexpression (C) Quantifying the ribosome footprint density in the A-site under Dhh1p OE or dhh1Δ relative to WT. The identity of the codon in the A-site was determined by using 28-nt fragments as outlined previously (Ingolia et al., 2009). (D) Schematic of the reporter (SEQ ID NO: 33) used in polysome occupancy assays. (E) Northern blots were used to quantify the enrichment (relative fractional occupancy) of optimal and non-optimal HA-OST4 mRNA along a polysome gradient upon tethering catalytically active and inactive Dhh1p. Reported values are averaged across three samples and presented with standard error. Shown are representative northern blots for the non-optimal and optimal mRNAs upon tethering of catalytically active and inactive Dhh1p.

While CLIP data suggest that Dhh1p may directly bind to mRNA, thus dictating downstream functional consequences, it seems possible that like other DEAD-box helicases, Dhh1p could also interact directly with the ribosome to mediate function. We tested this hypothesis by using a tandem-affinity tag (TAP) to purify Dhh1p from yeast cells and identify associated complexes by mass-spec. Importantly, we observed eight prominent protein bands upon purification that we identified as ribosomal proteins (FIG. 13A). We next repeated our TAP purification and probed for specific RNA species by Northern blot. We observe that both the 25S and 18S rRNA co-purify with Dhh1p, while other transcripts such as the 7S RNA (SCR1) or tRNA do not. Together, these data indicate that Dhh1p physically interacts with the ribosome.

Ribosome Occupancy is Enhanced when Dhh1p is Bound

Given the connection that we have established between ribosome density and Dhh1p function in mRNA decay, we next asked whether on a global scale there is preferential effect of Dhh1p on the ribosome occupancy on mRNAs of low codon optimality. Ribosome profiling was performed in four *S. cerevisiae* strains, wild type, dhh1Δ (deletion) and constitutively overexpressed Dhh1p(OE) and Dhh1p-DQAD(OE). The DQAD allele has been previously shown to render Dhh1p nonfunctional. While an assessment of ribosome occupancy (the average number of ribosomes on a given transcript) between the four strains failed to reveal genes or ontological categories of interest, characterizing genes binned according to their overall optimality (sTAI) revealed interesting features.

In the Dhh1p(OE) strain, we see a clear pattern of increased ribosome occupancy on non-optimal genes (FIG. 13B). As a control we performed a similar analysis, measuring ribosome occupancy changes in the Dhh1p(OE) strain relative to the catalytically inactive Dhh1p protein (Dhh1p-DQAD(OE)). Again we observe enrichment of ribosomes on low optimality mRNAs, suggesting that this differential ribosome occupancy is dependent on the catalytic activity of Dhh1p (FIG. 18A).

We next took advantage of the nucleotide resolution of ribosome footprint profiling to see if increased occupancy on non-optimal genes could be resolved at the codon level. To perform this analysis, we looked at a subset of the reads from footprint profiling (28-nt fragments) in the mutant and wild type strains to characterize A-site occupancy. We find that when Dhh1p is overexpressed, relative to wild type, there is increased footprint density when non-optimal codons occupy the A site (FIG. 13C); no trends based on codon optimality are seen in the dhh1Δ strain.

We additionally profiled strains carrying tethered-reporter constructs. Here we use an mCherry reporter RNA (sTAI=0.422) tethered through a BoxB-Lambda N system to either Dhh1p or Dhh1p-DQAD. The Dhh1p tethered mCherry reporter mRNA exhibits 2.7-fold greater ribosome occupancy than the Dhh1p-DQAD tethered reporter (FIG. 18B) with reads distributed throughout the ORF. These data are consistent with the global analysis above and with earlier polysome profiling analysis.

We next probed the connection between ribosome occupancy, Dhh1p function, and codon optimality. We employed a similar tethering experiment, but using instead a short ORF (OST4) construct designed to allow for high resolution sucrose gradient analysis (FIG. 13D). We made synonymous variants of this ORF OST4 with either high optimality (sTAI=0.454) or low optimality (sTAI=0.203) and polysome evaluates. With this refinement, we could see differences in ribosome occupancy on ORFs as a function of codon optimality. Consistent with our model, we see a clear increase in ribosome occupancy on the HA-OST4-NON-OPT mRNA relative to the HA-OST4-OPT mRNA, dependent on the presence of functional Dhh1p (FIG. 13E).

Figure 14:
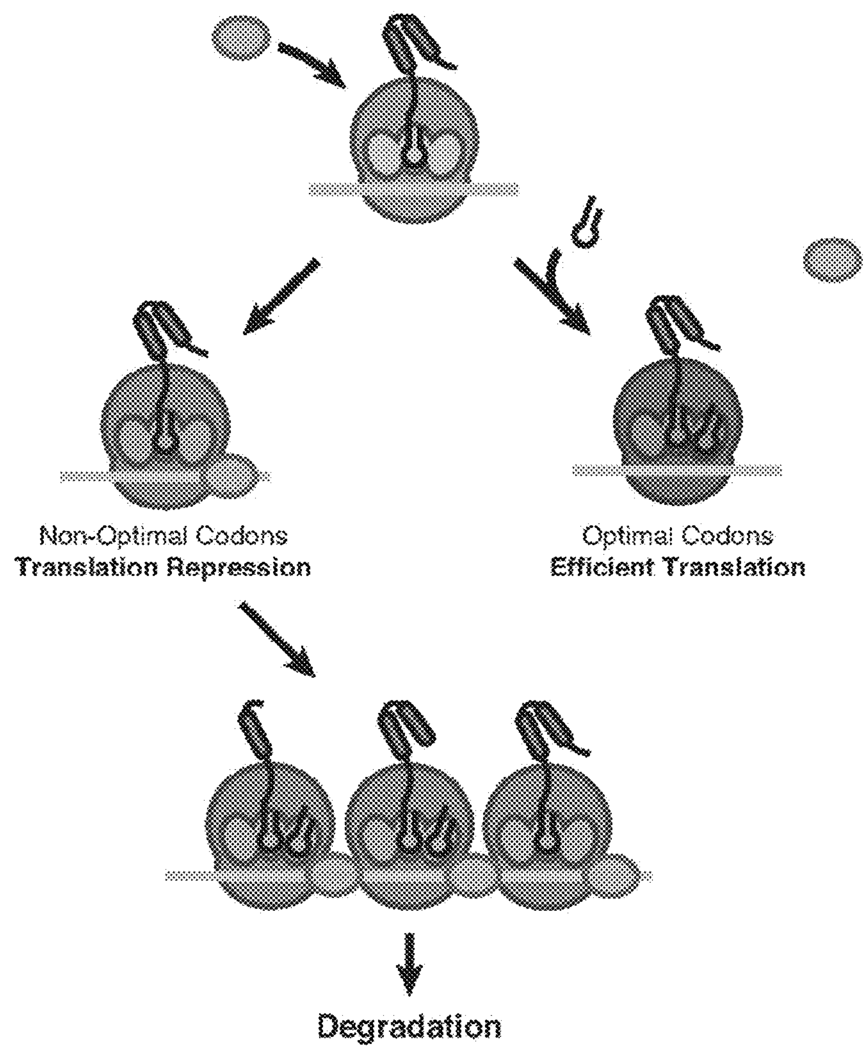
FIG. 14 illustrate a model showing Dhh1p is a general and essential sensor of ribosome speed during elongation. In this model, codon optimality influences the transit speed of ribosomes which in turns affects the association of the decay factor Dhh1p. Ribosomes are slowed down on non-optimal stretches, recruiting Dhh1p which may slow down ribosome movement further, and leads to mRNA decapping and degradation.

MRNA translation and mRNA stability are tightly coupled events, although it is unclear at a molecular level how these processes are connected. Above we established that codon usage strongly impacts both mRNA stability and translational elongation. In this study, we provide a mechanistic understanding of how the rates of translation are communicated to the mRNA degradation apparatus. We propose that the decapping activator and translational regulator Dhh1p is a sensor of ribosome speed across the transcriptome (FIG. 14). We hypothesize that Dhh1p dynamically samples elongation events, binding to the translating mRNPs (and ribosomes along it) when elongation is slow. Dhh1p's association with the translating mRNP may slow ribosome movement even further, leading ultimately to activation of mRNA decapping and degradation.

Dhh1p and Homologs are Implicated in Translational Control

A role for Dhh1p in regulating translation elongation is consistent with observations from other systems. For instance, in *Drosophila*, translationally repressed oskar and nanos mRNAs are found on polyribosomes in a so called "masked" state; the Dhh1p-homolog Me31b is required for their masking. Similarly, the Fragile X Mental Retardation Protein (FMRP), a polysome-associated neuronal RNA binding protein that interacts with Me31b was recently found to regulate translation by inducing stalling of ribosomes on target mRNAs. Given the high conservation and essential nature of Dhh1p in higher eukaryotes, it seems likely that such a critical role in modulating translational elongation is conserved throughout the eukaryotic lineage.

Dhh1p and homologs have also been implicated in the regulation of translational initiation. Recombinant Dhh1p in high concentrations inhibits 48S ribosome initiation complex formation in vitro. Moreover, multiple recent studies interested in miRNA-mediated regulation have implicated the mammalian Dhh1p homolog, DDX6, in interactions with the CCR4-NOT complex relevant to translational silencing; there is emerging consensus in this field that translational inhibition in these systems is imposed at the initiation step.

A role for Dhh1p in controlling translational initiation and elongation need not be mutually exclusive. Indeed, we have documented that Dhh1p directly contacts the ribosome (FIG. 13A). Thus the regulation of both elongation and initiation by Dhh1p may be a manifestation of the same molecular contacts with the ribosome itself. The seemingly distinct cellular responses may simply depend on the relative concentrations of the factor and the state of the ribosome being accessed (the kinetics and thermodynamics of the event). In higher eukaryotes, recent findings suggest that the basis for these disparate cellular roles may lie in the complex macromolecular associations that the DDX6-CCR4-NOT complex makes with downstream effector proteins. Detailed understanding of the molecular contacts of Dhh1p with the ribosome may ultimately reconcile these apparent discrepancies.

Normal mRNA Decay is a Response to Subtle Changes in Translation Rate

It is well established that the ribosome is centrally involved in specifying mRNA degradation on aberrant transcripts. The processes of Nonsense-Mediated Decay (NMD), No-Go Decay (NGD), and Non-Stop Decay (NSD) all are dictated by abnormal events on the ribosome within the ribosomal A site (i.e., a premature termination codon, a truncated mRNA or a string of AAA (lysine) codons). Importantly, however, a direct connection between ribosome function and normal mRNA decay has not been established. Our data here provide clear evidence for an intimate connection between efficient translation of mRNAs by ribosomes and normal mRNA decay mediated by the DEAD-box helicase Dhh1p. Given that the main function of an mRNA is the production of protein product through translation, such a central role for the ribosome in specifying its stability is reassuring.

From the above description of the invention, those skilled in the art will perceive improvements, changes and modifications Such improvements, changes and modifications are within the skill of the art and are intended to be covered by the appended claims. All publications, patents, and patent applications cited in the present application are herein incorporated by reference in their entirety.

Having described the invention, the following is claimed:

1. A method of modulating the expression of a recombinant protein in a host cell, the method comprising:

identifying optimal and non-optimal codons in a wild type cDNA sequence that encodes the protein, preparing a synthetic cDNA sequence by replacing one or more of the optimal codons of the wild type cDNA with a non-optimal codon encoding the same amino add as the replaced optimal codon or replacing one or more of the non-optimal codons of the wild type cDNA with an optimal codon encoding the same amino add as the replaced non-optimal codon, transfecting the host cell with the synthetic cDNA, wherein the replacement of the one or more codons from the cDNA sequence enhances expression of the recombinant protein in the host cell at least about 10% compared to the nucleic sequence prior to replacement, wherein the one or more optimal codons are selected from the group consisting of pct (Alanine), ggt (Glycine), gtc (Valine), ttg (Leucine), gtt (Valine), gcc (Alanine), cca (Proline), act (Threonine), tct (Serine), tcc (Serine), acc (Threonine), atc (Isoleucine), aag (Lysine), tac (Tyrosine), ttc (Phenylalanine), gaa (Glutamic Acid), cgt (Arginine), caa (Glutamine), cac (Histidine), aac (Asparagine), gac (Aspartic Add), att (Isoleucine), aga (Arginine), and tgt (Cysteine); and the one or more non-optimal codons are selected from the group consisting of cct (Proline), ggc (Glycine), igg (Tryptophan), tta (Leucine), gat (Aspartic Add), atg (Methionine), ttt (Phenylalanine), tgc (Cysteine), cat (Histidine), gca (Alanine), tat (Tyrosine), ccc (Proline), ggg (Glycine), gtg (Valine), gcg (Alanine), cgc (Arginine), tca (Serine), gag (Glutamic Acid), gga (Glycine), tcg (Serine), cgg (Arginine), aat (Asparagine), ctt (Leucine), cta (Leucine), cag (Glutamine), ctc (Leucine), aca (Threonine), age: (Serine), aaa (Lysine), agt (Serine), acg (Threonine), ctg (Leucine), ccg (Proline), gta (Valine), agg (Arginine), cga (Arginine), and ata (isoleucine), and expressing the recombinant protein.

2. The method of claim 1, wherein one or more of the non-optimal codons is replaced with an optimal codon encoding the same amino acid as the replaced one or more non-optimal codons so that the synthetic cDNA sequence has more than about 70% optimal codons.

3. The method of claim 1, wherein the cell is a yeast cell.

4. The method of claim 1, wherein the cell is a mammalian cell.

5. The method of claim 1, wherein the cell is transfected with a vector including the synthetic cDNA.

6. The method of claim 5, wherein the vector is a mammalian expression vector.

* * * * *

SEQUENCE LISTING

```
<160> NUMBER OF SEQ ID NOS: 33

<210> SEQ ID NO 1
<211> LENGTH: 1650
<212> TYPE: DNA
<213> ORGANISM: Saccharomyces cerevisiae

<400> SEQUENCE: 1

atggcacgcc agaaaatgtt ttataataaa ttactcggca tgctcagcgt aggatttggg      60

tttgcatggg cgctcgagaa tataacgata tatgaatttg actttggcaa aggcatactc     120

gatcaaagct acggcggagt attttcaaat aatggccctt cgcaagtgca gctgcgggat     180

gcagtcctca tgaatgggac agtggtatat gattcaaatg gcgcgtggga tagtagtgcg     240

ctggaggagt ggctccaggg acagaaaaaa gtttcgatag agaaaatatt tgagaatata     300

gggcccagcg cggtgtatcc gtcgatatcg cctggggtag tgatagcgtc accctcgcag     360

acgcatccgg attattttta tcagtggata agggatagcg cgttgacgat aaacagtata     420

gtgtctcatt cagcgggccc ggcaatagag acgttactac agtatctgaa cgtatcattt     480

catctacagc gcagcaataa tacattgggc gcaggcatag gctacactaa tgatacagtg     540

gcattgggag atcctaaatg gaatgtggat aatacggcat ttacggagga ttgggggagg     600

cctcagaatg atgggcctgc acttcgaagc atagcaatat taaaaataat agattatata     660

aaacagtctg gcacggatct gggggccaaa taccctttc agagcacggc agatatcttt     720

gatgatattg tacgatggga tctgaggttc attatagatc attggaattc ttcaggattt     780

gatctatggg aggaagtaaa tggcatgcat tttttactt tactggtaca gctgtctgca     840

gtggataaat cgctgtcgta ttttaatgcc tcagagcggt cgagcccctt tgtggaagag     900

ttgcggcaga cacgccggga tataagtaaa tttttagtgg atcctgcgaa tgggtttatc     960

aatggcaaat ataattatat agtagggaca cccatgatag ccgacacact caggagtgga    1020

ctggatataa gtactttatt agcggcgaat accgtgcatg atgcgccttc tgcgtcacat    1080

cttccgttcg atataaatga tcctgcagtc ctgaatacgc tgcatcatct aatgttacat    1140

atgcggtcga tatatcccat aaatgatagc tcaaaaaatg caacggggat tgcgctgggc    1200

cggtatcctg aggatgtata tgatggatat ggctttggcg agggaaatcc ctgggtactg    1260

gcaacgtgca cggcatcaac aacgctttat cagctcatat atcgacatat atctgagcag    1320

catgacctcg tggtcccaat gaataatgat tgctcgaatg cattttggag cgagctggta    1380

tttagtaatc tcacgacttt aggaaatgat gagggctatt tgattttgga gttcaataca    1440

cctgcgttca atcaaacaat acagaaaata tttcagctag ctgattcatt tctggtcaaa    1500

ctgaaagctc atgtgggaac agatggggag ctaagtgagc agtttaataa atacacaggg    1560
```

```
tttatgcagg gagcccagca ccttacatgg tcatatacgt cattttggga tgcatatcag   1620

atacgccagg aggtgttaca gagtctttag                                     1650
```

<210> SEQ ID NO 2
<211> LENGTH: 1650
<212> TYPE: DNA
<213> ORGANISM: Saccharomyces cerevisiae

<400> SEQUENCE: 2

```
atggcacgcc aaaagatgtt ttataacaaa ttactcggca tgctcagcgt aggatttggg     60
tttgcttggg cgctcgagaa tattactata tatgaatttg attttggcaa gggcatactc    120
gatcaaagct acggcggtgt attttcaaat aatggccctt cgcaggtgca gctgcgggat    180
gcagtgctga tgaatgggac agtggtatat gattcaaacg gcgcatggga tagtagtgcg    240
ctggaggagt ggctccaggg acagaaaaaa gtatcaatcg aaaaaatatt tgaaaatata    300
gggcccagcg cggtgtatcc gtctatttcg cctggggtgg tgattgcgtc accgtcgcag    360
acgcatccgg actactttta tcaatggata agggacagcg cgttgacgat aaatagtatt    420
gtgtctcatt cggcgggccc ggcaatagag acgttattgc agtatctgaa cgtttcattc    480
catttgcagc gaagcaacaa cacattaggc gcgggcattg gttacacgaa tgatacagtg    540
gcattgggag atcctaaatg gaatgtcgat aacacggcgt tcacggaaga ttggggccgg    600
cctcagaatg atgggcctgc gcttcgaagc atagccatat taaaaataat cgattatata    660
aagcaatcgg gcacagatct gggggcaaaa tatccatttc agagcaccgc agatatattt    720
gatgatattg tacgctggga tctgaggttt attattgatc attggaattc gtcgggattt    780
gatctatggg aggaagtcaa tggcatgcat ttttttactt tactggtaca gctgtcagca    840
gtggacaagt cgctgtcgta ttttaacgcg tcagagcggt cgagtccctt tgttgaagaa    900
cttcgccaga cacgccggga tataagtaaa tttttagtgg atcctgcgaa tgggtttata    960
aatggcaagt ataattatat tgttgggaca cccatgatag cggacacatt gagatccgga   1020
ctggacataa gcactttatt agcggcgaat accgtgcacg atgcgccctc tgcttcccat   1080
cttccgtttg atataaatga ccctgccgtc ctgaatacgt tgcaccattt aatgttgcat   1140
atgaggtcga tatatcccat caatgatagc tccaaaaatg caacgggcat agccctgggc   1200
cggtatcctg aggatgtata tgatggatat ggctttggcg agggaaatcc ctgggtgctg   1260
gcaacgtgta ccgcgtcaac aacgctttat cagctcattt acagacacat ctcagagcag   1320
catgacctag ttgtaccaat gaacaacgat tgctcgaatg cattttggag cgagctggta   1380
ttctccaatc tcacgacact gggaaatgat gagggctatc tcatactgga gttcaataca   1440
cctgccttta atcagaccat acagaaaatc ttccagctag cggattcatt tcttgtgaaa   1500
ctgaaagctc atgtgggaac agatggggaa ctaagtgagc agtttaacaa atatacaggg   1560
tttatgcagg gtgcgcaaca ccttacgtgg agttatacgt cattctggga tgcgtatcaa   1620
atacgacagg aggttttaca gagtttgtag                                     1650
```

<210> SEQ ID NO 3
<211> LENGTH: 1650
<212> TYPE: DNA
<213> ORGANISM: Saccharomyces cerevisiae

<400> SEQUENCE: 3

```
atggcaagac agaagatgtt ttataacaaa ttactcggca tgctcagcgt aggatttggg     60
tttgcttggg cgctcgagaa cattacgata tacgaatttg actttggcaa gggcatactc    120
```

```
gatcagagct acggcggtgt attttcaaac aacggccctt cgcaagtgca gctgcgggat    180
gcagtcttga tgaatgggac agtggtatac gattcaaacg gcgcttggga cagtagtgcg    240
ctggaggaat ggctccaggg acagaaaaaa gtgagtatcg aaaaaatatt tgaaaatatt    300
gggcccagcg ccgtgtatcc gagcatttcg cctggggtcg tgatagcgtc accttcgcaa    360
acgcatcctg attacttcta ccaatggata agggatagcg cgttgacgat aaatagtatt    420
gtctctcatt ctgcgggccc ggcaatagag acgttacttc agtatctgaa cgtgtcattc    480
cacttgcaaa gaagcaacaa cacactcggc gctggcatag gttatactaa tgatacagtg    540
gctttgggag accctaagtg gaacgtggac aacacggctt tcacggagga ttggggccgt    600
cctcaaaacg atgggcctgc tcttcgaagc atagccatct taaaaatcat agactacata    660
aagcagagcg gcacagatct gggggccaag tatccgtttc agtccacggc agatatcttt    720
gatgatattg tacgttggga cctgaggttc attattgacc actggaattc ttccggattt    780
gatctatggg aggaggtaaa tggcatgcat ttctttactt tactggtaca actgagtgca    840
gtggacaaat cgctgtcgta ttttaacgcg tcagagcggt cgtctccctt tgtggaagaa    900
ttgcgtcaga cacgccggga catatccaag tttttagtgg accctgcgaa tgggtttatc    960
aatggcaaat ataattatat tgtggggaca cccatgatag cagatacatt gagatccgga   1020
ctggatatat ccacattatt agctgcgaac accgtgcacg atgcgccatc tgctagtcat   1080
cttccgttcg atatcaatga ccctgccgta ctgaatacgt tgcaccatct aatgctacac   1140
atgaggtcga tatatcccat aaacgatagc tcaaaaaatg caacgggtat agccctgggc   1200
cggtatcctg aggatgtata tgatggatat ggctttggcg agggaaatcc ctgggtcctg   1260
gcaacgtgca ccgcttcaac aacgctttat cagctcattt acagacacat ctctgagcag   1320
catgacttgg tagtcccaat gaacaacgat tgttcgaacg cattttggag cgagctggta   1380
tttagcaacc tcacgactct gggaaatgac gaaggctatt taatattgga gttcaataca   1440
cctgccttca atcagaccat acaaaaaata ttccagctag ctgattcatt cttggtaaag   1500
ctgaaagcgc atgtgggaac agatggggaa ctaagtgaac aatttaacaa atatacaggg   1560
tttatgcagg gcgcccagca ccttacgtgg agctatactt cattttggga tgcgtatcaa   1620
ataagacaag aagttttaca gagtttgtag                                    1650
```

<210> SEQ ID NO 4
<211> LENGTH: 1650
<212> TYPE: DNA
<213> ORGANISM: Saccharomyces cerevisiae

<400> SEQUENCE: 4

```
atggcaagac aaaagatgtt ttataacaaa ttactcggca tgctcagcgt aggatttggg     60
tttgcttggg cgctcgagaa cattactata tatgaatttg actttggcaa gggcattctc    120
gatcaaagct acggcggagt attttcaaac aacggccctt cgcaagtgca gctgcgggat    180
gcagtcttga tgaatgggac agtggtatat gattcaaacg gcgcttggga cagtagtgcg    240
ctggaggagt ggctccaggg acagaaaaaa gtttccatcg aaaaaatatt tgaaaatatt    300
gggcccagcg ccgtgtatcc gtctatttcg cctggggtgg tgatagcgtc accatcgcaa    360
acgcatccag actacttcta ccaatggata agggacagcg cgttgacgat aaacagtata    420
gtctctcatt ctgcgggccc ggcaatagag acgttattgc agtatctgaa tgtttcattt    480
cacttgcaaa gaagcaataa cacattgggc gctggcattg gttacactaa cgatacagtg    540
```

```
gctttgggag atcctaagtg gaacgtcgac aacacggctt tcacggaaga ttggggtcgt    600

cctcaaaacg atgggcctgc tcttcgaagc attgcgatat taaaaatcat cgactacatc    660

aagcaatctg gcactgatct gggggccaaa tacccgttcc agtccaccgc agatatcttt    720

gatgatattg tacgttggga cctgaggttc attatagacc actggaattc ttccggattt    780

gatctatggg aggaagtcaa tggcatgcat ttctttactt tactggtaca actgtctgca    840

gtggacaagt cgctgtcgta ttttaacgcc tcagaacggt cgtctccctt tgttgaagaa    900

ttgcgtcaga cacgccggga catctcaaag tttttagtgg atcctgcgaa tgggtttatc    960

aacggcaagt acaattatat tgttgggaca cccatgattg ccgatacatt gagatccgga   1020

ctggacatat ccactttatt agctgcgaac acagtccacg atgcgccatc tgcttcccat   1080

cttccgttcg atatcaatga ccctgccgtc ctgaacacgt tgcaccattt gatgttgcac   1140

atgcgttcga tatatcccat caacgatagc tccaaaaatg caacgggtat agccctgggc   1200

cggtatcctg aggacgtata tgatggatat ggctttggcg agggaaatcc ctgggtcctg   1260

gccacgtgta ccgcttcaac aacgctttat cagctcatat acagacacat ctctgagcag   1320

catgacttgg ttgtcccaat gaacaacgat tgttcgaatg cattttggag cgagctggta   1380

ttctccaacc tcacgacttt gggaaatgac gaaggctatt tgattttgga gttcaataca   1440

cctgccttca atcaaaccat acaaaaaatc ttccagctag ctgattcatt cttggtcaag   1500

ctgaaagctc acgtgggaac agatggggaa ctaagtgagc aatttaacaa atacacaggg   1560

tttatgcagg gtgcccaaca ccttacctgg tcctatactt cattctggga tgcctatcag   1620

ataagacaag aagttttaca gagtttgtag                                    1650
```

<210> SEQ ID NO 5
<211> LENGTH: 1650
<212> TYPE: DNA
<213> ORGANISM: Saccharomyces cerevisiae

<400> SEQUENCE: 5

```
atggcaagac aaaagatgtt ttataacaaa ttgctcggca tgctcagcgt aggattcggg     60

tttgcttggg cgctcgagaa cattactata tacgaatttg actttggcaa gggtattttg    120

gatcaaagct acggcggtgt attttcaaac aacggccctt cgcaagtgca gctgcgggat    180

gcagtcttga tgaatgggac agtggtatac gattccaacg gtgcttggga cagtagtgcg    240

ctggaggaat ggttgcaggg acagaaaaaa gtttccatcg aaaaaatatt tgaaaatatt    300

gggcccagcg ccgtgtatcc gtctatttcg cctggggtcg tgattgcgtc accatcgcaa    360

acgcatccag actacttcta ccaatggata agggacagcg ctttgacgat aaacagtatt    420

gtctctcact ctgcgggccc ggcaatagag acgttattgc agtacctgaa cgtttcattc    480

cacttgcaaa gaagcaacaa cacattgggc gctggcattg gttacactaa cgatacagtg    540

gctttgggag accctaagtg gaacgtcgac aacacggctt tcacggaaga ttggggtcgt    600

cctcaaaacg atgggcctgc tcttcgatcc attgccatct taaaaatcat cgactacatc    660

aagcaatctg gcactgatct gggggccaag tacccattcc agtccaccgc agatatcttt    720

gatgacattg tacgttggga cttgaggttc attattgacc actggaattc ttccggattt    780

gatctatggg aggaagtcaa tggtatgcat ttctttactt tactggtaca actgtctgct    840

gtggacaagt cgctgtcgta ttttaacgcc tcagaacggt cgtctccctt tgttgaagaa    900

ttgcgtcaaa ctcgccggga catctccaag tttttagtgg accctgcgaa tgggtttatc    960

aacggcaagt acaattatat tgttggtaca cccatgattg ccgacacatt gagatccgga   1020
```

```
ctggacatat ccactttgtt agctgcgaac accgtccacg atgcgccatc tgcttcccat   1080

cttccgttcg atatcaatga ccctgccgtc ctgaacacgt tgcaccattt gatgttgcac   1140

atgcgttcga tataccccat caacgattct tccaaaaatg caacgggtat tgccctgggc   1200

cggtatcctg aggacgtata cgatggatat ggctttggtg agggaaatcc ctgggtcctg   1260

gccacgtgta ccgcttcaac aacgctttat cagctcattt acagacacat ctctgagcag   1320

catgacttgg ttgtcccaat gaacaacgat tgttcgaacg cattttggag cgagctggta   1380

ttctccaacc tcacgacttt gggaaatgac gaaggctatt tgattttgga gttcaataca   1440

cctgccttca atcaaaccat acaaaaaatc ttccaactag ctgattcatt cttggtcaag   1500

ctgaaagctc acgtgggaac agacggggaa ctaagtgaac aattcaacaa atacacaggg   1560

tttatgcagg gtgcccaaca ccttacctgg tcctatactt cattctggga cgcctatcaa   1620

attagacaag aagttttaca gagtttgtag                                    1650
```

```
<210> SEQ ID NO 6
<211> LENGTH: 1650
<212> TYPE: DNA
<213> ORGANISM: Saccharomyces cerevisiae

<400> SEQUENCE: 6

atggctagac aaaagatgtt ttataacaaa ttgttgggca tgctcagcgt aggtttcggg     60

tttgcttggg cgctcgaaaa cattactata tacgaatttg actttggcaa gggtattctc    120

gatcaaagct acggcggtgt attttcaaac aacggccctt ctcaagtgca gctgcgggac    180

gcagtcttga tgaatggtac tgtggtatac gattcaaacg gtgcttggga cagtagtgcg    240

ctggaggaat ggttgcaggg tcagaaaaaa gtttccatcg aaaaaatatt cgaaaacatt    300

gggcccagcg ccgtgtaccc gtctatttcg ccaggggtcg tgattgcgtc accatcgcaa    360

acgcatccag actacttcta ccaatggata agggacagcg cgttgacgat taacagtatt    420

gtctctcatt ctgccggccc ggcaattgag acgttattgc agtacttgaa cgtttcattc    480

cacttgcaaa gaagcaacaa cactttgggc gctggcattg gttacactaa cgatactgtg    540

gctttgggag acccaaagtg gaacgtcgac aacacggctt tcaccgaaga ttggggtcgt    600

cctcaaaacg atgggccagc tcttcgaagc attgccatct taaagatcat cgactacatc    660

aagcaatctg gtactgattt gggggccaag tacccattcc aatccaccgc agatatcttt    720

gacgatattg tacgttggga cctgaggttc attattgacc actggaattc ttccggattt    780

gatctatggg aggaagtcaa tggcatgcat ttcttcactt tgctggtaca actgtctgca    840

gtcgacaagt cgctgtcgta tttcaacgcc tctgaacgtt cttctccctt tgttgaagaa    900

ttgcgtcaga cacgccggga catctccaag ttcttggtcg accctgcgaa tgggttcatc    960

aacggcaagt acaattatat tgttgggaca cccatgattg ccgacacatt gagatccgga   1020

ctggacatat ccactttatt agctgccaac accgtccacg acgcgccatc tgcttcccat   1080

cttccgttcg atatcaatga ccctgccgtc ttgaacacgt tgcaccattt gatgttgcac   1140

atgcgttcga tataccccat caacgacagc tccaaaaacg caacgggtat tgccctgggc   1200

cggtatcctg aggacgtata tgatggttat ggttttggcg agggaaaccc ctgggtcctg   1260

gccacgtgta ccgcttccac cactctttat caattgattt acagacacat ctctgagcaa   1320

catgacttgg ttgtcccaat gaacaacgac tgttcgaacg cattttggag cgagctggta   1380

ttctccaacc tcaccacttt gggtaacgac gaaggctatt tgattttgga gttcaacaca   1440
```

```
cctgccttca accaaaccat acaaaaaatc ttccaattgg ctgattcatt cttggtcaag   1500

ctgaaagctc acgtgggaac cgacggtgaa ctaagtgaac aattcaacaa gtacacaggg   1560

tttatgcaag gtgcccaaca ccttacctgg tcctatactt cattctggga cgcctaccaa   1620

ataagacaag aagttttaca gagtttgtag                                    1650
```

<210> SEQ ID NO 7
<211> LENGTH: 1650
<212> TYPE: DNA
<213> ORGANISM: Saccharomyces cerevisiae

<400> SEQUENCE: 7

```
atggctagac aaaagatgtt ctataacaaa ttgttgggta tgttgagcgt aggattcggg     60

tttgcttggg cgttggaaaa cattactata tacgaatttg acttcggcaa gggtattttg    120

gatcaatctt acggtggtgt tttttccaac aacggtcctt cgcaagtcca gttgagagat    180

gccgtcttga tgaatgggac tgtggtatac gattctaacg gcgcttggga cagtagtgcg    240

ctggaggaat ggttgcaagg acagaagaaa gtttccatcg aaaaaatatt tgaaaacatt    300

ggtcccagcg ccgtgtatcc gtctatttcg ccaggggtcg tgattgcgtc accatcgcaa    360

acgcacccag actacttcta ccaatggatt cgtgactctg ctttgacgat aaactctatt    420

gtctctcatt ctgcgggccc ggccattgag acgttattgc agtacttgaa cgtttccttc    480

cacttgcaaa gatctaacaa cacattgggc gctggtattg gttacactaa cgatactgtg    540

gctttgggag accctaagtg gaacgtcgac aacacggctt tcactgaaga ttggggtcgt    600

ccacaaaacg acggtcctgc tttgagatct attgccatct taaagatcat cgactacatc    660

aagcaatctg gtactgatct gggtgccaag tacccattcc agtccaccgc agacatcttc    720

gatgacattg tacgttggga cttgaggttc attattgacc actggaactc ttccggattt    780

gatttgtggg aggaagtcaa cggcatgcat ttcttcactt tgttggtaca attgtctgcc    840

gtggacaagt ctttgtccta ttttaacgcc tcagaacggt cgtctccctt cgttgaagaa    900

ttgcgtcaaa ctcgccgtga catctccaag tttttggtgg acccagcgaa tggtttcatc    960

aacggcaagt acaattacat tgttgggaca cccatgattg ccgacacatt gagatccggt   1020

ttggacatct ccactttgtt agctgcgaac accgtccacg acgcgccatc tgcttcccat   1080

ttgccgttcg acatcaatga cccagccgtc ttgaacacct tgcaccactt gatgttgcac   1140

atgcgttcga tctaccccat caacgattcc tccaagaatg ccacgggtat tgccctgggc   1200

cggtatccag aagacgtcta tgatggatat ggttttggcg agggaaaccc ctgggtcctg   1260

gccacctgta ccgcttcaac cacgttgtat cagctcattt acagacacat ctctgaacag   1320

cacgacttgg ttgtcccaat gaacaacgac tgttctaacg ccttttggtc tgaactggtc   1380

ttctccaacc tcaccacttt gggtaacgac gaaggctact tgattttgga attcaataca   1440

ccagccttca atcaaaccat acaaaaaatc ttccaactag ctgattcctt cttggtcaag   1500

ctgaaggctc acgtgggaac cgacggtgaa ctaagtgaac aatttaacaa atacacaggt   1560

tttatgcagg gtgcccaaca cttgacctgg tcctatactt cattctggga tgcctatcaa   1620

attagacaag aagttttgca gagtttgtag                                    1650
```

<210> SEQ ID NO 8
<211> LENGTH: 1650
<212> TYPE: DNA
<213> ORGANISM: Saccharomyces cerevisiae

<400> SEQUENCE: 8

```
atggctagac aaaagatgtt ttataacaaa ttattgggta tgttgtctgt aggtttcggt     60

tttgcttggg ccttggaaaa cattactatc tacgaatttg actttggtaa gggtattttg    120

gaccaatctt acggtggtgt cttttcaaac aacggtcctt ctcaagtcca attgagagat    180

gccgtcttga tgaatgggac agtggtctac gactcaaacg gtgcttggga cagttccgcg    240

ctggaagaat ggctccaggg tcaaaagaag gtttccatcg aaaaaatctt cgaaaacatt    300

ggtccctccg ccgtctaccc gtctatttcg cctggggtcg ttattgcgtc tccatcccaa    360

actcacccag actacttcta ccaatggata cgtgacagcg cgttgactat aaactctatt    420

gtctctcact ctgcgggtcc ggctatagag actttgttgc aatacttgaa cgtttccttc    480

cacttgcaaa gaagcaacaa cactttgggt gctggcattg gttacactaa cgacacagtg    540

gctttgggtg acccaaagtg gaacgtcgac aacacggctt tcaccgaaga ctggggtcgt    600

ccacaaaacg atgggccagc tttgcgatcc attgccatct tgaaaatcat cgactacatc    660

aagcaatctg gcactgactt gggggccaag tacccattcc aatccaccgc agacatcttt    720

gacgacattg tacgttggga cttgagattc attattgacc actggaactc ttccggtttt    780

gatttgtggg aggaagtcaa tggtatgcac ttcttcactt tgctggtcca attgtctgct    840

gtcgacaagt ctttgtccta cttcaacgcc tcagaacgtt cgtctccatt tgttgaagaa    900

ttgcgtcaga ccagaagaga catctccaag tttttagtcg acccagccaa tggtttcatc    960

aacggtaagt acaactatat tgttggtact cccatgattg ccgacacttt gagatccgga   1020

ttggacatat ccactttatt agctgctaac accgtccacg atgcgccatc tgcttcccac   1080

ttgccattcg atatcaatga cccagccgtc ttgaacactt tgcaccactt gatgttgcac   1140

atgcgttcca tatacccaat caacgacagc tccaaaaatg caactggtat tgccttgggt   1200

cgttaccctg aggacgtata cgacggatac ggtttcggcg agggtaaccc atgggtcttg   1260

gccacgtgta ccgcttccac tactctttac caattgattt acagacacat ctctgaacag   1320

cacgacttgg ttgtcccaat gaacaacgat tgttctaacg ctttctggtc cgaattggta   1380

ttctccaact tgacgacttt gggtaacgac gaaggttatt tgattttgga attcaacact   1440

ccagccttca accaaaccat acaaaaaatc ttccaattgg ctgactcttt cttggtcaag   1500

ctgaaggctc acgtgggaac agacggtgaa ctaagtgaac aatttaacaa atacacaggg   1560

ttcatgcaag gtgcccaaca cttgacctgg tcctacactt ctttctggga cgcctaccaa   1620

attagacaag aagttttgca atccttgtag                                    1650
```

<210> SEQ ID NO 9
<211> LENGTH: 1650
<212> TYPE: DNA
<213> ORGANISM: Saccharomyces cerevisiae

<400> SEQUENCE: 9

```
atggcaagac aaaagatgtt ctacaacaag ttgttgggta tgttgtccgt tggtttcggt     60

ttcgcttggg ccttggagaa cattactatt tacgaattcg actttggtaa gggcattttg    120

gatcaatctt acggtggtgt cttctccaac aacggtccat ctcaagtcca actgagagac    180

gctgtcttga tgaatggtac tgtggtatac gattccaacg gcgcttggga cagttctgcc    240

ctggaagaat ggttgcaggg acaaaagaaa gtttccatcg aaaaaatctt cgaaaacatt    300

ggtccatccg ccgtctaccc atctatttcg ccaggtgtcg tcattgcttc accatcccaa    360

acccacccag actacttcta ccaatggatc cgtgactccg ccttgactat caactccatt    420
```

```
gtctctcact ctgctggtcc agccatcgaa actttgttgc aatacctgaa cgtttccttc    480

cacttgcaaa gatctaacaa cactttgggt gctggtattg gttacactaa cgacactgtt    540

gctttgggag acccaaagtg gaacgtcgac aacaccgctt tcactgaaga ctggggtcgt    600

ccacaaaacg acggtccagc tttgagatcc attgccatct tgaaaatcat cgactacatc    660

aagcaatctg gcactgactt gggtgccaag tacccattcc aatccaccgc agatatcttc    720

gacgacattg tccgttggga cttgagattc attattgacc actggaactc ttccggtttc    780

gacttgtggg aagaagtcaa cggtatgcac ttcttcactt tattggtcca attgtctgcc    840

gttgacaagt ccttgtctta cttcaacgcc tctgaacgtt cttctccatt cgttgaagaa    900

ttgcgtcaaa caagacgtga catctccaag ttcttggttg acccagctaa cggtttcatc    960

aacggtaagt acaactacat tgttggtacc ccaatgattg ccgacacctt gagatccgga   1020

ctggacatat ccactttgtt ggctgcgaac accgtccacg acgcccatc tgcttcccac    1080

ttgccattcg acatcaatga ccctgccgtc ttgaacactt tgcaccactt gatgttgcac   1140

atgcgttcta tctaccccat caacgactct tccaagaacg ctactggtat tgccttgggt   1200

agatacccag aagacgttta cgacggttac ggttttggtg agggtaatcc atgggtcttg   1260

gccacctgta ccgcttccac tactttgtac caattgattt acagacacat ctctgaacaa   1320

cacgacttgg ttgtcccaat gaacaacgac tgttcgaacg ctttctggtc tgaactggtt   1380

ttctccaacc tcaccacttt gggtaacgac gaaggttact tgattttgga attcaatacc   1440

ccagccttca accaaaccat tcaaaaaatc ttccaactag ctgactcctt cttggtcaag   1500

ttgaaggctc acgtgggtac tgacggtgaa ctaagtgaac aattcaacaa gtacaccggt   1560

ttcatgcaag gtgcccaaca cttgacctgg tcctatactt cattctggga tgcctaccaa   1620

atcagacaag aagttttaca aagtttgtag                                    1650
```

```
<210> SEQ ID NO 10
<211> LENGTH: 1650
<212> TYPE: DNA
<213> ORGANISM: Saccharomyces cerevisiae

<400> SEQUENCE: 10

atggccagac aaaagatgtt ctacaacaag ttgttgggta tgttgtccgt cggtttcggt     60

ttcgcttggg ctttggaaaa cattactatt tacgaattcg acttcggtaa gggtattttg    120

gaccaatcct acggtggtgt tttctccaac aacggtccat ctcaagtcca attgagagac    180

gccgtcttga tgaacggtac tgtcgtttac gactctaacg gtgcttggga ctcctccgcc    240

ttggaagaat ggttgcaagg tcaaaagaag gtttccatcg aaaagatctt cgaaaacatt    300

ggtccatccg ccgtctaccc atctatttct ccaggtgtcg tcattgcctc tccatctcaa    360

actcacccag actacttcta ccaatggatc agagactctg ccttgaccat taactctatt    420

gtctctcact ctgctggtcc agccatcgaa actttgttgc aatacttgaa cgtttccttc    480

cacttgcaaa gatctaacaa cactttgggt gctggtattg gttacactaa cgacaccgtt    540

gctttgggtg acccaaagtg gaacgtcgac aacactgctt tcaccgaaga ctggggtcgt    600

ccacaaaacg acggtccagc tttgcgttcc attgccatct tgaagatcat cgactacatc    660

aagcaatctg gtactgactt gggtgccaag tacccattcc aatccaccgc tgacatcttc    720

gacgacattg ttcgttggga cttgcgtttc attattgacc actggaactc ttccggtttc    780

gacttgtggg aagaagtcaa cggtatgcac ttcttcactt tgttggtcca attgtctgct    840

gtcgacaagt ccttgtctta cttcaacgcc tccgaacgtt cctctccatt cgttgaagaa    900
```

```
ttgcgtcaaa cccgtagaga catctccaag ttcttggtcg acccagccaa cggtttcatc    960

aacggtaagt acaactacat tgttggtacc ccaatgattg ccgacacctt gagatccggt   1020

ttggacatct ccactttgtt ggctgccaac accgtccacg acgccccatc tgcttcccac   1080

ttgccattcg acatcaacga cccagccgtc ttgaacacct tgcaccactt gatgttgcac   1140

atgcgttcta tctacccaat caacgactcc tccaagaacg ctactggtat tgccttgggt   1200

cgttacccag aagacgtcta cgacggttac ggtttcggtg aaggtaaccc atgggtcttg   1260

gccacctgta ccgcttctac caccttgtac caattgattt acagacacat ctctgaacaa   1320

cacgacttgg ttgtcccaat gaacaacgac tgttctaacg ctttctggtc cgaattggtc   1380

ttctccaact tgactacttt gggtaacgac gaaggttact tgattttgga attcaacacc   1440

ccagccttca accaaaccat tcaaaagatc ttccaattgg ctgactcctt cttggtcaag   1500

ttgaaggctc acgtcggtac tgacggtgaa ttgtccgaac aattcaacaa gtacaccggt   1560

ttcatgcaag gtgcccaaca cttgacctgg tcctacactt ctttctggga cgcctaccaa   1620

atcagacaag aagttttgca atctttgtag                                    1650
```

<210> SEQ ID NO 11
<211> LENGTH: 2304
<212> TYPE: DNA
<213> ORGANISM: Saccharomyces cerevisiae

<400> SEQUENCE: 11

```
atgcagaggc cgtttctact cgcgtatctt gtactttcgc ttctatttaa ttcagcgcta     60

gggtttccga cagcactagt gcctcgagga tcgagtagta gcaatataac gtcaagcgga    120

ccttcatcaa cgccttttag cagcgcaaca gagagctttt caacgggcac gacagtaacg    180

ccgtcatcat cgaaatatcc tggcagtaaa acagagacaa gcgtaagtag tacaacggag    240

acgacaatag tacctacaac aacaacgacg tcagtgataa caccttcaac aacaacgata    300

acaacaacgg tatgctcaac aggaacaaat tcagcgggag agacgacaag cggatgcagc    360

cctaaaacaa taacaacgac agtgccttgc tcaacgagtc ctagcgagac ggcatcggag    420

tcaacaacaa cgtcacctac aacacctgta acaacagtgg tatcaacgac ggtggtaaca    480

acggagtatt cgacaagtac aaaacagggc ggcgagataa caacaacatt tgtgacgaaa    540

aatataccta cgacatatct aacaacaata gcacctacgt catcagtgac gacggtaacg    600

aattttacac cgacgacaat aacgacaacg gtatgcagca caggaacaaa tagcgcaggg    660

gagacgacgt caggatgcag tcctaaaaca gtgacaacaa cagtgccttg ctcaacgggg    720

acaggcgagt atacgacgga ggcaacagca cctgtaacaa cagcagtaac aacaacggtg    780

gtgacgacag agagtagtac gggaacgaat tcggcaggaa aaacgacaac gagttataca    840

acaaaaatcgg tacctacgac atatgtattt gattttggca aaggcatact cgatcagagc    900

tgcggcggcg tattttcaaa taatggcagt tcgcaggtgc agctgcggga tgtagtgctg    960

atgaatggga cagtggtata tgattcaaat ggcgcgtggg atagtagtcc gctggaggag   1020

tggctccagc gacagaaaaa agtaagtata gagcgaatat ttgagaatat agggcccagc   1080

gcagtgtatc cgtcgatact acctggggtg gtgatagcgt caccctcgca gacgcatccc   1140

gattattttt atcagtggat aagggatagc gcgctcacga taaatagtat agtatcacat   1200

agtgcggatc cggcaataga gacgttactt cagtatctga atgtatcatt tcatttacag   1260

aggacaaata atacactggg cgcgggcata gggtatacga atgatacagt ggcacttgga   1320
```

```
gatcctaaat ggaatgtgga taatacggca tttacggagc cttggggaag gcctcagaat   1380
gatggccctg cgcttcgaag catagcaata ttaaaaataa tagattatat aaaacagtca   1440
ggcacagatc tgggggcgaa atatccgttt cagagcacgg cagatatatt tgatgatata   1500
gtacgatggg atctgaggtt tataatagat cattggaata gctcgggatt tgatctatgg   1560
gaggaggtga atggcatgca ttttttttacg ttactggtac agctgtcagc agtggatagg   1620
tcgctgtcgt attttaatgc atcagagcgg tcgagtccct ttgtagagga gcttaggcag   1680
acacgccggg atatatcaaa atttttagtg gatcctgcga atgggtttat aaatggcaaa   1740
tataattata tagtagagac acccatgata gcagatacac tccgctcggg actggatata   1800
agcacgttat tagcggcgaa tacagtgcat gatgcgccga gtgcgtcaca tcttccgttt   1860
gatataaatg atcctgcggt gctgaatacg ctacatcatc tcatgctaca tatgcgatcg   1920
atatatccca taaatgatag cagtaaaaat gcaacgggaa tagcactggg ccggtatcct   1980
gaggatgtat atgatggata tggcgtaggc gagggaaatc cctgggtgct ggcgacgtgc   2040
gcagcatcaa caacgcttta tcagctcata tatcgccata taagtgagca gcatgatctc   2100
gtggtgccta tgaataatga ttgctcgaat gcattttgga gcgagctggt attttcaaat   2160
ctcacgacac tgggaaatga tgagggctat ctgatactgg agtttaatac acctgcattt   2220
aatcagacga tacagaaaat atttcagcta gcggattcat ttctggtaaa actgaaagcg   2280
acgtgggagc agacggggaa ttaa                                          2304
```

```
<210> SEQ ID NO 12
<211> LENGTH: 2304
<212> TYPE: DNA
<213> ORGANISM: Saccharomyces cerevisiae

<400> SEQUENCE: 12

atgcagaggc cgtttctact cgcatatttg gtactttcgc ttctatttaa ttcagcgttg     60
ggctttccga ctgcactagt acctagggga tcgtccagta gcaacataac ttcgagcggt    120
ccgtcatcaa cacctttttag cagcgcgacg gagagctttt caactggcac gactgtaact    180
ccttcatcaa gtaaatatcc tggcagtaaa acagaaacgt ctgtatcttc gacaacggag    240
actacgatag tgccgacaac aactacgaca agtgtaataa caccgtcaac aacgacaatt    300
acaacgacgg tgtgctctac aggaacaaat agcgcggggg agacaacttc tggatgctca    360
ccaaaaacga taacaacaac tgtaccctgc tcaaccagtc ccagcgagac ggcatcggaa    420
tcaacaacca cgtcacctac gacacctgta actacagtag tctcaacgac cgtagtgacg    480
acagagtatt caacgagtac aaaacagggg ggagagatta caacaacatt tgtaacgaaa    540
aatataccta caacatatct aactacaatt gcaccgacat catcagtaac tacggtgaca    600
aattttacgc cgacaacaat aactactacg gtgtgcagca caggaacaaa ttctgcaggc    660
gagacaacat caggatgctc gcccaagaca gtcacaacaa cggtgccttg ctcaacgggt    720
actggcgagt atacaacaga ggcgaccgcg cctgtaacaa cagctgtcac aaccacggtg    780
gtgacaacgg agagctctac ggggacaaat tcagcgggta aaacgacaac aagttataca    840
acaaaatcag taccgacgac gtatgtattt gattttggca aaggcatact cgatcaaagc    900
tgcggcggtg tattttcaaa caatggcagt tcgcaggtgc agctgcggga tgtagtctta    960
atgaatggga cagtggtata tgattcaaat ggcgcttggg atagtagtcc gctggaggag   1020
tggctccagc gacagaaaaa agtgagtata gagcgaatat ttgaaaatat agggcccagc   1080
gcagtgtatc cgagtatact tcctggggtc gtgatagcgt caccgtcgca gacgcatcca   1140
```

```
gattattttt accagtggat aagggatagc gcgctaacga taaatagtat tgtatcacat   1200

tcagcggatc cggcaataga gacgttacta cagtacctga atgtgtcatt tcatcttcag   1260

agaacgaata acacactcgg cgcaggcata gggtatacta atgatacagt ggcactagga   1320

gatcctaaat ggaatgtaga taacacggca tttacggaac cttggggaag gcctcagaat   1380

gatggccctg cgcttcgaag catagcgatc ttaaaaatca tagattatat aaaacagtca   1440

ggcacggatc tgggggcaaa atatcctttc cagtccacgg cagatatatt tgatgatata   1500

gtacggtggg atctgaggtt tataattgat cattggaata gttccggatt tgatctatgg   1560

gaggaggtaa atggcatgca ttttttttaca ttactggtac agctgtctgc agtggatagg   1620

tcgctgtcgt attttaatgc atcagaacgg tcgagcccct ttgtggagga actgcgacag   1680

acacgccggg atataagcaa atttttagtg gatcctgcga atgggtttat aaatggcaaa   1740

tataattata tagtggagac acccatgata gcagatacac ttaggagtgg actggatata   1800

tcgacgttat tagcggcgaa tacagtgcat gatgcgccgt ctgcgtcgca tcttccgttt   1860

gatatcaatg atcctgcagt actgaatacg cttcatcatc tcatgctaca tatgcgatcg   1920

atatacccca taaatgatag cagtaaaaat gcaacgggca tagcactggg ccggtatcct   1980

gaggatgtat atgatggata tggcgtaggc gagggaaatc cctgggtgct ggccacgtgt   2040

gcagcatcaa caacgcttta tcagctcata tatcggcata taagtgagca gcatgatctg   2100

gtagtaccta tgaataacga ttgctcgaat gcattttgga gcgagctggt atttagcaat   2160

ctcacgacac taggaaatga tgagggctat ttaattctag agttcaatac acctgcgttt   2220

aatcagacaa tacagaaaat atttcagcta gcggattcat tttagtaaa actgaaagca   2280

acgtgggagc agacggggaa ttaa                                           2304
```

<210> SEQ ID NO 13
<211> LENGTH: 2304
<212> TYPE: DNA
<213> ORGANISM: Saccharomyces cerevisiae

<400> SEQUENCE: 13

```
atgcagcgcc catttctact cgcttatctg gtgctttcgc ttctatttaa ttcagcgctt     60

ggctttccaa cagcactagt acctagggga tcgtcctcaa gcaacataac gtcgagtggt    120

ccaagttcaa ctccattcag ctctgcaaca gaaagcttta gtacgggcac gacagtcact    180

ccttcatcat ccaaatatcc tggcagtaaa acagaaactt ctgtatcatc tacaaccgaa    240

acaacaattg tgcccactac aacgacgact tctgtcataa caccatcaac aacgacgatt    300

acgacaacgg tatgctcaac aggaacaaac tctgccggcg agactacatc gggatgctct    360

cctaaaacaa taacaactac ggttccctgc tcaacaagtc caagcgaaac ggcatcggag    420

tcaacaacca cgtcacctac gacacctgta acgacagttg tatcaacgac agtggttact    480

actgagtata gtacgagtac aaaacaaggt ggagagatta caacaacatt tgtgaccaaa    540

aatattccga caacgtatct aacaacaata gcaccaactt catcagtcac tacggttacg    600

aattttaccc caacaactat tactacaacg gtgtgctcta caggaacaaa tagtgcaggg    660

gagacgacat ctggatgctc accaaagaca gtaacaacaa cagtgccttg ttcaactggg    720

actggcgagt atacaactga agcaacggca cctgtaacaa cagctgtaac aacaacagtt    780

gttaccacgg agtcaagtac gggtacaaat tccgctggta aaacgacaac tagttacaca    840

acaaaatctg taccaacaac atatgtattt gactttggca aaggcattct cgatcaaagc    900
```

```
tgcggcggag tattttcaaa taacggctcg tcgcaagtgc agctgcggga tgtagtattg    960

atgaatggga cagtggtata cgattcaaat ggcgcgtggg atagtagtcc gctggaggag   1020

tggctccagc gacagaaaaa agtaagcata gagcggatat ttgagaatat agggcccagc   1080

gcggtgtatc cgtcgatact acctggggta gtgatagcgt caccctcgca gacgcatcca   1140

gattatttct accaatggat aagggacagc gcgcttacga taaatagtat agtgagccat   1200

tctgcggatc cggcaataga gacgttattg cagtatctga atgtatcatt tcacctccaa   1260

cgcacgaata atacattggg cgcaggcata ggatacacta acgatacagt ggctttggga   1320

gatcctaagt ggaatgtcga taatacggct ttcacggaac cttggggtag gcctcaaaac   1380

gatggccctg cgcttcgaag catagccatc ttaaaaatca tagattatat caaacagagc   1440

ggcacagatc tgggggcaaa gtacccttt  cagagtacag cagatatatt tgatgatata   1500

gtacgttggg acctgaggtt tataattgac cattggaatt cgtccggatt tgatctatgg   1560

gaggaggtaa atggcatgca ttttttttact ttactggtac agctgtctgc agtggatagg   1620

tcgctgtcgt attttaatgc gtcagagcgg tcgtcaccct ttgtagagga gttgaggcag   1680

acacgccggg acatctcaaa atttttagtg gaccctgcga atgggtttat aaatggcaaa   1740

tacaattata ttgttgagac acccatgatt gccgacacat tgagatccgg actggacata   1800

agtacgttat tagctgcgaa tacggtccac gatgcgcctt cggcgagtca tcttccgttt   1860

gatataaatg atcctgcggt actgaatacg ttgcatcatc tgatgctcca tatgaggtcg   1920

atatacccca taaatgatag cagcaaaaat gcaacgggga tagcactggg ccggtatcct   1980

gaggatgtat atgatggata tggcgtgggc gagggaaatc cctgggtgct ggcgacgtgc   2040

gcagcgtcaa caacgcttta tcagctcata tatagacata tctcagagca gcatgattta   2100

gtagtgccta tgaataacga ttgttcgaac gcattttgga gcgagctggt attttccaat   2160

ctcacgactt tgggaaatga cgagggctat ctgatactag agtttaatac acctgcattt   2220

aatcagacaa tacagaaaat cttccagcta gctgattcat ttctcgtcaa actgaaagca   2280

acgtgggagc agacggggaa ttaa                                          2304
```

<210> SEQ ID NO 14
<211> LENGTH: 2304
<212> TYPE: DNA
<213> ORGANISM: Saccharomyces cerevisiae

<400> SEQUENCE: 14

```
atgcagcggc catttctact cgcatatttg gtcctttcgc ttctatttaa ttcagcgttg     60

ggctttccca cggcactagt tcctcgcgga tcctcaagca gcaacataac gagctcaggc    120

ccatcgtcaa ctcccttcag ctcggcaacg gagagctttt ctacaggcac tacagtcaca    180

ccatcatcat cgaaataccc tggcagtaaa acagaaactt ctgtaagcag cacaaccgag    240

actacgattg ttcccacgac aacgacgacg agcgtcataa caccatcaac aacaactatt    300

acaactacgg tgtgctctac aggaacaaac tctgcagggg aaacaacttc tggatgcagc    360

ccaaagacca taacaacgac tgttccatgt tcaacgagtc ctagcgaaac cgcatcggaa    420

tcaacaacca cgtcacctac aacacctgta actacagtgg tctcaacaac cgtagtgact    480

actgagtatt ctactagtac aaaacaaggg ggtgaaataa caacaacatt tgtcaccaaa    540

aacataccaa ccacttacct aacgacaata gctccaactt catcagtgac tacggttacc    600

aatttcacac ccaccactat tactacaacg gtttgcagca caggaacaaa ttctgcgggt    660

gagacaacct ctggatgctc tccaaaaaca gtaacaacaa ctgttccttg ctcaacgggt    720
```

```
acgggcgaat atactactga agctacagcc cctgttacaa cagcggtcac aaccaccgtt    780

gttacaacag aatcctcaac gggtactaat agcgctggta agacgacaac tagttataca    840

acaaaatctg tacctaccac gtatgtattt gattttggca aaggcattct cgatcaaagc    900

tgcggcggag tattttcaaa caatggcagc tcgcaagtgc agctgcggga tgtagtcctc    960

atgaatggga cagtggtata tgattcaaat ggcgcgtggg atagtagtcc gctggaggag   1020

tggctccagc gacagaaaaa agtttccata gaaaggatat ttgagaatat agggcccagc   1080

gcggtgtatc cgtctatatt acctggggtg gtgattgcgt caccatcgca aacgcatcca   1140

gactacttct accagtggat aagggacagc gcgctcacga taaacagtat tgtcagccat   1200

tctgcggatc cggcaataga gacgttactt cagtacctga acgtttcatt tcacttgcaa   1260

agaaccaaca atacattggg cgctggcatt ggttacacta acgatacagt ggcgttggga   1320

gatcctaagt ggaacgtcga caatacggct tttacggagc cttggggccg tcctcagaat   1380

gatggccctg ctcttcgaag catagccatc ttaaaaatca tcgactacat caaacaaagc   1440

ggcacggatc tgggggccaa atatccattt cagtccaccg cagatatatt tgatgatatt   1500

gtacgttggg atctgaggtt tattattgac cattggaatt catcaggatt tgatctatgg   1560

gaggaggtaa atggcatgca ttttttttaca ttactggtac aactgtcggc agtggatagg   1620

tcgctgtcgt attttaatgc ctcagagcgg tcgtctccct ttgtggagga attacgtcag   1680

acacgccggg atatctcaaa atttttagtg gatcctgcga atgggtttat caatggcaag   1740

tacaattata ttgttgagac acccatgatt gcggacacat tacggagcgg actggacata   1800

tccacattat tagcagcgaa tacggtacac gatgcgccat ctgctagcca tcttccgttc   1860

gatataaatg accctgccgt actgaacacg ttacaccatt taatgttgca tatgcgctcg   1920

atatatccca taaacgatag cagcaaaaat gcaacgggta ttgccctggg ccggtatcct   1980

gaggacgtat atgatggata tggcgttggc gagggaaatc cctgggtcct ggccacgtgt   2040

gccgcttcaa caacgcttta tcagctcatt tacagacata tatctgagca gcatgacctc   2100

gtagtgccaa tgaataacga ttgctcgaac gcattttgga gcgagctggt attctcaaac   2160

ctcacgactt tgggaaatga cgagggctat ttgattttgg agttcaatac acctgccttc   2220

aatcagacca tacaaaaaat attccaacta gctgattcat tttggtaaa gctgaaagcg    2280

acgtgggagc agacggggaa ctaa                                          2304


<210> SEQ ID NO 15
<211> LENGTH: 2304
<212> TYPE: DNA
<213> ORGANISM: Saccharomyces cerevisiae

<400> SEQUENCE: 15

atgcaaagac catttctact cgcttatttg gtcctttcgc ttctatttaa ctcagctttg     60

ggttttccaa ctgcactagt tcctagagga tcgtcctcta gcaatatcac gtcctccggg    120

ccatcttcaa ctccgttcag ctctgctaca gaaagctttt ctactggcac tactgtcact    180

ccatcatcat ccaaataccc tggcagtaaa acagagactt ctgtttcttc tacaaccgaa    240

actacaattg ttccaactac aactacgact tcagtgataa caccctcaac aaccactata    300

accactacgg tttgcagcac aggaacaaac tctgcaggtg aaactacttc tggatgctct    360

cccaagacca taacaactac tgtaccatgc tcaaccagtc caagcgagac ggcatcggag    420

tcaacaacca cgtcacctac cacacctgta actacagttg tctcaacaac cgtcgttaca    480
```

```
actgagtata gcactagtac aaaacaaggt ggtgaaatta caactacatt tgtcaccaaa    540

aacataccta cgacgtacct aactacaatt gcgccaactt catcagtcac tacggttacc    600

aatttcaccc caaccactat tactacaacg gtttgctcta caggaacaaa cagcgcgggt    660

gagactacct ctggatgctc tccaaagact gtcacaacaa ctgttccttg ttcaactggt    720

actggcgaat atactactga agctaccgca cctgttacaa cagctgtcac aacaacagtt    780

gttaccactg aatcctctac gggtacaaac tccgcaggta agacgacaac tagttataca    840

acaaagtctg taccaaccac gtatgtattt gattttggca aaggcattct cgatcagagc    900

tgcggcggtg tattttcaaa taatggctct tcgcaagtgc agctgcggga tgtagtcttg    960

atgaatggga cagtggtata cgattcaaac ggcgcatggg acagtagtcc gctggaggag   1020

tggctccagc gacagaaaaa agttagtatc gagagaatat ttgaaaatat tgggcccagc   1080

gccgtgtatc cgtctatttt gcctggggta gtgattgcgt caccatcgca aacgcatcca   1140

gactacttct accagtggat aagggacagc gcgttgacga taaacagtat agtctctcat   1200

tctgcggacc cggcaataga gacgttattg cagtacctga acgtttcatt ccacttacaa   1260

agaaccaata acacattggg cgcgggcatt ggttacacta acgatacagt ggctttggga   1320

gatcctaagt ggaacgtcga caatacggct tttacggaac cttggggtcg tcctcaaaac   1380

gatggccctg cacttcgaag cattgcgatc ttaaaaatca tcgactatat caagcagtct   1440

ggcacagatc tgggggccaa atacccattc cagtccaccg cagatatctt tgatgatata   1500

gtacgttggg acctgaggtt cattattgac cactggaatt catcaggatt tgatctatgg   1560

gaggaagtca atggcatgca tttctttact ttactggtac aactgtctgc agtggatagg   1620

tcgctgtcgt attttaatgc atcagaacgg tcgtctccct ttgttgaaga actacggcag   1680

acacgccggg atatctccaa gtttttagtg gaccctgcga atgggtttat caacggcaaa   1740

tacaattata ttgtagagac acccatgatt gccgacacat tgagatccgg actggacata   1800

tccactttat tagcggcgaa cacagtccac gatgcgccaa gcgcatcgca tcttccgttc   1860

gatatcaatg accctgccgt gctgaacacg ttacatcatt tgatgttgca catgcgttcg   1920

atatacccca tcaacgatag ctccaaaaat gcaacgggga tagccctggg ccggtatcct   1980

gaggacgtat atgatggata tggcgtgggc gagggaaatc cctgggtgct ggcgacgtgt   2040

gccgcgtcaa caacgcttta tcagctcata tatagacata tctctgagca gcatgacttg   2100

gttgtcccta tgaacaacga ttgttcgaac gcattttgga gcgagctggt attctccaac   2160

ctcacgactt tgggaaatga cgagggctat ttgatacttg agttcaatac acctgcattt   2220

aatcagacca tacagaaaat ctttcaacta gcagattcat tcctagtcaa actgaaagcc   2280

acgtgggaac agacggggaa ctaa                                          2304
```

<210> SEQ ID NO 16
<211> LENGTH: 2304
<212> TYPE: DNA
<213> ORGANISM: Saccharomyces cerevisiae

<400> SEQUENCE: 16

```
atgcaacgcc catttctact cgcttatttg gtcctttcgc ttctatttaa ctcagctttg     60

ggatttccaa ctgcactagt tcctagagga tcctcgtcta gcaacatcac ttcctccggt    120

ccatcttcaa ctccattcag ctctgctact gaaagctttt ctactggcac aactgtcact    180

ccatcatcat ccaaataccc tggcagtaaa acagaaacat ctgtttcttc tacaaccgag    240

actaccattg ttccaacaac aactacgact tctgtcataa caccatcaac aaccactatt    300
```

```
accacgacgg tttgctctac aggaacaaac tctgccggtg aaactacttc tggatgctct    360
ccaaagacca ttacaactac tgttccatgt tcaaccagtc caagcgaaac cgcatcggaa    420
tcaacaacca cttcacctac cacacctgta acaacagttg tctcaaccac cgtcgttact    480
acagagtatt ctactagtac aaaacaaggt ggtgaaatta caacaacatt tgtcaccaaa    540
aacattccaa ccacttacct aactacaatt gctccaactt catcagtcac tacggttacc    600
aatttcaccc caaccactat tactactacg gtttgcagta caggaacaaa ctcggccggt    660
gaaactacat ctggatgctc tccaaagact gtcacaacaa ctgttccttg ttcaactggt    720
actggcgaat acactactga agctaccgcc cctgttacaa cagctgtcac aacgaccgtt    780
gttaccactg aatcctctac gggtactaac tccgctggta agacgacaac tagttacaca    840
acaaagtctg taccaaccac ctatgtattt gactttggca agggcattct cgatcaaagc    900
tgcggcggtg tattttcaaa caacggctct tcgcaagtgc agctgcggga tgtagtactg    960
atgaatggga cagtggtata cgattcaaac ggcgcttggg acagtagtcc gctggaggag   1020
tggctccagc gacagaaaaa agtttccatc gaaagaatat ttgaaaatat tgggcccagc   1080
gccgtgtatc cgtctatttt gcctggggtc gtgattgcgt caccatcgca aacgcatcca   1140
gactacttct atcaatggat aagggacagc gcgttgacga taaacagtat tgtctctcat   1200
tctgcggacc cggcaataga gacgttattg cagtacctga acgtttcatt ccacttgcaa   1260
agaaccaaca acacattggg cgctggcatt ggttacacta acgatacagt ggctttggga   1320
gaccctaagt ggaacgtcga caacacggct ttcacggaac cttggggtcg tcctcaaaac   1380
gatggccctg ctcttcgaag cattgccatc ttaaaaatca tagactacat caagcaatct   1440
ggcactgatc tgggggccaa gtacccattc cagtccaccg cagatatatt tgatgatatt   1500
gtacgttggg acctgaggtt cattattgac cactggaatt cttccggatt tgatctatgg   1560
gaggaagtca atggcatgca tttctttact ttactggtac aactgtctgc agtggatagg   1620
tcgctgtcgt attttaacgc ctcagaacgg tcgtctccct ttgttgaaga attgcgtcag   1680
acacgccggg acatctccaa gtttttagtg gaccctgcga atgggtttat caacggcaag   1740
tataattata ttgttgagac acccatgatt gccgacacat tgagatccgg actggacata   1800
tccacgttat tagctgcgaa caccgtccac gatgcgccat ctgcttccca tcttccgttc   1860
gatatcaatg accctgccgt cctgaacacg ttgcaccatt tgatgttgca catgcgttcg   1920
atatacccca tcaacgatag ctccaaaaat gcaacgggaa ttgcactggg ccggtatcct   1980
gaggacgtat atgatggata tggcgttggc gagggaaatc cctgggtcct ggccacgtgt   2040
gccgcttcaa caacgcttta tcagctcatt tacagacaca tctctgagca gcatgacttg   2100
gttgtaccaa tgaacaacga ttgttcgaac gcattttgga gcgagctggt attctccaac   2160
ctcacgactt tgggaaatga tgagggctat ttgattttgg agttcaatac acctgccttc   2220
aatcaaacca tacaaaaaat cttccaacta gcggattcat tcttggtcaa gctgaaagcc   2280
acgtgggaac agacggggaa ctaa                                          2304
```

<210> SEQ ID NO 17
<211> LENGTH: 2304
<212> TYPE: DNA
<213> ORGANISM: Saccharomyces cerevisiae

<400> SEQUENCE: 17

```
atgcaaagac cattcctact cgcttatttg gtcctttcgc ttctatttaa ctctgctttg     60
```

```
ggttttccaa ctgcactagt tcctagagga tcctcctcta gcaacatcac ttcctccggt    120
ccatcttcaa ctccattcag ctctgctact gaaagctttt ctactggcac tactgtcact    180
ccatcatcat ccaagtaccc aggctccaaa acagaaactt ctgtttcttc tacaaccgaa    240
actaccattg ttccaactac aactacgact tctgtcataa caccatcaac aaccactatt    300
accactacgg tttgctctac aggaacaaac tctgccggtg aaactacttc tggatgctct    360
ccaaagacca ttacaactac tgttccatgt tccacctccc catctgaaac cgcatcggaa    420
tctacaacca cttcacctac cacacctgta actacagttg tctcaaccac cgtcgttact    480
actgagtatt ctactagtac aaaacaaggt ggtgaaatta caactacatt tgtcaccaaa    540
aacattccaa ccacttacct aactacaatt gctccaactt catcagtcac tacggttacc    600
aatttcaccc caaccactat tactactacc gtttgctcta caggaacaaa ctctgccggt    660
gaaactacct ctggatgctc tccaaagact gtcacaacaa ctgttccttg ttcaactggt    720
actggcgaat acactactga agctaccgcc cctgttacta cagctgtcac caccaccgtt    780
gttaccactg aatcctctac gggtactaac tccgctggta agacgacaac tagttacaca    840
acaaagtctg taccaaccac ctatgtattc gactttggca agggcattct cgatcaaagc    900
tgcggcggtg tattttcaaa caacggctct tcgcaagttc agctgcggga tgtagtcttg    960
atgaacggga cagtggtata cgattcaaac ggcgcttggg acagttcccc gctggaagag   1020
tggttgcagc gacagaaaaa agtttccatc gaaagaattt ttgaaaatat tgggccctcc   1080
gccgtgtatc cgtctatttt gcctggggtc gtgattgcgt caccatcgca aactcatcca   1140
gactacttct accaatggat aagggacagc gcgttgacga tcaactctat tgtctctcat   1200
tctgcggacc cggcaataga gacgttgttg cagtacctga acgtttcatt ccacttgcaa   1260
agaaccaaca acaccttggg cgctggcatt ggttacacta acgatacagt ggctttggga   1320
gaccctaagt ggaacgtcga caacacggct ttcacggaac cttggggtcg tcctcaaaac   1380
gatggccctg ctcttcgaag cattgccatc ttgaaaatca tcgactacat caagcaatct   1440
ggcactgatc tgggggccaa gtacccattc cagtccaccg cagatatctt tgacgatatt   1500
gtccgttggg acctgaggtt cattattgac cactggaatt cttccggatt tgacctatgg   1560
gaggaagtca atggcatgca tttctttact ttactggtac aactgtctgc agttgacagg   1620
tcgctgtctt attttaacgc ctcagaacgt tcgtctccat ttgttgaaga attgcgtcag   1680
acacgccggg acatctccaa gtttttagtg gaccctgcga acggttttat caacggcaag   1740
tacaattata ttgttgaaac acccatgatt gccgacacat tgagatccgg actggacata   1800
tccactttat tagctgcgaa caccgtccac gacgcgccat ctgcttccca tcttccgttc   1860
gatatcaatg accctgccgt cctgaacact ttgcaccatt tgatgttgca catgcgttcg   1920
atatacccca tcaacgatag ctccaaaaat gcaactggta ttgccctggg ccggtatcct   1980
gaggacgtat atgatggata tggcgttggc gagggaaatc cctgggtcct ggccacgtgt   2040
gccgcttcaa caacgcttta ccagctcatt tacagacaca tctctgagca gcatgacttg   2100
gttgtcccaa tgaacaacga ttgttcgaac gcattttgga gcgaattggt attctccaac   2160
ctcacgactt tgggaaacga cgaaggctat ttgattttgg agttcaatac tcctgccttc   2220
aatcaaacca tacaaaaaat cttccaacta gctgactcat tcttggtcaa gctgaaagcc   2280
acgtgggaac agacggggaa ctaa                                          2304
```

<210> SEQ ID NO 18
<211> LENGTH: 2304

<212> TYPE: DNA
<213> ORGANISM: Saccharomyces cerevisiae

<400> SEQUENCE: 18

```
atgcaaagac catttttgtt ggcttatttg gtcctttcgt tgctattcaa ctcagctttg     60
ggtttcccaa ctgcactagt tccaagagga tcctcctcta gcaacatcac ttcctccggt    120
ccatcttcca ctccattctc ctctgctact gaaagctttt ctactggcac tactgtcact    180
ccatcttctt ccaagtaccc tggcagtaaa acagaaactt ctgtttcttc tacaaccgaa    240
actaccattg ttccaactac aactacgact tctgtcataa caccatctac aaccactatt    300
accactacgg tttgctctac aggtactaac tctgccggtg aaactacttc tggatgttct    360
ccaaagacca ttactactac tgttccatgt tcaaccagtc caagcgaaac cgcatccgaa    420
tctacaacca cttcacctac cactcctgta actaccgttg tctcaaccac cgtcgttact    480
actgagtact ctactagtac aaaacaaggt ggtgaaatta caactacttt cgtcaccaag    540
aacattccaa ccacttacct aactactatt gctccaactt catcagtcac tactgttacc    600
aacttcaccc caaccactat tactactacg gtttgctcta ctggaacaaa ctctgccggt    660
gaaactacct ctggatgctc tccaaagact gtcaccacaa ctgttccttg ttcaactggt    720
actggcgaat acactactga agctaccgcc ccagttacaa cagctgtcac caccaccgtt    780
gttaccactg aatcctctac gggtactaac tccgctggta agactacaac ttcttacaca    840
actaagtctg taccaaccac ctatgttttt gactttggta agggcattct cgatcaaagc    900
tgcggcggtg tcttctcaaa caacggctct tcgcaagtgc agctgagaga tgtagtcttg    960
atgaatggga cagtcgtata cgactccaac ggcgcttggg actcttctcc actggaagag   1020
tggttgcaga gacaaaaaaa ggtttccatc gaaagaattt ttgaaaatat tgggcccagc   1080
gccgtgtatc catctatttt gccaggggtc gtgattgcgt caccatctca aacgcatcca   1140
gactacttct accaatggat cagagacagc gctttgacga taaactctat tgtctctcac   1200
tctgcggacc cagcaatcga aacgttgttg caatacctga acgtttcatt ccacttgcaa   1260
agaaccaaca acactttggg cgctggcatt ggttacacta acgatacagt ggctttgggt   1320
gaccctaagt ggaacgtcga caacacggct ttcacggaac cttggggtcg tcctcaaaac   1380
gatggtccag ctttgcgatc tattgccatc ttaaaaatca tcgactacat caagcaatct   1440
ggcactgacc tgggtgccaa gtacccattc cagtccaccg ccgatatctt tgatgacatt   1500
gtacgttggg acttgaggtt cattattgac cactggaact cttccggatt tgatttgtgg   1560
gaagaagtca atggcatgca cttctttact ttgctggttc aattgtctgc cgtggacagg   1620
tcgctgtcct acttcaacgc ctcagaacgg tcttctccct tcgttgaaga attgcgtcag   1680
acacgtcggg acatctccaa gttcttagtg gaccctgcta atgggtttat caacggcaag   1740
tacaattaca ttgttgaaac accaatgatt gccgacacat tgagatccgg actggacata   1800
tccactttgt tagctgcgaa caccgtccac gatgcgccat ctgcttccca tcttccattc   1860
gatatcaacg accctgccgt cttgaacacg ttgcaccatt tgatgttgca catgcgttcg   1920
atatacccca tcaacgacag ctccaaaaac gcaaccggta ttgccctggg tcggtaccct   1980
gaagacgtat atgatggata tggcgttggc gaaggtaatc cctgggtctt ggccacgtgt   2040
gccgcttcta ccacgttgta tcagttgatt tacagacaca tctctgagca gcacgacttg   2100
gttgtcccaa tgaacaacga ttgttcgaac gccttttggt ctgagctggt attctccaac   2160
ctcacgactt tgggaaatga cgaaggttat ttgattttgg agttcaatac tcctgccttc   2220
```

```
aatcaaacca tacaaaaaat cttccaacta gctgattctt tcttggtcaa gctgaaggcc   2280

acttgggaac agacggggaa ctaa                                          2304


<210> SEQ ID NO 19
<211> LENGTH: 2304
<212> TYPE: DNA
<213> ORGANISM: Saccharomyces cerevisiae

<400> SEQUENCE: 19

atgcaaagac cattcttgtt ggcttacttg gtcctttcgt tgttgttcaa ctcagctttg     60

ggtttcccaa ctgctttggt tcctagaggt tcctcctcta gcaacatcac ttcctccggt    120

ccatcttcta ctccattcag ctctgctact gaaagcttct ctactggtac tactgtcact    180

ccatcatcat ccaagtaccc aggctctaag acagaaactt ctgtttcttc tacaaccgaa    240

actaccattg ttccaactac tactactact tctgtcatca caccatccac taccactatt    300

accactactg tttgctctac tggtactaac tctgccggtg aaactacttc tggatgctct    360

ccaaagacca ttaccactac tgttccatgt tccaccagtc caagcgaaac cgcctccgaa    420

tctaccacca cttcccctac cactccagtc actacagttg tctcaaccac cgtcgttact    480

actgaatatt ctacttccac aaaacaaggt ggtgaaatta caactacctt tgtcaccaag    540

aacattccaa ccacttacct aactaccatt gctccaactt cctcagtcac taccgttacc    600

aacttcaccc caaccactat tactactacg gtttgctcta caggtaccaa ctctgccggt    660

gaaactacct ctggttgttc tccaaagact gtcaccacaa ctgttccatg ttcaactggt    720

actggcgaat acactactga agctaccgcc cctgttacca ctgctgtcac caccaccgtt    780

gttaccactg aatcctctac tggtactaac tccgctggta agaccaccac tagttacacc    840

accaagtctg taccaaccac ctacgttttt gacttcggta agggcatttt ggatcaatct    900

tgcggcggtg tattctccaa caacggctct tctcaagtcc aactgcggga cgtcgtcttg    960

atgaacggga ctgtggtata cgattctaac ggtgcttggg actcctcccc gctggaggag   1020

tggttgcaga gacagaagaa ggtttccatc gaaagaatat tcgaaaacat tgggccatcc   1080

gccgtctacc catctatttt gcctggggtc gttattgcgt ctccatcgca aacccaccca   1140

gactacttct accaatggat acgtgactcc gctttgacta taaactccat tgtctctcat   1200

tctgcggacc cggcaattga gaccttgttg cagtacttga acgtttcttt ccacttgcaa   1260

agaaccaaca acacattggg tgctggtatt ggttacacta acgatacagt ggctttggga   1320

gacccaaagt ggaacgtcga caacacggct ttcactgaac catggggtcg tccacaaaac   1380

gatggtccag ctcttagaag cattgccatc ttgaaaatca tcgactacat caagcaatct   1440

ggtactgact tgggggccaa gtacccattc caatccaccg ccgacatctt tgatgacatt   1500

gtccgttggg acttgagatt cattattgac cactggaact cttccggttt tgacctatgg   1560

gaagaagtca acggtatgca cttcttcact ttattggtac aactgtctgc tgtggacagg   1620

tctttgtcgt attttaacgc ctccgaacgt tcgtctccct tcgttgaaga attgcgtcaa   1680

acacgccggg acatctccaa gtttttggtc gaccctgcga acgggtttat caacggtaag   1740

tacaattaca ttgttgaaac accaatgatt gccgacacat tgagatccgg actggacata   1800

tccactttgt tagctgcgaa caccgtccac gacgctccat ctgcttccca ccttccattc   1860

gatatcaacg acccagccgt cctgaacacg ttgcaccact tgatgttgca catgcgttct   1920

atttacccaa tcaacgacag ctccaagaac gctaccggta ttgccttggg tcggtaccct   1980

gaggacgtct acgatggtta tggcgttggc gagggtaacc cctgggtctt ggccacgtgt   2040
```

```
gccgcttcta caactcttta tcaattgatt tacagacaca tctctgagca gcacgacttg   2100

gttgtcccaa tgaacaacga ctgttccaac gctttctgga gcgagctggt cttctccaac   2160

ttgactactt tgggtaatga cgaaggctat ttgattttgg aattcaacac acctgccttc   2220

aaccaaacca tccaaaagat cttccaattg gctgattctt tcttggtcaa gctgaaagcc   2280

acgtgggaac agaccggtaa ctaa                                           2304
```

<210> SEQ ID NO 20
<211> LENGTH: 2304
<212> TYPE: DNA
<213> ORGANISM: Saccharomyces cerevisiae

<400> SEQUENCE: 20

```
atgcaaagac cattcttgtt ggcttacttg gtcttgtcgt tgttgtttaa ctccgctttg     60

ggttttccaa ctgccttggt tccaagaggt tcctcctctt ccaacatcac ttcctccggt    120

ccatcttcta ctccattctc ctctgctact gaaagcttct ctactggtac tactgtcact    180

ccatcatctt ccaagtaccc aggttctaag actgaaactt ctgtttcttc tactaccgaa    240

actaccattg ttccaactac tactaccact tctgtcatta ctccatctac aaccactatt    300

accactactg tttgctctac cggaacaaac tctgccggtg aaactacttc tggttgttct    360

ccaaagacca ttaccactac tgttccatgt tcaaccagtc caagcgaaac cgcctctgaa    420

tcaaccacca cttccccaac cacaccagtt actacagttg tctctaccac cgtcgttact    480

actgaatact ctactagtac taagcaaggt ggtgaaatta ccactacctt cgtcaccaag    540

aacattccaa ccacttactt gactacaatt gctccaactt cttcagtcac taccgttacc    600

aacttcaccc caaccactat tactactacc gtttgttcta ccggtacaaa ctctgccggt    660

gaaactacct ctggttgttc tccaaagact gtcaccacca ctgttccatg ttctactggt    720

actggtgaat acactactga agctaccgcc cctgttacca ctgctgtcac taccaccgtt    780

gttaccactg aatcctctac cggtactaac tccgctggta agaccaccac ttcctacacc    840

acaaagtctg taccaaccac ctacgttttt gacttcggta agggtatttt ggaccaatcc    900

tgtggtggtg tattctctaa caacggttct tcgcaagtcc agttgagaga cgtcgtcttg    960

atgaacggta ctgttgttta cgactccaac ggcgcttggg actcctcccc attggaagaa   1020

tggctccaac gacaaaagaa agtttccatc gaaagaatct tcgaaaacat tggtccatcc   1080

gccgtttatc catctatttt gccaggggtc gtcattgcct ccccatctca aactcatcca   1140

gactacttct accaatggat tagggacagc gccttgacca ttaactctat tgtctctcac   1200

tctgctgacc cagctattga gaccttgttg caatacttga acgtttcttt ccacttgcaa   1260

agaaccaaca acactttggg tgctggtatt ggttacacta acgatactgt cgctttgggt   1320

gacccaaagt ggaacgtcga caacaccgct ttcaccgaac catggggtcg tccacaaaac   1380

gatggtccag ctttgcgttc tattgccatc ttgaaaatca tcgactacat caagcaatct   1440

ggtactgact tgggtgccaa gtacccattc cagtccaccg ctgacatctt cgatgacatt   1500

gtccgttggg acttgcgttt cattattgac cactggaact cttccggttt cgacttgtgg   1560

gaagaagtca acggcatgca tttctttact ttgttggtcc aattgtctgc cgtggacaga   1620

tctttgtctt actttaacgc ctccgaacgt tcctctccat tcgttgaaga attgcgtcag   1680

acacgtcggg acatctccaa gttcttggtg gaccctgcta acggttttat caacggtaag   1740

tacaattaca ttgttgagac tccaatgatt gccgacacct tgagatccgg attggacatc   1800
```

```
tccactttgt tggctgcgaa caccgtccac gatgcgccat ctgcttccca tttgccattc   1860
gacatcaatg acccagccgt cttgaacact ttgcaccact tgatgttgca catgcgttct   1920
atctacccaa tcaacgacag ctccaaaaac gctactggta ttgccttggg ccgttaccca   1980
gaagacgtct acgatggtta cggtgttggt gaaggaaacc cctgggtctt ggccacttgt   2040
gccgcttcca ctactcttta tcagctcatt tacagacaca tctctgaaca acacgacttg   2100
gttgtcccaa tgaacaacga ctgttctaac gccttctggt ccgaattggt cttctccaac   2160
ttgaccactt tgggtaatga cgaaggttac ttgattttgg aattcaacac accagccttc   2220
aaccaaacca tccaaaagat cttccaattg gctgattcct tcttggtcaa gttgaaggcc   2280
acttgggaac agacgggtaa ctaa                                          2304
```

```
<210> SEQ ID NO 21
<211> LENGTH: 2304
<212> TYPE: DNA
<213> ORGANISM: Saccharomyces cerevisiae

<400> SEQUENCE: 21

atgcaaagac cattcttgtt ggcttacttg gtcttgtcct tgttgttcaa ctccgctttg     60
ggtttcccaa ctgctttggt tccaagaggt tcctcctctt ccaacatcac ttcctccggt    120
ccatcttcca ctccattctc ttctgctact gaatccttct ctactggtac tactgtcact    180
ccatcctcct ccaagtaccc aggttccaag accgaaactt ctgtttcttc tactaccgaa    240
actaccattg ttccaactac cactactact tctgtcatca ccccatctac caccactatt    300
accactaccg tttgttctac cggtaccaac tctgccggtg aaactacttc tggttgttct    360
ccaaagacca ttactactac tgttccatgt tctacctccc catccgaaac cgcttctgaa    420
tccaccacca cttccccaac caccccagtt actaccgttg tctccaccac cgtcgttact    480
actgaatact ctacttctac taagcaaggt ggtgaaatta ccactacttt cgtcaccaag    540
aacattccaa ccacttactt gactaccatt gctccaactt cctccgtcac tactgttacc    600
aacttcaccc caaccactat tactactacc gtttgttcta ctggtaccaa ctctgccggt    660
gaaactacct ctggttgttc tccaaagact gtcaccacca ctgttccatg ttccactggt    720
actggtgaat acactactga agctaccgcc ccagttacta ccgctgtcac caccaccgtt    780
gttaccactg aatcctctac tggtactaac tccgctggta agaccaccac ttcttacacc    840
accaagtctg tcccaaccac ctacgttttc gacttcggta agggtatttt ggaccaatct    900
tgtggtggtg ttttctccaa caacggttct tcccaagtcc aattgagaga cgtcgtcttg    960
atgaacggta ctgttgttta cgactccaac ggtgcttggg actcctcccc attggaagaa   1020
tggttgcaaa gacaaaagaa ggtttccatc gaaagaatct tcgaaaacat tggtccatcc   1080
gccgtttacc catctatttt gccaggtgtc gtcattgctt ctccatccca aacccaccca   1140
gactacttct accaatggat cagagactcc gctttgacta tcaactctat tgtctctcac   1200
tctgccgacc cagccattga aaccttgttg caatacttga acgtttcttt ccacttgcaa   1260
agaaccaaca acaccttggg tgctggtatt ggttacacta acgacactgt cgctttgggt   1320
gacccaaagt ggaacgtcga caacaccgct ttcactgaac catggggtcg tccacaaaac   1380
gacggtccag ctttgcgttc tattgccatc ttgaagatca tcgactacat caagcaatct   1440
ggtactgact tgggtgccaa gtacccattc caatccaccg ccgacatctt cgacgacatt   1500
gttcgttggg acttgcgttt cattattgac cactggaact cttccggttt cgacttgtgg   1560
gaagaagtca acggtatgca cttcttcact ttgttggttc aattgtctgc tgttgaccgt   1620
```

```
tctttgtctt acttcaacgc ctccgaacgt tcctctccat tcgttgaaga attgcgtcaa   1680
actcgtagag acatctccaa gttcttggtc gacccagcta acggtttcat caacggtaag   1740
tacaactaca ttgttgaaac tccaatgatt gccgacacct tgagatccgg tttggacatt   1800
tccactttgt tggctgctaa caccgtccac gacgctccat ctgcttccca cttgccattc   1860
gacatcaacg acccagccgt cttgaacacc ttgcaccact tgatgttgca catgcgttcc   1920
atctacccaa tcaacgactc ttccaagaac gccactggta ttgccttggg tagataccca   1980
gaagacgttt acgacggtta cggtgttggt gaaggtaacc catgggtctt ggccacttgt   2040
gccgcttcca ctaccttgta ccaattgatt tacagacaca tctctgaaca acacgacttg   2100
gttgtcccaa tgaacaacga ctgttccaac gccttctggt ctgaattggt tttctccaac   2160
ttgactactt tgggtaacga cgaaggttac ttgattttgg aattcaacac tccagccttc   2220
aaccaaacca tccaaaagat cttccaattg gctgactctt tcttggtcaa gttgaaggcc   2280
acttgggaac aaactggtaa ctaa                                          2304
```

```
<210> SEQ ID NO 22
<211> LENGTH: 2337
<212> TYPE: DNA
<213> ORGANISM: Saccharomyces cerevisiae

<400> SEQUENCE: 22

atggtaggcc tcaaaaatcc gtatacgcat acgatgcaga ggccctttct actcgcatat     60
ctagtgcttt cgcttctatt taattcagcg ctcggctttc cgacggcact agtgcctcgg    120
ggatcgagta gtagcaatat aacgtcatca ggacccagtt caacgccctt tagcagcgcg    180
acggagagct ttagcacggg cacgacggtg acgccgtcat catcaaaata tcctggcagt    240
aaaacagaga catcagtaag cagtacaacg gagacaacga tagtgcctac gacaacaacg    300
acatcagtga taacaccttc aacaacgacg ataacgacga cggtgtgcag cacaggaaca    360
aatagtgcgg gagagacaac atcgggatgc agccctaaaa cgataacaac aacagtgccg    420
tgctcaacga gtcccagcga gacagcatcg gagtcaacaa cgacgtcacc tacaacacct    480
gtaacgacag tggtatcaac gacagtggta acaacggagt attcaacaag tacaaaacag    540
ggcggcgaga taacaacaac atttgtaaca aaaaatatac cgacaacgta tctaacaaca    600
atagcgccga catcatcagt gacaacggtg acaaatttta cgccgacaac gataacaacg    660
acggtatgct caacaggaac aaattcagca ggcgagacaa caagcggatg ctcgcctaaa    720
acggtaacaa caacggtacc ttgctcaacg ggcacgggcg agtatacaac ggaggcaacg    780
gcgcctgtga caacagcagt gacaacaaca gtggtaacaa cagagtcaag cacgggaacg    840
aattcagcag gaaaaacgac aacaagttat acaacaaaat cggtacctac aacgtatgta    900
tttgattttg gcaaaggcat actcgatcag agctgcggcg gggtattttc aaataatggc    960
tcgtcgcagg tgcagctgcg ggatgtagta ctcatgaatg ggacagtggt atatgattca   1020
aatggcgcgt gggatagtag tgcgctggag gagtggctcc agcgacagaa aaaagtatcg   1080
atagagcgaa tatttgagaa tatagggccc agcgcggtgt atccgagcat attacctggg   1140
gtggtgatag cgtcaccttc gcagacgcat cccgattatt tttatcagtg gataagggat   1200
agcgcgctta cgataaatag tatagtaagc cattcagcgg atccggcaat agagacgtta   1260
ctgcagtatc tgaatgtatc atttcatctg cagcgaacaa ataatacact gggcgcaggc   1320
ataggatata cgaatgatac agtggcgcta ggagatccta aatggaatgt agataatacg   1380
```

-continued

```
gcgtttacgg agccttgggg aaggcctcag aatgatggcc ctgcacttcg aagcatagcg   1440

atattaaaaa taatagatta tataaaacag agtggcacgg atctgggggc gaaatatccg   1500

tttcagagca cggcagatat atttgatgat atagtacggt gggatctgag gtttataata   1560

gatcattgga atagcagcgg atttgatcta tgggaggagg taaatggcat gcattttttt   1620

acgttactgg tacagctgtc ggcagtggat aggtcgctgt cgtattttaa tgcatcagag   1680

cggtcgtcgc cctttgtgga ggagctcagg cagacacgcc gggatatatc gaaattttta   1740

gtggatcctg cgaatgggtt tataaatggc aaatataatt atatagtgga gacacccatg   1800

atagcagata cactgcggtc aggactggat atatcaacat tattagcggc gaatacggtg   1860

catgatgcgc ccagtgcgag ccatcttccg tttgatataa atgatcctgc agtgctgaat   1920

acgctccatc atctaatgct tcatatgcgc tcgatatatc ccataaatga tagcagtaaa   1980

aatgcaacgg ggatagcact gggccggtat cctgaggatg tatatgatgg atatggcgtg   2040

ggcgagggaa atccctgggt actggcgacg tgcgcagcat caacaacgct ttatcagctc   2100

atatatcggc atataagcga gcagcatgat ctggtggtgc ctatgaataa tgattgctcg   2160

aatgcatttt ggagcgagct ggtatttagc aatctcacga cacttggaaa tgatgagggc   2220

tatctaatac tagagtttaa tacacctgca tttaatcaga caatacagaa aatatttcag   2280

ctagcagatt catttctagt gaaactgaaa gcaacgtggg agcagacggg gaattaa      2337
```

```
<210> SEQ ID NO 23
<211> LENGTH: 2337
<212> TYPE: DNA
<213> ORGANISM: Saccharomyces cerevisiae

<400> SEQUENCE: 23

atggtaggcc tcaaaaatcc ttatacgcat acaatgcaac gcccgtttct actcgcatat     60

ctagtgcttt cgcttctatt taattcagca ctcggatttc ccacagcact agtgcctcgc    120

ggaagctcga gcagcaatat aacgagcagc ggaccgtctt caactccgtt tagcagtgct    180

acggagagct tttcaacggg cacgacggtg acgccctcat caagtaaata tcctggcagt    240

aaaacagaga cgtcggtttc tagcacaaca gaaacaacga tagtaccgac gacaacaacg    300

actagtgtaa taacaccttc aacaacaacg ataacaacga cggtgtgcag cacaggaaca    360

aattcggcag gagagacaac tagcggatgc tcgcctaaga cgataacaac aactgtgccc    420

tgctcaacaa gtcccagcga gacggcatcg gagtcaacaa cgacgtcacc tacaacacct    480

gtaacgacag tggtgtcaac aaccgtagtg acaacggagt atagcacaag tacaaaacag    540

gggggagaga taacaacaac atttgtaacg aaaaatattc caacaacata cctaacgaca    600

atagcaccaa catcatcagt aacgacggtt acaaatttta ccccgacaac gataacaact    660

acggtatgct cgacaggaac aaactcagcg ggggaaacaa cgtcgggatg cagcccaaaa    720

acggtgacaa caacagttcc ttgctcaaca gggactggcg agtacacgac ggaggcgaca    780

gcacctgtga caacagctgt gacaaccacg gtagtgacga cagagtccag cacgggaacg    840

aatagcgcgg gtaagacgac aacaagttat acaacaaaat cagtacccac cacgtatgta    900

tttgattttg gcaagggcat actcgatcag agctgcggcg gggtattttc aaataatggc    960

tcatcgcagg tgcagctgcg ggatgtagta ttaatgaatg ggacagtggt atatgattca   1020

aatggcgcat gggatagtag tgcgctggag gagtggctcc agcgacagaa aaaagtttcc   1080

atagagagga tatttgagaa tatagggccc agcgcagtgt atccgtcaat tttacctggg   1140

gtggtgattg cgtcaccgtc gcaaacgcat ccggattatt tttatcagtg gataagggat   1200
```

```
agcgcgttga cgataaatag tatagtctca cattctgcgg atccggcaat agagacgtta   1260
ttgcagtatc tgaatgtgtc atttcatctc cagcggacaa ataacacact aggcgcaggc   1320
ataggatata ctaacgatac agtggcgcta ggagatccta aatggaacgt agataatacg   1380
gcgtttacgg agccttgggg acgtcctcag aacgatggcc ctgcgcttcg aagcatagca   1440
atattaaaaa taatagatta tatcaagcag tctggcactg atctgggggc caaatacccg   1500
tttcagtcca cggcagatat atttgatgat atagtacgtt gggatctgag gttcataatt   1560
gaccactgga attcgtcagg atttgatcta tgggaggaag taaatggcat gcattttttt   1620
acattactgg tacagctgtc agcagtggat aggtcgctgt cgtattttaa tgcgtcagaa   1680
cggtcgagtc cctttgtgga ggaactccga cagacacgcc gggatatatc gaagttttta   1740
gtggatcctg cgaatgggtt tatcaatggc aaatataatt atatagtgga gacacccatg   1800
atagccgata cactcaggtc cggactggat ataagcacat tattagcagc gaatacggtg   1860
catgatgcgc cttctgcgtc gcatcttccg tttgatataa atgatcctgc ggtactgaac   1920
acgctccacc atcttatgct acatatgcgg tcgatatatc ccataaatga tagctcgaaa   1980
aatgcaacgg ggatagcgct gggccggtat cctgaggatg tatatgatgg atatggcgtg   2040
ggcgagggaa atccctgggt actggcgacg tgcgcggcgt caacaacgct ttatcagctc   2100
atatatagac atatctcgga gcagcatgat ttggtggtgc ccatgaataa tgattgctcg   2160
aatgcatttt ggagcgagct ggtattctca aatctcacga cattgggaaa tgatgagggc   2220
tatttgatac tcgagtttaa tacacctgcg tttaatcaaa cgatacagaa aatatttcaa   2280
ctagctgatt catttctcgt aaaactgaaa gcaacgtggg agcagacggg gaattaa      2337
```

<210> SEQ ID NO 24
<211> LENGTH: 2337
<212> TYPE: DNA
<213> ORGANISM: Saccharomyces cerevisiae

<400> SEQUENCE: 24

```
atggtaggcc tcaaaaatcc ctatacgcat acaatgcaac gcccatttct actcgcatat     60
ttggtccttt cgcttctatt taattcagct ttggggtttc caacggcact agtgcctcgc    120
ggaagtagtt cgagcaatat aacatcctcc ggtcctagct caacaccatt tagctctgct    180
acggagagct tttctactgg cacaacggtg acgccctcat caagtaaata tcctggcagt    240
aaaacagaaa ctagtgtttc ttctacaacc gaaactacaa tagtacccac gacaacaacg    300
acatctgtga taacaccctc aacaacgaca ataaccacga cggtttgctc tacaggaaca    360
aacagcgcgg gtgagacgac tagcggatgc tctccgaaga ccataacaac gacagttcca    420
tgttcaacca gtcccagcga aaccgcatcg gagtcaacaa cgacgtcacc tacgacacct    480
gtaacaacag tggtatcaac cacagtagta actacagagt attcgacgag tacaaaacag    540
ggtggggaga taacaacaac atttgtcacc aaaaatattc caacaacgta tctaacaaca    600
attgcaccaa cttcatcagt gacaacggta accaatttca cgcccacgac tataactacg    660
acggtttgct cgacaggaac aaattcggcc ggtgagacaa cctcaggatg cagtcctaaa    720
acagtaacaa caacggtgcc ttgctcaaca ggtacaggcg agtacactac ggaggcaacc    780
gcgcctgtta caacagcggt aacaaccacc gtagttacga ctgagagctc aacgggtact    840
aactccgcag gaaagacgac aacaagttac acaacaaaat ctgtaccaac cacatatgta    900
tttgactttg gcaaaggcat actcgatcaa agctgcggcg gagtattttc aaataatggc    960
```

```
agctcgcagg tgcagctgcg ggatgtagtg ttgatgaatg ggacagtggt atacgattca   1020

aacggcgctt gggacagtag tgcgctggag gagtggctcc agcgacagaa aaaagtgtcc   1080

atagagagga tatttgaaaa tattgggccc agcgcagtgt atccgtctat actacctggg   1140

gtagtgatag cgtcaccctc gcagacgcat ccagattatt tttaccagtg gataagggat   1200

agcgcgttaa cgataaatag tatagtaagt catagcgcgg atccggcaat agagacgtta   1260

ttgcagtacc tgaatgtttc atttcacttg cagagaacga ataatacact aggcgctggc   1320

ataggttaca ctaatgatac agtggcgctg ggagacccta aatggaacgt agataacacg   1380

gcgttcacgg agccttgggg acgtcctcag aacgatggcc ctgctcttcg aagcatagcc   1440

atattaaaaa taatcgacta tataaaacaa tctggcactg atctgggggc caagtatcct   1500

ttccagtcca ccgcagatat atttgatgat atagtacgct gggatctgag gttcataata   1560

gatcattgga attcttcagg atttgatcta tgggaggagg taaatggcat gcatttcttt   1620

actttactgg tacagctgtc agcagtggac aggtcgctgt cgtattttaa tgcatcagaa   1680

cggtcgagtc cctttgtaga agaacttcgg cagacacgcc gggatatatc gaagttttta   1740

gtggatcctg cgaatgggtt tataaacggc aaatacaatt atatagttga gacacccatg   1800

attgcagata cacttcgatc aggactggat atatccacat tattagcagc gaatacagtc   1860

catgatgcgc cctcggcgtc gcatcttccg ttcgatataa atgatcctgc ggtgctgaat   1920

acgctacatc atttgatgct tcacatgcgt tcgatatacc ccataaatga tagcagcaaa   1980

aatgcaacgg gtatagccct gggccggtat cctgaggatg tatatgatgg atatggcgtt   2040

ggcgagggaa atccctgggt gctggcgacg tgtgcggctt caacaacgct ttatcagctc   2100

atatataggc atataagcga gcagcatgat ctggtggtac ctatgaataa cgattgctcg   2160

aatgcatttt ggagcgagct ggtattttcc aacctcacga ctcttggaaa tgatgaaggc   2220

tatcttattt tggagttcaa tacacctgcg tttaatcaga caatacaaaa aatattccaa   2280

ctagcagatt cattcttggt gaaactgaaa gccacgtggg aacagacggg gaattaa      2337
```

```
<210> SEQ ID NO 25
<211> LENGTH: 2337
<212> TYPE: DNA
<213> ORGANISM: Saccharomyces cerevisiae

<400> SEQUENCE: 25

atggtaggcc tcaaaaatcc gtatacgcat actatgcaaa gaccttttct actcgcgtat     60

ttggtccttt cgcttctatt taattcagca ttggggtttc cgactgcact agtgcctaga    120

ggatcctcga gcagcaacat aacttcctca ggtccatctt caactccgtt tagctctgca    180

actgagagct tttctacagg cactactgtg acaccatcat catcgaaata ccctggcagt    240

aaaacagaaa cgtctgtgtc tagtacaaca gaaacgacga tagtaccaac tacaactacg    300

acttctgtga taacaccatc aacaaccact attaccacta cggtatgctc gacaggaaca    360

aatagtgcag gcgaaacaac ttctggatgc tctcctaaga caattacaac aactgtgcca    420

tgctcaacca gtccaagcga gacagcatcg gagtcaacaa ccacttcacc tacaacacct    480

gtaacaacag ttgtgtcaac gaccgtcgtt actacggagt attcgactag tacaaaacag    540

ggtggagaga ttacaacaac atttgtcacc aaaaacattc caacgactta cctaactaca    600

attgctccaa cttcatcagt gacaacggtg accaatttta ccccaaccac tattactacg    660

acggtttgct ctacaggaac aaatagtgcg ggtgaaacta cctctggatg ctcgccaaag    720

actgtcacaa caactgttcc ttgctcaacg ggtactggcg agtatacgac ggaggctacc    780
```

```
gcgcctgtta caacagctgt cacaaccacc gttgtaacca ctgagagctc tacggggact    840

aatagcgctg gaaagacgac aactagttac acaacaaaat ctgtacccac cacctatgta    900

tttgattttg gcaaaggcat tctcgatcaa agctgcggcg gggtattttc aaataacggc    960

tcttcgcaag tgcagctgcg ggatgtagtc ttgatgaatg ggacagtggt atacgattca   1020

aatggcgctt gggacagtag tgcgctggag gagtggctcc agcgacagaa aaaagtttcg   1080

atcgagagaa tatttgaaaa tattgggccc agcgcggtgt atccgtctat tttgcctggg   1140

gtggtgatag cgtcaccatc gcaaacgcat ccagattact tttatcaatg gataagggac   1200

agcgcgctca cgataaatag tatagtctct catagcgcgg atccggcaat agagacgtta   1260

ttgcagtacc tgaacgtatc atttcacttg cagagaacca acaatacatt gggcgctggc   1320

attggttata ctaatgatac agtggctctg ggagacccta agtggaacgt cgataatacg   1380

gcttttacgg aaccttgggg ccgtcctcaa aatgatggcc ctgcgcttcg aagcattgcc   1440

atcttaaaaa taatagatta catcaagcag tctggcacag atctgggggc caaataccca   1500

tttcagagca cggcagatat atttgatgat attgtacgtt gggatctgag gttcataata   1560

gatcactgga attctagcgg atttgatcta tgggaggaag tgaatggcat gcatttcttt   1620

actttactgg tacagctgtc tgcagtggac aggtcgctgt cgtattttaa cgcctcagaa   1680

cggtcgtctc cctttgtgga agaattgcgc cagacacgcc gggacatatc caagttttta   1740

gtggaccctg cgaatgggtt tataaatggc aagtacaatt atatagttga gacacccatg   1800

attgcggaca cattgcgaag tggactggat atatcaacat tattagcagc gaacaccgtg   1860

cacgatgcgc ctagtgcttc ccatcttccg tttgatataa atgatcctgc cgtactgaac   1920

acgctccacc atttgatgtt gcacatgcgt tcgatatacc ccataaacga tagcagtaaa   1980

aatgcaacgg gtatagccct gggccggtat cctgaggacg tatatgatgg atatggcgta   2040

ggcgagggaa atccctgggt cctggccacg tgcgccgcat caacaacgct ttatcagctc   2100

atatatcgcc atataagtga gcagcatgac ttggtagtac caatgaataa cgattgttcg   2160

aatgcatttt ggagcgagct ggtattttca aatctcacga cgttgggaaa tgatgaaggc   2220

tatttaatac tcgagttcaa tacacctgcc tttaatcaga ccatacagaa aatctttcag   2280

ctagcggatt cattcttggt caagctgaaa gccacgtggg aacagacggg gaattaa      2337
```

<210> SEQ ID NO 26
<211> LENGTH: 2337
<212> TYPE: DNA
<213> ORGANISM: Saccharomyces cerevisiae

<400> SEQUENCE: 26

```
atggtaggcc tcaaaaatcc atatacgcac actatgcaga gaccatttct actcgcttat     60

ttggtccttt cgcttctatt taactcagca ctcggttttc cgactgcact agttcctaga    120

ggatcgtcct ctagcaacat cacttcctcg ggaccatctt caactccatt cagctctgct    180

acggaaagct tttctacggg cactactgtc actccatcat catccaaata ccctggcagt    240

aaaacagaaa cgagcgtttc ttctacaacc gaaactacca ttgtacctac gacaactacg    300

acttctgtca taacaccatc aacaaccact attacaacta cggtttgctc gacaggaaca    360

aactcagccg gtgaaactac gtctggatgc agtcctaaga ccattacaac gactgttcca    420

tgttcaacca gtccaagcga aacggcatcg gaatcaacaa cgacttcacc taccacacct    480

gtaactacag ttgtatcaac caccgtcgtt actactgagt attctacaag tacaaaacaa    540
```

```
ggtggtgaga taacaacgac atttgtgacc aaaaacattc caacgactta cctaactaca    600
atagctccaa cttcatcagt cactacggtt accaatttca ccccaaccac tataactact    660
acggtttgct ctacaggaac aaactctgcc ggcgaaacga cctctggatg ctctccgaag    720
actgtcacaa caacggttcc ttgttcaact ggtactggcg agtatacgac tgaagctacc    780
gcccctgtta caacagctgt cacaaccacc gtagttacga ctgaaagttc tacgggtact    840
aactcggctg gtaagacgac aacgagttac acaacaaagt ctgtaccaac gacctatgta    900
tttgactttg gcaaaggcat actcgatcaa agctgcggcg gtgtattttc aaacaacggc    960
tcttcgcaag tgcagctgcg ggatgtagtc ttaatgaatg ggacagtggt atacgattca   1020
aacggcgctt gggatagtag tgcgctggag gagtggctcc agcgacagaa aaaagtttcc   1080
atagaaagaa tatttgaaaa tattgggccc agcgccgtgt atccgtcgat actccctggg   1140
gtggtgattg cgtcaccatc gcaaacgcat ccagactatt tctatcaatg gataagggac   1200
agcgcgctga cgataaacag tattgtctct cattctgcgg acccggcaat agagacgtta   1260
cttcagtacc tgaacgtatc atttcacttg caaagaacca acaatacact aggcgctggc   1320
attggttata ctaacgatac agtggctttg ggagacccta agtggaacgt cgacaacacg   1380
gctttcacgg aaccttgggg tcgacctcaa aacgatggcc ctgctcttcg aagcatagcc   1440
atcttaaaaa tcatcgacta tatcaaacaa tctggcactg atctgggggc gaaataccca   1500
ttccagtcca ccgcagatat ctttgatgat attgtacgtt gggacctgag gttcattatt   1560
gaccactgga attcttccgg atttgatcta tgggaggaag tcaatggcat gcatttcttt   1620
acattactgg tacaactgtc tgcagtggac aggtcgctgt cgtattttaa cgcctcagag   1680
cggtcgtcgc cctttgtgga agaattgcga cagacacgcc gggatatctc caagttttta   1740
gtggatcctg cgaatgggtt tatcaatggc aaatacaatt atatagtgga gacacccatg   1800
attgccgaca cattgagatc cggactggac atatccacgt tattagcggc gaacaccgtc   1860
cacgatgcgc catcagcgtc ccatcttccg ttcgatatca atgaccctgc cgtcctgaac   1920
acgttgcacc atttaatgtt gcacatgcgt tcgatatatc ccatcaacga tagctccaaa   1980
aatgcaacgg gtattgccct gggccggtat cctgaggatg tatatgatgg atatggcgtt   2040
ggcgagggaa atccctgggt cctggccacg tgtgcagctt caacaacgct ttatcagctc   2100
atttatagac acatctctga gcagcatgac ttggttgtcc caatgaacaa cgattgttcg   2160
aatgcatttt ggagcgagct ggtattttcc aacctcacga cattgggaaa tgatgagggc   2220
tatttgattt tggagtttaa tacacctgca ttcaatcaga ccatacagaa aatatttcaa   2280
ctagcggatt catttttggt aaagctgaaa gcaacgtggg aacagacggg gaactaa      2337
```

<210> SEQ ID NO 27
<211> LENGTH: 2337
<212> TYPE: DNA
<213> ORGANISM: Saccharomyces cerevisiae

<400> SEQUENCE: 27

```
atggtaggcc tcaaaaatcc atatacgcac actatgcaaa gaccatttct actcgcttat     60
ttggtccttt cgcttctatt taactcagct ttgggttttc caactgcact agttcctaga    120
ggatcgtcct ctagcaacat cacttcctcc ggtccatctt caacaccatt cagctctgct    180
actgaaagct tttctactgg cactactgta actccttcat catccaaata ccctggcagt    240
aaaacagaaa cttctgtttc ttctacaacc gaaactacca ttgttccaac tacaactacg    300
acttctgtca taacaccatc aacaaccact attaccacta cggtttgctc tacaggaaca    360
```

```
aactctgccg gtgaaactac ttctggatgc tctcccaaga ccattacaac tactgttcca    420

tgttcaacca gtccaagcga aaccgcatcg gaatcaacaa ccacttcacc taccacacct    480

gtaactacag ttgtgtcaac caccgtcgtt actactgagt attcgactag tacaaaacaa    540

ggtggtgaaa ttacaacaac atttgtcacc aaaaacattc caaccactta cctaactaca    600

attgctccaa cttcatcagt cactacggtt accaatttca ccccaacaac tattactact    660

acggtttgct ctacaggaac aaactctgcc ggtgaaacta cctctggatg ctctccaaag    720

acggtcacaa caactgttcc ttgttcaact ggtactggcg aatacactac tgaagctacc    780

gcacctgtta caacagctgt cacaaccacc gttgtgacca ctgaatcctc tacgggcact    840

aattccgctg gtaagacgac aactagttac acaacaaagt ctgtaccaac cacctatgta    900

tttgactttg gcaagggcat tctcgatcag agctgcggcg gtgtattttc aaataacggc    960

tcttcgcaag tgcagctgcg ggatgtagtc ttgatgaatg ggacagtggt atacgattca   1020

aacggcgctt gggacagtag tgcgctggag gagtggctcc agcgacagaa aaaagtttcc   1080

atcgaaagaa tatttgaaaa tattgggccc agcgccgtgt atccgtctat tttgcctggg   1140

gtcgtgattg cgtcaccatc gcaaacgcat ccagactact tctaccaatg gataagggac   1200

agcgcgttga cgataaacag tattgtctct cattctgcgg atccggcaat agagacgtta   1260

ttgcagtacc tgaacgtatc attccacttg caaagaacca acaacacatt gggcgctggc   1320

attggttaca ctaacgatac agtggctttg ggagacccta aatggaacgt cgacaacacg   1380

gctttcacgg aaccttgggg tcgtcctcaa aacgatggcc ctgctcttcg aagcattgcc   1440

atcttaaaaa taatcgacta tatcaagcaa tctggcactg atctgggggc caagtaccca   1500

ttccagtcca ccgcagatat ctttgatgat attgtacgtt gggacctgag gttcattatt   1560

gaccactgga attcttccgg atttgatcta tgggaggaag tcaatggcat gcatttcttt   1620

actttactgg tacaactgtc tgcagtggat aggtcgctgt cgtattttaa cgcctcagaa   1680

cggtcgtctc cctttgtaga agaattgcgt cagacacgcc gggacatctc caagttttta   1740

gtggaccctg cgaatgggtt tatcaacggc aagtacaatt atattgttga gacacccatg   1800

attgccgaca cattgagatc cggactggac atatccactt tattagctgc gaacaccgtc   1860

cacgatgcgc catctgctag tcatcttccg ttcgatatca atgaccctgc cgtcctgaac   1920

acgttgcacc atttgatgtt gcacatgcgt tcgatatacc ccatcaacga tagctccaaa   1980

aatgcaacgg gtattgccct gggccggtat cctgaggacg tatatgatgg atatggcgtt   2040

ggcgagggaa atccctgggt cctggccacg tgtgccgctt caacaacgct ttatcagctc   2100

atttaccgac acatctctga gcagcatgac ttagttgtcc caatgaacaa cgattgttcg   2160

aacgcatttt ggagcgagct ggtattctcc aacctcacga ctttgggaaa tgacgaaggc   2220

tatttgattt tggagttcaa tacacctgcc ttcaatcaaa ccatacaaaa aatcttccaa   2280

ctagctgatt cattcttggt caagctgaaa gccacgtggg aacagacggg gaactaa      2337
```

```
<210> SEQ ID NO 28
<211> LENGTH: 2337
<212> TYPE: DNA
<213> ORGANISM: Saccharomyces cerevisiae

<400> SEQUENCE: 28

atggtcggcc tcaaaaatcc atatacgcac actatgcaaa gaccattttt gctcgcttat     60

ttggtccttt cgcttctatt caactcagct ttgggtttcc caactgcact agttcctaga    120
```

```
ggatcctcct ctagcaacat cacttcctcc ggtccatctt caactccatt cagctctgct    180

actgaatcct tttctactgg cactactgtc actccatcat catccaagta ccctggcagt    240

aagacagaaa cttctgtttc ttctaccacc gaaactacca ttgttccaac tacaactacg    300

acttctgtca taaccccatc aacaaccact attaccacta cggtttgctc tacaggaaca    360

aactctgccg gtgaaactac ttctggatgc tctccaaaga ccattactac tactgttcca    420

tgttctacca gtccaagcga aaccgcttcg gaatcaacaa ccacttcacc taccacacct    480

gtaactacag ttgtctcaac caccgtcgtt actactgagt attctacttc cacaaaacaa    540

ggtggtgaaa ttacaactac atttgtcacc aagaacattc caaccactta cctaactaca    600

attgctccaa cttcatcagt cactacggtt accaatttca ccccaaccac tattactact    660

acggtttgtt ctacaggaac aaactctgcc ggtgaaacta cctctggatg ctctccaaag    720

actgtcacaa caactgttcc ttgttcaact ggtactggcg aatacactac tgaagctacc    780

gcccctgtta caacagctgt cacaaccacc gttgttacca ctgaatcctc taccggtact    840

aactccgctg gtaagacgac aactagttac acaacaaagt ctgtaccaac cacctatgta    900

tttgactttg gcaagggcat tctcgatcaa agctgtggcg gtgtattttc aaacaacggc    960

tcttcgcaag tgcagctgcg ggacgtcgtc ttgatgaatg ggacagtggt atacgattca   1020

aacggcgctt gggacagtag tgcgctggag gagtggctcc agcgacagaa aaaagtttcc   1080

atcgaaagaa tctttgaaaa tattgggccc agcgccgtgt atccgtctat tttgcctggg   1140

gtcgtgattg cttcaccatc gcaaacgcat ccagactact tctaccaatg gattagggac   1200

agcgcgttga cgataaacag tattgtctct cactctgccg acccggcaat agagacgtta   1260

ttgcagtacc tgaacgtttc attccacttg caaagaacca acaacacatt gggcgctggc   1320

attggttaca ctaacgatac agtggctttg ggagacccta agtggaacgt cgacaacacg   1380

gctttcacgg aaccttgggg tcgtcctcaa aacgatggcc ctgctcttcg aagcattgcc   1440

atcttaaaga tcatcgacta catcaagcaa tctggcactg atctgggtgc caagtaccca   1500

ttccagtcca ccgcagatat ctttgatgat attgttcgtt gggacctgag gttcattatt   1560

gaccactgga attcttccgg atttgaccta tgggaagaag tcaatggcat gcatttcttt   1620

actttactgg tacaactgtc tgcagtcgac aggtcgctgt cgtattttaa cgcctcagaa   1680

cgttcgtctc cctttgttga agaattgcgt cagacacgca gagacatctc caagtttttg   1740

gttgaccctg ctaatgggtt tatcaacggc aagtacaatt atattgttga gacaccaatg   1800

attgccgaca cattgagatc cggactggac atctccactt tgttagctgc taacaccgtc   1860

cacgatgcgc catctgcttc ccatttgccg ttcgatatca acgaccctgc cgtcttgaac   1920

acgttgcacc atttgatgtt gcacatgcgt tcgatatacc ccatcaacga tagctccaaa   1980

aatgcaaccg gtattgccct gggccgttac cctgaggacg tatatgacgg atatggcgtt   2040

ggcgagggaa acccctgggt cctggccacg tgtgccgctt caacaacgct ttatcagctc   2100

atttacagac acatctctga gcagcacgac ttggttgtcc caatgaacaa cgattgttcg   2160

aacgcatttt ggagcgagct ggtattctcc aacctcacga ctttgggaaa tgacgaaggc   2220

tatttgattt tggagttcaa tacacctgcc ttcaatcaaa ccatacaaaa aatcttccaa   2280

ctagctgatt cattcttggt caagctgaaa gccacgtggg aacagacggg gaactaa      2337
```

<210> SEQ ID NO 29
<211> LENGTH: 2337
<212> TYPE: DNA
<213> ORGANISM: Saccharomyces cerevisiae

<400> SEQUENCE: 29

```
atggtaggcc tcaaaaaccc atatacgcac actatgcaaa gaccattcct actcgcttac      60
ttggtcttgt cgttgctatt taactctgct ttgggttttc caactgctct agttcctaga     120
ggttcctcct cttctaacat cacttcctcc ggtccatctt caactccatt cagctctgct     180
actgaatctt tttctactgg tactactgtc actccatctt cttccaagta ccctggcagt     240
aaaacagaaa cttctgtttc ttctacaacc gaaactacca ttgttccaac tacaactacg     300
acttctgtca tcacaccatc aacaaccact attaccacta ccgtttgttc taccggtacc     360
aactctgccg gtgaaactac ttctggttgc tctccaaaga ccattacaac tactgttcca     420
tgttccacca gtccatctga aaccgcatcg gaatctacaa ccacttcacc taccacacct     480
gtaactacag ttgtctccac caccgtcgtt actactgaat attctactag tacaaaaacaa    540
ggtggtgaaa ttacaactac atttgtcacc aaaaacattc caaccactta cctaactaca     600
attgctccaa cttcatcagt cactacggtt accaatttca ccccaaccac tattactact     660
actgtttgtt ctactggaac aaactctgcc ggtgaaacta cctctggatg ctctccaaag     720
actgtcacaa caactgttcc atgttccact ggtactggcg aatacactac tgaagctacc     780
gcccctgtta ccacagctgt cacaaccacc gttgttacca ctgaatcctc tactggtact     840
aactccgctg gtaagaccac cacttcttac actactaagt ctgtaccaac cacctacgta     900
tttgacttcg gtaagggcat tctcgatcaa tcttgcggcg gtgtattttc aaacaacggt     960
tcttcgcaag tgcaactgcg tgatgtagtc ttgatgaatg gtacagtggt atacgattcc    1020
aacggcgctt gggacagtag tgcgctggag gagtggctcc agcgacaaaa aaaagtttcc    1080
atcgaaagaa tttttgaaaa cattggtccc agcgccgtgt acccgtctat tttgccaggt    1140
gtcgtgattg cttcaccatc gcaaactcat ccagactact tctaccaatg gattagggac    1200
agcgcgttga ccataaactc tattgtctct cattctgctg acccagcaat cgagaccttg    1260
ttgcaatacc tgaacgtttc cttccacttg caaagaacca acaacacttt gggcgctggc    1320
attggttaca ctaacgatac agtggctttg ggtgacccaa agtggaacgt cgacaacacg    1380
gctttcaccg aaccatgggg tcgtcctcaa aacgatggtc ctgctcttcg aagcattgcc    1440
atcttgaaaa tcatcgacta catcaagcaa tctggtactg atctgggtgc caagtaccca    1500
ttccaatcca ccgcagatat ctttgatgac attgttcgtt gggacctgag gttcattatt    1560
gaccactgga attcttccgg atttgatcta tgggaagaag tcaatggcat gcacttcttt    1620
actttattgg tacaactgtc tgctgtggac aggtcgctgt cgtatttcaa cgcctcagaa    1680
cggtcgtctc catttgttga agaattgcgt caaactcgcc gtgacatctc caagttctta    1740
gttgacccag cgaatgggtt tatcaacggc aagtacaact atattgttga aacacccatg    1800
attgccgaca cattgagatc cggattggac atatccactt tattggctgc taacaccgtc    1860
cacgatgcgc catctgcttc ccatcttccg ttcgacatca atgacccagc cgtcttgaac    1920
acgttgcacc acttgatgtt gcacatgcgt tcgatatacc caatcaacga cagctccaaa    1980
aacgcaacgg gtattgcctt gggccggtat cctgaagacg tatatgatgg atatggcgtt    2040
ggcgaaggaa atccatgggt cctggccacc tgtgccgctt caactacgtt gtaccaactc    2100
atttacagac acatctctga acaacatgac ttggttgtcc caatgaacaa cgattgttcc    2160
aacgcttttt ggagcgaact ggttttctcc aacttgacga ctttgggaaa tgacgaaggt    2220
tatttgattt tggagttcaa cacaccagcc ttcaaccaaa ccattcaaaa aatcttccaa    2280
```

```
ctagctgact cattcttggt caagttgaaa gccacgtggg aacagacggg gaactaa      2337


<210> SEQ ID NO 30
<211> LENGTH: 2337
<212> TYPE: DNA
<213> ORGANISM: Saccharomyces cerevisiae

<400> SEQUENCE: 30

atggtcggtc tcaagaaccc atatactcac actatgcaaa gaccattcct actcgcttat     60

ttggtcttgt ctttgttgtt taactcagct ttgggtttcc caactgcatt ggttccaaga    120

ggttcctcct cttctaacat cacttcctcc ggtccatctt ctactccatt ctcttctgct    180

actgaatcct tctctactgg tactactgtc actccatctt catccaagta ccctggctct    240

aagactgaaa cttctgtttc ttctacaacc gaaactacca ttgttccaac tactactacc    300

acttctgtca tcacaccatc aacaaccact attaccacta cggtttgctc tactggaact    360

aactctgccg gtgaaactac ttctggttgt tctccaaaga ccattaccac tactgttcca    420

tgttctacca gtccatccga aaccgcctct gaatccacta ccacttctcc taccacacca    480

gtcactaccg ttgtctcaac caccgtcgtt actactgaat actctactag tacaaaaacaa   540

ggtggtgaaa ttacaactac cttcgtcacc aaaaacattc caaccactta cttgactact    600

attgctccaa cttcatcagt cactacggtt accaacttca ccccaaccac tattactact    660

actgtttgct ctaccggtac caactctgcc ggtgaaacta cctctggttg ttctccaaag    720

actgtcacaa ctactgttcc ttgttccact ggtactggtg aatacactac tgaagctacc    780

gcccctgtta ccacagctgt caccaccacc gttgttacca ctgaatcctc tactggtact    840

aactccgctg gtaagacgac cactagttac actacaaagt ctgtaccaac cacctacgta    900

ttcgacttcg gtaagggtat tctcgaccaa agctgcggtg gtgtattctc aaacaacggt    960

tcttcgcaag ttcaattgcg ggacgtagtc ttgatgaacg ggaccgttgt atacgattca   1020

aacggcgctt gggactcctc cgctttggaa gaatggttgc agagacagaa aaaggtttcc   1080

atcgaaagaa tattcgaaaa cattggtccc agcgccgtgt acccatctat tttgcctggg   1140

gtcgtcattg cctcaccatc ccaaacgcat ccagactact tctaccaatg gatcagagac   1200

tccgctttga cgataaactc tattgtctct cactctgcgg acccagctat tgaaacgttg   1260

ttgcaatacc tgaacgtttc attccacttg caaagaacca acaacacctt gggcgctggc   1320

attggttaca ctaacgacac agtggctttg ggagacccaa agtggaacgt cgacaacacc   1380

gctttcacgg aaccatgggg tcgtccacaa aacgatggtc ctgctttgcg atccattgcc   1440

atcttgaaaa tcatcgacta catcaagcaa tctggtactg acctgggggc caagtaccca   1500

ttccaatcca ccgccgacat ctttgacgat attgttcgtt gggacttgag attcattatt   1560

gaccactgga actcttccgg attcgaccta tgggaagaag tcaacggtat gcatttcttc   1620

actttactgg tacaactgtc tgcagtcgac aggtctttgt cgtacttcaa cgcctcagaa   1680

agatcgtctc ccttcgttga agaattgcgt cagactcgtc gggacatctc caagtttttg   1740

gttgaccctg cgaatggttt catcaacggc aagtacaact atattgttga aacaccaatg   1800

attgccgaca ctttgagatc cggtttggac atttccactt tgttagctgc gaacaccgtc   1860

cacgacgccc catctgcttc ccaccttcca ttcgacatca atgacccagc cgtcctgaac   1920

acgttgcacc atttgatgtt gcacatgcgt tccatttacc caatcaacga ttcttccaag   1980

aatgccactg gtattgccct gggtagatat ccagaggacg tatatgacgg ttatggtgtt   2040

ggcgaaggta acccctgggt cctggccacc tgtgccgctt caacaacgct ttatcaattg   2100
```

```
atttacagac acatctctga gcagcatgac ttggttgtcc caatgaacaa cgattgttcc   2160

aacgcctttt ggtccgaatt ggtattctcc aacttgacga ctttgggtaa tgacgaaggc   2220

tacttgattt tggaattcaa tactcctgcc ttcaaccaaa ccatccaaaa aatcttccaa   2280

ctagctgatt cattcttggt caagctgaag gccacttggg aacaaaccgg taactaa      2337
```

<210> SEQ ID NO 31
<211> LENGTH: 2337
<212> TYPE: DNA
<213> ORGANISM: Saccharomyces cerevisiae

<400> SEQUENCE: 31

```
atggtcggtt tgaagaaccc atacacccac actatgcaaa gaccattctt gttggcttac     60

ttggtcttgt cgttgttgtt caactccgct ttgggtttcc caactgcctt ggttccaaga    120

ggttcctcct cttccaacat cacttcctcc ggtccatctt ctactccatt ctcttctgct    180

actgaaagct tctctactgg tactactgtc actccatctt cctccaaata cccaggttct    240

aagaccgaaa cttctgtttc ttctactacc gaaactacca ttgttccaac tactactact    300

acttctgtca tcacaccatc cacaaccact attaccacta ccgtttgttc tactggtact    360

aactctgccg gtgaaactac ttctggatgt tctccaaaga ccattaccac tactgttcca    420

tgttctacct ccccaagcga aaccgcttct gaatctacaa ccacttcccc aaccactcca    480

gtcactaccg ttgtctctac caccgtcgtt actactgaat actctacttc cacaaagcaa    540

ggtggtgaaa ttaccactac tttcgtcacc aagaacattc caaccactta cctaactacc    600

attgctccaa cttcatcagt cactaccgtt accaacttca ccccaaccac tattactact    660

accgtttgtt ctactggtac aaactctgcc ggtgaaacta cctctggatg ttctccaaag    720

actgtcacaa caactgttcc ttgttctact ggtactggtg aatacactac tgaagctacc    780

gcccctgtta ctacagctgt cactaccacc gttgttacca ctgaatcctc tactggtact    840

aactccgctg gtaagactac cactagttac actaccaagt ctgtaccaac cacctacgtc    900

ttcgacttcg gcaagggtat tttggaccaa agctgtggtg gtgttttctc caacaacggt    960

tcttcccaag ttcaactgag agacgtcgtc ttgatgaacg gtacagtggt atacgattct   1020

aacggcgctt gggactcctc tgccttggaa gaatggttgc agcgtcagaa gaaggtttcc   1080

atcgaaagaa tcttcgaaaa cattggtccc tccgccgtct acccatctat tttgcctggt   1140

gtcgtcattg cttctccatc ccaaacgcac ccagactact tctaccaatg gatcagagac   1200

tctgcgttga ctataaacag tattgtctct cactctgctg acccggctat cgaaacttta   1260

ttgcaatact tgaacgtttc tttccacttg caaagaacca acaacacttt gggtgctggt   1320

attggttaca ctaacgacac tgttgctttg ggtgacccaa agtggaacgt cgacaacacg   1380

gctttcactg aaccatgggg tcgtccacaa aacgacggtc cagctttgcg ttccattgcc   1440

atcttgaaga tcatcgacta catcaagcaa tctggtactg acttgggtgc caagtaccca   1500

ttccaatcca ccgcagacat ctttgacgac attgtccgtt gggacttgag gttcattatt   1560

gaccactgga attcttccgg attcgacttg tgggaggaag tcaatggtat gcacttcttc   1620

actttattgg ttcaattgtc tgctgtggac cgttctctgt cctacttcaa cgcctccgaa   1680

cgttcgtctc cattcgttga agaattgcgt caaactcgta gagacatctc caagtttttg   1740

gtcgacccag ctaacggttt catcaacggc aagtacaact atattgttga aactccaatg   1800

attgccgaca ccttgagatc cggattggac atttccactt tgttggctgc caacaccgtc   1860
```

```
cacgacgcgc catctgcttc ccaccttcca ttcgacatca acgacccagc cgtcttgaac   1920

accttgcacc acttgatgtt gcacatgcgt tctatttacc ccatcaacga ctcctccaag   1980

aatgcaactg gtattgcctt gggtagatac ccagaagacg tatacgacgg ttatggtgtt   2040

ggtgaaggaa acccatgggt cttggccacc tgtgccgctt ccacaacttt gtatcagttg   2100

atttacagac acatctctga acaacacgac ttggttgtcc caatgaacaa cgactgttct   2160

aacgctttct ggtctgaatt ggttttctcc aacttgacca ctttgggtaa cgacgaaggt   2220

tacttgattt tggagttcaa cacccctgcc ttcaatcaaa ccattcaaaa gatcttccaa   2280

ttggctgact cattcttggt caagctgaaa gccacttggg aacaaaccgg gaactaa      2337
```

<210> SEQ ID NO 32
<211> LENGTH: 2337
<212> TYPE: DNA
<213> ORGANISM: Saccharomyces cerevisiae

<400> SEQUENCE: 32

```
atggtcggtt tgaagaaccc atacactcac actatgcaaa gaccattctt gttggcttac     60

ttggtcttgt ctttgttgtt caactctgct ttgggtttcc caactgcttt ggttccaaga    120

ggttcctcct cttccaacat cacttcctcc ggtccatctt ctactccatt ctcctctgct    180

actgaatctt tctctactgg tactactgtc actccatcct cttccaagta cccaggttcc    240

aagaccgaaa cttctgtttc ttctaccacc gaaactacca ttgttccaac tactactacc    300

acttctgtca ttactccatc taccaccact attaccacta ccgtttgttc taccggtacc    360

aactctgccg gtgaaactac ttctggttgt tctccaaaga ccattactac tactgttcca    420

tgttccacct ccccatccga aaccgcctcc gaatccacca ccacttctcc aaccactcca    480

gtcactaccg ttgtctccac caccgtcgtt actactgaat actctacttc taccaagcaa    540

ggtggtgaaa ttactactac tttcgtcacc aagaacattc caaccactta cttgactacc    600

attgctccaa cttcctctgt cactactgtt accaacttca ccccaaccac tattactact    660

actgtttgtt ctactggtac taactctgcc ggtgaaacta cctctggttg ttctccaaag    720

actgtcacta ctactgttcc atgttccact ggtactggtg aatacactac tgaagctacc    780

gccccagtta ccaccgctgt cactaccacc gttgttacca ctgaatcctc taccggtact    840

aactccgctg gtaagaccac cacttcttac actaccaagt ctgttccaac cacctacgtc    900

ttcgacttcg gtaagggtat tttggaccaa tcctgtggtg gtgttttctc caacaacggt    960

tcttcccaag tccaattgcg tgacgtcgtc ttgatgaacg gtactgtcgt ttacgactct   1020

aacggtgctt gggactcttc tgctttggaa gaatggttgc aacgtcaaaa gaaggtttcc   1080

atcgaaagaa tcttcgaaaa cattggtcca tctgccgttt acccatctat tttgccaggt   1140

gtcgtcattg cctctccatc ccaaacccac ccagactact tctaccaatg gatcagagac   1200

tctgccttga ccattaactc cattgtctct cactctgccg acccagccat cgaaaccttg   1260

ttgcaatact tgaacgtttc cttccacttg caaagaacca acaacacctt gggtgctggt   1320

attggttaca ctaacgacac tgtcgctttg ggtgacccaa agtggaacgt cgacaacacc   1380

gctttcactg aaccatgggg tcgtccacaa aacgacggtc cagctttgag atctattgcc   1440

atcttgaaga tcatcgacta catcaagcaa tctggtactg acttgggtgc caagtaccca   1500

ttccaatcca ccgccgacat cttcgacgac attgtccgtt gggacttgcg tttcattatt   1560

gaccactgga actcttccgg tttcgacttg tgggaagaag tcaacggtat gcacttcttc   1620

actttgttgg tccaattgtc tgccgttgac agatccttgt cttacttcaa cgcctctgaa   1680
```

```
cgttcttctc cattcgttga agaattgcgt caaactcgtc gtgacatctc caagttcttg   1740

gtcgacccag ccaacggttt catcaacggt aagtacaact acattgttga aaccccaatg   1800

attgccgaca ccttgagatc cggtttggac atctccactt tgttggctgc taacaccgtc   1860

cacgacgctc catctgcttc ccacttgcca ttcgacatca acgacccagc cgtcttgaac   1920

accttgcacc acttgatgtt gcacatgcgt tccatttacc caatcaacga ctcctccaag   1980

aacgccaccg gtattgcctt gggtagatac ccagaagacg tctacgacgg ttacggtgtt   2040

ggtgaaggta acccatgggt cttggccacc tgtgccgctt ccactacttt gtaccaattg   2100

atttacagac acatctctga acaacacgac ttggttgtcc caatgaacaa cgactgttcc   2160

aacgctttct ggtctgaatt ggtcttctcc aacttgacta ctttgggtaa cgacgaaggt   2220

tacttgattt tggaattcaa caccccagcc ttcaaccaaa ccatccaaaa gatcttccaa   2280

ttggctgact ccttcttggt caagttgaag gccacctggg aacaaactgg taactaa      2337


<210> SEQ ID NO 33
<211> LENGTH: 59
<212> TYPE: PRT
<213> ORGANISM: Artificial Sequence
<220> FEATURE:
<223> OTHER INFORMATION: Synthetic Construct

<400> SEQUENCE: 33

Met Pro Pro Lys Ala Ser Pro Thr Gly Ala Ser Ser Val Leu Lys Ala
1               5                   10                  15

Lys Ala Pro Ser Ile Pro Ala Lys Thr Val Gly Lys Thr Leu Pro Lys
            20                  25                  30

Thr Val Ile Thr Lys Leu Ser Thr Val Ile Thr Leu Gly Ala Ala Gly
        35                  40                  45

Leu Ile Val Pro Leu Ser Ile Gly Ile Gly Val
    50                  55
```